US008840891B2

(12) United States Patent
Rees Smith et al.

(10) Patent No.: US 8,840,891 B2
(45) Date of Patent: Sep. 23, 2014

(54) HUMAN MONOCLONAL ANTIBODIES TO THE THYROTROPIN RECEPTOR WHICH ACT AS ANTAGONISTS

(75) Inventors: Bernard Rees Smith, Cardiff (GB); Jadwiga Furmaniak, Cardiff (GB); Jane Sanders, Cardiff (GB)

(73) Assignee: RSR Limited, Cardiff (GB)

( * ) Notice: Subject to any disclaimer, the term of this patent is extended or adjusted under 35 U.S.C. 154(b) by 1402 days.

(21) Appl. No.: 12/527,218

(22) PCT Filed: Feb. 14, 2008

(86) PCT No.: PCT/GB2008/000518
§ 371 (c)(1),
(2), (4) Date: Jun. 3, 2010

(87) PCT Pub. No.: WO2008/099185
PCT Pub. Date: Aug. 21, 2008

(65) Prior Publication Data
US 2013/0183313 A1    Jul. 18, 2013

Related U.S. Application Data

(60) Provisional application No. 60/901,332, filed on Feb. 15, 2007.

(30) Foreign Application Priority Data

Feb. 15, 2007  (GB) .................................... 0702990.3
Jul. 18, 2007  (GB) .................................... 0714036.1

(51) Int. Cl.
| A61K 39/395 | (2006.01) |
| C07K 16/28 | (2006.01) |
| G01N 33/68 | (2006.01) |
| A61K 45/06 | (2006.01) |
| A61K 39/00 | (2006.01) |

(52) U.S. Cl.
CPC ......... *C07K 16/2869* (2013.01); *A61K 39/3955* (2013.01); *C07K 2316/96* (2013.01); *C07K 2317/34* (2013.01); *C07K 2317/21* (2013.01); *A61K 2039/507* (2013.01); *G01N 33/6854* (2013.01); *A61K 2039/505* (2013.01); *G01N 33/6878* (2013.01); *A61K 45/06* (2013.01); *G01N 2333/59* (2013.01); *C07K 2317/565* (2013.01)
USPC ................. 424/143.1; 424/133.1; 530/388.22

(58) Field of Classification Search
None
See application file for complete search history.

(56) References Cited

U.S. PATENT DOCUMENTS

2011/0014200 A1 *  1/2011  Rapoport et al. ........... 424/139.1
2011/0300138 A1 * 12/2011  Rees-Smith et al. ........ 424/133.1

FOREIGN PATENT DOCUMENTS

| EP | 0719858 A2 * | 7/1995 |
| WO | WO 00/49050 | 8/2000 |
| WO | WO 02/08723 | 1/2002 |
| WO | WO 2004/050708 | 6/2004 |
| WO | WO 2006/016121 | 2/2006 |
| WO | WO 2008/091981 | 7/2008 |

OTHER PUBLICATIONS

Rudikoff et al., Single amino acid substitution altering antigen-binding specificity. Proc. Natl. Acad. Sci. USA, 79(6):1979-1983 (Mar. 1982).*
Portolano et al., Lack of Promiscuity in Autoantigen-Specific H and L Chain Combinations as Revealed by Human H and L Chain Roulette J. Immunol., vol. 150(3):880-887 (Feb. 1993).*
Clackson et al., Making antibody fragments using phage display libraries. Nature, vol. 352:624-628 (1991).*
Bendig M. M. Humanization of rodent monoclonal antibodies by CDR grafting. Methods: A Companion to Methods in Enzymology, vol. 8:83-93 (1995).*
Paul, W.E. Fundamental Immunology, Third Edition (textbook), "Fv Structure and Diversity in Three Dimensions" pp. 292-295; Raven Press, New York (1993).*
Casset et al. A peptide mimetic of an anti-CD4 monoclonal antibody by rational design. Biochem Biophys Res Comm. vol. 307:198-205 (2003).*
Davies, J. et al., "Affinity Improvement of Single Antibody VH Domains: Residues in all Three Hypervariable Regions Affect Antigen Binding", Immunotechnology, vol. 2, pp. 169-179 (1996).
Holt, L. et al., "Domain Antibodies: Proteins for Therapy", Trends in Biotechnology, Review, vol. 21, No. 11 (2003).
Kohn, L. et al., "Characterization of Monoclonal Thyroid-Stimulating and Thyrotropin Binding-Inhibiting Autoantibodies from Hashimoto's Patient Whose Children Had Intrauterine and Neonatal Thyroid Disease", Journal of Clinical Endocrinology and Metabolism, vol. 82, No. 12, pp. 3998-4009 (1997).
Sanders, J. et al., "Effects of TSH Receptor Mutations on Binding and Biological Activity of a Monoclonal Antibodies and TSH", Thyroid, vol. 16, No. 12 (2006).
Valente, W. et al., "Monoclonal Antibodies to the Thyrotropin Receptor: Stimulating and Blocking Antibodies Derived from the lymphocytes of Patients with Graves Disease", Proceedings of the National Academy of Sciences, USA, vol. 79, pp. 6680-6684 (1982).
Yoshida, T. et al., "Monoclonal Antibodies to the Thyrotropin Receptor Bind to a 56-kDa Subunit of Thyrotropin Receptor and Show Hetrogeneous Bioactivities", The Journal of Biological Chemistry, vol. 263, No. 31, pp. 16341-16347 (1988).

* cited by examiner

*Primary Examiner* — Elizabeth C Kemmerer
*Assistant Examiner* — Regina M DeBerry
(74) *Attorney, Agent, or Firm* — Hunton & Williams LLP

(57) ABSTRACT

The invention provides an isolated antibody for the TSHR which is an antagonist of TSH. The invention also relates to methods of using antibodies of the invention.

13 Claims, 8 Drawing Sheets gaagtgcagctggtggagtctggaggaggcctgatccagcctggggggtc cctgagactctcctgtgcagcctctggttcaccgtcagtagcaactaca    (SEQ ID NO: 7)

tgagctgggtccgccaggctccagggaaggggctggagtgggtctcagtt acttatagcggtggtagcacatcctacgcagactccgtgaagggccgatt caccatctccagagacaattccaagaacacgctgtatcttcaaatgaaca gcctgagagccgaggacacggccgtgtattactgtgcgagagggggcga tattgtagtagtataagctgctacgcgaggagcgggtgtgactactgggg ccagggaaccctggtcaccgtctcctcagcctccaccaagggcccatcgg tcttccccctggcaccctcctccaagagcacctctggggcacagcggcc ctgggctgcctggtcaaggactacttccccgaaccggtgacggtgtcgtg gaactcaggcgccctgaccagcggcgtgcacaccttcccggctgtcctac agtcctcaggactctactccctcagcagcgtggtgaccgtgccctccagc agcttgggcacccagacctacatctgcaacgtgaatcacaagcccagcaa caccaaggtggacaagagagttgagcccaaatcttgtgacaaaactagt

PCR primer

<u>gaagtgcagctggtggagtctggaggaggcctgatccagcctggggggtc</u>                50 cctgagactctcctgtgcagcctctggttcaccgtcagtCDR 1|agcaactaca|            100

|tgagc|tgggtccgccaggctccagggaaggggctggagtgggtctcaCDR 2|gtt|            150

|acttatagcggtggtagcacatcctacgcagactccgtgaagggc|gatt                200 caccatctccagagacaattccaagaacacgctgtatcttcaaatgaaca                250 gcctgagagccgaggacacggccgtgtattactgtgcgagaCDR 3|ggggggcga|            300

|tattgtagtagtataagctgctacgcgaggagcgggtgtgactac|gggg                350 ccagggaaccctggtcaccgtctcctcagconstant regioncctccaccaagggcccatcgg    400 tcttccccctggcaccctcctccaagagcacctctggggcacagcggcc                450 ctgggctgcctggtcaaggactacttccccgaaccggtgacggtgtcgtg                500 gaactcaggcgccctgaccagcggcgtgcacaccttcccggctgtcctac                550 agtcctcaggactctactccctcagcagcgtggtgaccgtgccctccagc                600 agcttgggcacccagacctacatctgcaacgtgaatcacaagcccagcaa                650 caccaaggtggacaagagagttgagcccaaatcttgtgacaaaactagt                699

(SEQ ID NO: 7)

FIG. 2A

(SEQ ID NO: 9)

EVQLVESGGGLIQPGGSLRLSCAASGFTVSSNYMSWVRQAPGKGLEWVSV

TYSGGSTSYADSVKGRFTISRDNSKNTLYLQMNSLRAEDTAVYYCARGGR

YCSSISCYARSGCDYWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKRVEPKSCDKTS

```
          PCR primer                 CDR 1              CDR 2
          EVQLVESGGGLIQPGGSLRLSCAASGFTVS SNYMS WVRQAPGKGLEWVS V          50
                                                        CDR 3
          TYSGGSTSYADSVKG RFTISRDNSKNTLYLQMNSLRAEDTAVYYCAR GGR            100
                              constant region
          YCSSISCYARSGCDY WGQGTLVTVSSASTKGPSVFPLAPSSKSTSGGTAA             150

LGCLVKDYFPEPVTVSWNSGALTSGVHTFPAVLQSSGLYSLSSVVTVPSS               200

SLGTQTYICNVNHKPSNTKVDKRVEPKSCDKTS                                233
```

(SEQ ID NO: 9)

FIG. 2B

(SEQ ID NO: 8)

gccatccagatgacccagtctccttcctccctgtctgcatctgtaggaga cagagtcaccatcacttgccgggcaagtcagagcattagcaactatttaa attggtatcagcagaaaccagggaaagcccctaagctcctgatctatgct gcatccagtttgcaaagtggggtcccatcaaggttcagtggcagtggatc tgggacagatttcactctcaccatcagcagtctgcaacctgaagattttg caacttactactgtcaacagagttacagttcccccctccaccacttttggc caggggaccaagctggagatcaaacgaactgtggctgcaccatctgtctt catcttcccgccatctgatgagcagttgaaatctggaactgcctctgttg tgtgcctgctgaataacttctatcccagagaggccaaagtacagtggaag gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgt

PCR primer
gccatccagatgacccagtctccttcctccctgtctgcatctgtaggaga    50
　　　　　　　　　　　　　　　　　　　　　　　　CDR 1
cagagtcaccatcacttgc cgggcaagtcagagcattagcaactatttaa    100
　　　　　　　　　　　　　　　　　　　　　　　　　　CDR 2
at tggtatcagcagaaaccagggaaagcccctaagctcctgatctat gct    150 gcatccagtttgcaaagt ggggtcccatcaaggttcagtggcagtggatc    200 tgggacagatttcactctcaccatcagcagtctgcaacctgaagattttg    250
　　　　　　　　　　　CDR 3
caacttactactgt caacagagttacagttcccccctccaccact tttggc    300
　　　　　　　　　　　　　　　　constant region
caggggaccaagctggagatcaaacga actgtggctgcaccatctgtctt    350 catcttcccgccatctgatgagcagttgaaatctggaactgcctctgttg    400 tgtgcctgctgaataacttctatcccagagaggccaaagtacagtggaag    450 gtggataacgccctccaatcgggtaactcccaggagagtgtcacagagca    500 ggacagcaaggacagcacctacagcctcagcagcaccctgacgctgagca    550 aagcagactacgagaaacacaaagtctacgcctgcgaagtcacccatcag    600 ggcctgagctcgcccgt    617

(SEQ ID NO: 8)

FIG. 3A

(SEQ ID NO: 10)
AIQMTQSPSSLSASVGDRVTITCRASQSISNYLNWYQQKPGKAPKLLIYA

ASSLQSGVPSRFSGSGSGTDFTLTISSLQPEDFATYYCQQSYSSPSTTFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSP

```
          PCR primer          CDR 1              CDR 2
    AIQMTQSPSSLSASVGDRVTITC[RASQSISNYLN]WYQQKPGKAPKLLIY[A]         50
                                                CDR 3
    [ASSLQS]GVPSRFSGSGSGTDFTLTISSLQPEDFATYYC[QQSYSSPSTT]FG          100
                  constant region
    QGTKLEIKRTVAAPSVFIFPPSDEQLKSGTASVVCLLNNFYPREAKVQWK          150

VDNALQSGNSQESVTEQDSKDSTYSLSSTLTLSKADYEKHKVYACEVTHQ          200

GLSSP                                                       205
```

(SEQ ID NO: 10)

FIG. 3B

|     |            |            |            |            |            |     |
|-----|------------|------------|------------|------------|------------|-----|
| 1   | MRPADLLQLV | LLLDLPRDLG | GMGCSSPPCE | CHQEEDFRVT | CKDIQRIPSL | PPSTQTLKLI | 60 |
| 61  | ETHLRTIPSH | AFSNLPNISR | IYVSIDVTLQ | QLESHSFYNL | SKVTHIEIRN | TRNLTYIDPD | 120 |
| 121 | ALKELPLLKF | LGIFNTGLKM | FPDLTKVYST | DIFFILEITD | NPYMTSIPVN | AFQGLCNETL | 180 |
| 181 | TLKLYNNGFT | SVQGYAFNGT | KLDAVYLNKN | KYLTVIDKDA | FGGVYSGPSL | LDVSQTSVTA | 240 |
| 241 | LPSKGLEHLK | ELIARNTWTL | KKLPLSLSFL | HLTRADLSYP | SHCCAFKNQK | KIRGILESLM | 300 |
| 301 | CNESSMQSLR | QRKSVNALNS | PLHQEYEENL | GDSIVGYKEK | SKFQDTHNNA | HYYVFFEEQE | 360 |
| 361 | DEIIGFGQEL | KNPQEETLQA | FDSHYDYTIC | GDSEDMVCTP | KSDEFNPCED | IMGYKFLRIV | 420 |
| 421 | VWFVSLLALL | GNVFVLLILI | TSHYKLNVPR | FLMCNLAFAD | FCMGMYLLLI | ASVDLYTHSE | 480 |
| 481 | YYNHAIDWQT | GPGCNTAGFF | TVFASELSVY | SSYAKVSICL | YAITFAMRLD | RKIRLRHACA | 540 |
| 541 | IMVGGWVCCF | LLALLPLVGI | PMDTETPLAL | FTDFICMAPI | AYIVFVLTLN | IVAFVIVCCC | 600 |
| 601 | YVKIYITVRN | PQYNPGDKDT | KIAKRMAVLI | FTKAFQRDVF | SFYALSAILN | KPLITVSNSK | 660 |
| 661 | ILLVLFYPLN | SCANPFLYAI | FTKAFQRDVF | ILLSKFGICK | RQAQAYRGQR | VPPKNSTDIQ | 720 |
| 721 | VQKVTHDMRQ | GLHNMEDVYE | LIENSHLTPK | KQGQISEEYM | QTVL       |            | 764 |

(SEQ ID NO: 11)

FIG. 4

HUMAN MONOCLONAL ANTIBODIES TO THE THYROTROPIN RECEPTOR WHICH ACT AS ANTAGONISTS

This application is the National Phase filing of International Application No. PCT/GB2008/000518, filed Feb. 14, 2008, which claims priority to Great Britain Patent Application No. GB 0702990.3, filed Feb. 15, 2007, to Great Britain Patent Application No. GB 0714036.1, filed Jul. 18, 2007, and to U.S. Provisional Patent Application No. 60/901,332, filed Feb. 15, 2007.

FIELD OF THE INVENTION

The present invention relates to antibodies which are reactive with the thyrotropin (TSH) receptor (TSHR), and in particular, though not exclusively, to antibodies which bind to the TSHR and which can block TSHR stimulation by TSH- or TSHR-stimulating antibodies.

BACKGROUND

Thyrotropin, or thyroid stimulating hormone (TSH), is a pituitary hormone that regulates thyroid function via the TSHR (Szkudlinski M W, Fremont V, Ronin C, Weintraub B D 2002 Thyroid-stimulating hormone and TSHR structure-function relationships. Physiological Reviews 82: 473-502). The TSHR is a G-protein coupled receptor and is composed of three domains:—a leucine rich domain (LRD), a cleavage domain (CD) and a transmembrane domain (TMD) (Nunez Miguel R, Sanders J, Jeffreys J, Depraetere H, Evans M, Richards T, Blundell T L, Rees Smith B, Furmaniak J 2004 Analysis of the thyrotropin receptor-thyrotropin interaction by comparative modelling. Thyroid 14: 991-1011). Binding of TSH to the TSHR triggers receptor signalling which leads to stimulation of formation and release of thyroid hormones; thyroxine (T4) and tri-iodothyronine (T3). A negative feedback mechanism involving the levels of T4 and T3 in the circulation controls the release of TSH from the pituitary (and thyrotropin releasing hormone secreted by the hypothalamus) that in turn controls thyroid stimulation and the levels of thyroid hormones in serum.

It is well documented in the art that some patients with autoimmune thyroid disease (AITD) have autoantibodies reactive with the TSHR (Rees Smith B, McLachlan S M, Furmaniak J 1988 Autoantibodies to the thyrotropin receptor. Endocrine Reviews 9: 106-121). In a majority of cases, these autoantibodies bind to the TSHR and mimic the actions of TSH thereby stimulating the thyroid to produce high levels of T4 and T3. These autoantibodies are described as thyroid stimulating autoantibodies or TSHR autoantibodies (TRAbs) with stimulating activity or TSH agonist activity. The physiological feedback mechanism of thyroid function control mentioned above is not effective in the presence of such thyroid stimulating autoantibodies and patients present with symptoms of thyroid hyperactivity or thyrotoxicosis (excess of thyroid hormones in serum). This condition is known as Graves' disease. In some patients, TRAbs with stimulating activity are thought to be responsible for interaction with TSHRs in retro-orbital tissues and to contribute to the eye signs of Graves' disease. A human monoclonal autoantibody which acts as a powerful thyroid stimulator (hMAb TSHR1) has been described in detail in patent application WO2004/050708A2.

In contrast in some patients with AITD, autoantibodies bind to the TSHR, prevent TSH from binding to the receptor but do not have the ability to stimulate the TSHR. These types of autoantibody are known as TRAbs with blocking activity or TSH antagonist activity, and patients who have blocking TRAbs in their serum may present with symptoms of an under-active thyroid (hypothyroidism) (Rees Smith B, McLachlan S M, Furmaniak J 1988 Autoantibodies to the thyrotropin receptor. Endocrine Reviews 9: 106-121). In particular, TRAbs with blocking activity when present in serum of pregnant women cross the placenta and may block foetal thyroid TSHRs leading to neonatal hypothyroidism and serious consequences for development. Furthermore, TRAbs with blocking activity can be found in breast milk of affected mothers and this may contribute further to clinical hypothyroidism in the baby. To date human monoclonal autoantibodies to the TSHR with TSH antagonist activity have not been available. Consequently, detailed studies of how this type of autoantibody interacts with the TSHR, and how their interactions with the TSHR compare with those of stimulating type of autoantibodies (such as M22) and with TSH, have been limited.

Human chorionic gonadotropin is a hormone produced during pregnancy which has mild thyroid stimulating effects.

Characterisation of the properties of TRAbs with stimulating or blocking activities is of critical importance in studies which aim to improve the diagnosis and management of diseases associated with an autoimmune response to the TSHR. The invention described in patent application WO2004/050708A2 provides details about the properties of a human monoclonal autoantibody with powerful stimulating activity and its interaction with the TSHR. Furthermore, patent application WO2006/016121A discloses a mutated TSHR preparation including at least one point mutation which can be used in the differential screening and identification of patient serum stimulating TSHR autoantibodies, patient serum blocking TSHR autoantibodies and TSH in a sample of body fluid from a patient being screened. Patent application WO2004/050708A2 also describes a mouse monoclonal antibody (9D33) with TSHR blocking activity. 9D33 binds to the TSHR with high affinity ($2 \times 10^{10}$ L/mol) and is an effective antagonist of TSH, hMAb TSHR1 (M22) and patient serum TRAbs with stimulating or blocking activities (patent application WO2004/050708A2 and Sanders J, Allen F, Jeffreys J, Bolton J, Richards T, Depraetere H, Nakatake N, Evans M, Kiddie A, Premawardhana L D, Chirgadze D Y, Miguel R N, Blundell T L, Furmaniak J, Rees Smith B 2005 Characteristics of a monoclonal antibody to the thyrotropin receptor that acts as a powerful thyroid-stimulating autoantibody antagonist. Thyroid 15: 672-682). Although the mouse monoclonal antibody 9D33 shows at least some of the characteristics of patient serum TRAbs with blocking activity, it is a mouse antibody generated by immunisation of an experimental animal with the TSHR and as such may not be truly representative of TSHR autoantibodies generated in the process of an autoimmune response to the TSHR in humans. As a mouse monoclonal antibody, 9D33 would need to be humanised for in vivo applications in humans. This may be disadvantageous in view of the expense and complication involved in the humanisation process.

The present invention results from the production and properties of a human monoclonal autoantibody (5C9) to the TSHR that is an effective antagonist of TSH and of stimulating TRAbs in patient sera. 5C9 has been isolated from the peripheral lymphocytes of a patient with hypothyroidism and high levels of TSHR autoantibodies. The lymphocytes were immortalised by infection with Epstein Barr virus (EBV) and positive clones fused with a mouse/human cell line to generate a stable clone. IgG was purified from supernatants of clone cultures and the ability of 5C9 IgG to bind to the TSHR and influence TSHR activity was assessed. In particular, the ability of 5C9 to inhibit TSH binding to the TSHR, and to inhibit cyclic AMP stimulating activity of TSH was studied. Furthermore, the ability of 5C9 to inhibit binding of stimulating or blocking patient serum TRAbs to the TSHR and to inhibit their biological activity was also assessed. In addition, the use of 5C9 in assays for TSHR antibodies, TSH and related compounds was investigated. Variable region (V region) genes of the heavy (HC) and light chains (LC) of 5C9 were sequenced and the complementarity determining regions (CDRs) assigned.

SUMMARY OF THE INVENTION

According to a first aspect of the invention there is provided an isolated human antibody for the TSHR which is an antagonist of TSH.

According to second aspect of the invention there is provided an isolated humanised antibody for the TSHR which is an antagonist of TSH.

An antibody according to either the first or second aspect of the invention is "an antibody according to the invention".

An antibody according to the invention may be an antagonist of thyroid stimulating antibodies.

An antibody according to the invention may have the TSH antagonist characteristics of patient serum TSHR autoantibodies which are TSH antagonists.

An antibody according to the invention may be an antagonist of TSH and an antagonist of thyroid stimulating antibodies.

An antibody according to the invention may have the antagonistic characteristics of patient serum TSHR autoantibodies which are antagonists of thyroid stimulating antibodies.

An antibody according to the invention may be an inhibitor of binding to TSHR or a portion thereof by TSH, by M22, or antibodies with stimulating activity or antibodies with blocking activity to the TSHR. A TSHR portion may include the LRD or a substantial portion thereof. Preferably, an antibody which prevents such binding.

An antibody according to the invention may be a monoclonal or recombinant antibody, or comprise or consist of a fragment thereof which is an antagonist of TSH. An antibody according to the invention may comprises a $V_H$ region which comprises one or more CDRs selected from CDR 1, CDR 2, or CDR 3, shown in FIG. 2, or one or more amino acid sequences having substantial homology to those CDRs. Additionally or alternatively, an antibody according to the invention may comprise a $V_L$ region which comprises one or more CDRs selected from CDR 1, CDR 2, or CDR 3 shown in FIG. 3, or one or more amino acid sequences having substantial homology to those CDRs.

An antibody according to the invention may have a binding affinity for human full length TSHR of about $10^{10}$ L/mol. Preferably an antibody according to the invention has a binding affinity for human full length TSHR of about $10^9$ L/mol.

The invention helps the skilled addressee to understand the immunological mechanisms which drive development and production of stimulating and blocking TSHR autoantibodies. Additionally, the invention helps the skilled addressee to understand molecular differences between TSHR autoantibodies with thyroid stimulating activity and with blocking activity. In addition, the method of medical treatment and pharmaceutical compositions of the invention provide new treatments for thyroid-related conditions.

A preferred antibody in accordance with the invention is 5C9. 5C9, has been found unexpectedly to inhibit thyroid stimulating hormone receptor constitutive activity, that is to say the production of cyclic AMP in a test system in the absence of thyroid stimulating hormone or M22. This may be particularly advantageous in the treatment of thyroid cancer cells remaining in the thyroid, or in metastases, especially in preventing or delaying regrowth as those cells will grow more rapidly as a consequence of thyroid stimulating hormone receptor constitutive activity.

The term "antibody" and cognate terms, such as "antibodies", used herein embraces according to context immunoglobulin-based binding moieties such as monoclonal and polyclonal antibodies, single chain antibodies, multi-specific antibodies and also binding moieties, which may be substituted by the skilled addressee for such immunoglobulin-based binding moieties, such as domain antibodies, diabodies, IgG$\Delta$C$_H$2, F(ab')$_2$, Fab, scFv, $V_L$, $V_H$, dsFv, Minibody, Triabody, Tetrabody, (scFv)$_2$, scFv-Fc, F(ab')$_3$ (Holliger P, Prospero T, Winter G 1993 "Diabodies: small bivalent and bispecific antibody fragments" Proc Natl Acad Sci USA 90: 6444-6448.), (Carter P J 2006 "Potent antibody therapeutics by design" Nat Rev Immunol 6: 343-357).

The term "TSHR" refers to full length human thyroid stimulating hormone receptors having the amino acid sequence shown in FIG. 4 or variants or fragments thereof having high homology with thyroid stimulating hormone receptors. Preferably, such variants and fragments having 70 to 99.9% homology with amino acid sequence shown in FIG. 4.

According to another aspect of the invention there is provided a nucleotide comprising:

a) a nucleotide sequence encoding an antibody according to the first aspect of the invention;

b) a nucleotide sequence as shown in FIG. 2 or 3 encoding an amino acid sequence of an antibody $V_H$ domain, an antibody $V_L$ domain, or a CDR as shown in FIG. 2 or 3; or c) a nucleotide sequence having high homology to nucleotide sequences of a) or b) and encoding an antibody which binds to TSHR with an affinity of at least about $10^9$ L/mol.

According to another aspect of the invention there is provided a vector comprising a nucleotide according to the above aspect of the invention.

The vector may be a plasmid, virus or fragment thereof. Many different types of vectors are known to the skilled addressee.

According to another aspect of the invention there is provided an isolated cell including an antibody; nucleotides or/vector according to the invention. The isolated cell may express an antibody according to the invention. Preferably, the isolated cell secretes an antibody according to the invention. Preferably an isolated cell according to the invention is from a stable hetero-hybridoma cell line.

According to a further aspect of the invention there is provided a composition comprising a defined concentration of TSHR autoantibodies and including an antibody according to the invention. Such a composition may comprise a defined concentration of TSHR autoantibodies with TSH antagonist activity, and includes an antibody according to the invention.

Alternatively, a composition according to this aspect of the invention may comprise a defined concentration of TSHR autoantibodies which are antagonists of thyroid stimulating antibodies, and includes an antibody according to the invention. A composition may comprise a defined concentration of TSHR autoantibodies with TSH antagonist activity and which are antagonists of thyroid stimulating antibodies, and includes an antibody according to the invention.

According to another aspect of the invention there is provided a pharmaceutical composition for administration to a mammalian subject for the treatment of a thyroid-related condition comprising an antibody according to the invention, together with a pharmaceutically acceptable carrier. The thyroid-related condition may be selected from thyroid overactivity, Graves' eye disease, neonatal hyperthyroidism, human chorionic gonadotrophin-induced hyperthyroidism, pre-tibial myxoedema, thyroid cancer and thyroiditis.

A pharmaceutical composition according to the invention may be suitable for human administration. Preferably a pharmaceutical composition according to the invention has no significant adverse effect on the immune system of the subject.

A pharmaceutical composition according to the invention may include an additional thyroid stimulating hormone receptor antagonist. A suitable additional thyroid stimulating hormone receptor antagonist is 9D33 as disclosed in WO2004/050708.

Various formats are contemplated for pharmaceutical compositions according to the invention. A pharmaceutical composition according to the invention for use in the treatment of a thyroid-related condition may be in an injectable format. A pharmaceutical composition according to the invention for use in the treatment of pre-tibial myxoedema is preferably in a topical format. A pharmaceutical composition according to the invention for use in the treatment of Graves' eye disease is preferably in the form of eye drops.

Pharmaceutical compositions of this invention comprise any antibody in accordance with the invention of the present invention, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention may be administered orally, parenterally, by inhalation spray, topically, by eyedrops, rectally, nasally, buccally, vaginally or via an implanted reservoir. We prefer oral administration or administration by injection. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

According to a further aspect of the invention there is provided a method of producing an antibody according to the invention, the method comprising culturing one or more isolated cells according to the invention whereby the antibody is expressed by the cell. Preferably, the antibody is secreted by the cell.

According to a further aspect of the invention there is provided a method of treating a thyroid-related condition in a mammalian subject, or in cells derived from the subject, the method comprising contacting the subject, or the cells, with an antibody according to the invention.

According to another aspect of the invention there is provided a method of inhibiting thyroid stimulating autoantibodies stimulating the TSHR in the thyroid of a mammalian subject, the method comprising contacting the subject with an antibody according to the invention. Preferably binding of thyroid stimulating autoantibodies to the TSHR is prevented.

According to another aspect of the invention there is provided a method of inhibiting thyroid stimulating autoantibodies binding to extra-thyroidal TSHRs in a mammalian subject, the method comprising contacting the subject with an antibody according to the invention. The extra-thyroidal TSHRs may be in retro-orbital tissues and/or pre-tibial tissue of the subject. The antibody of the invention preferably blocks TSHR autoantibodies binding to extra-thyroidal TSHRs when used in the method.

According to another aspect of the invention there is provided a method of treating thyroid cancer in the thyroid, or in metastases, in a subject or in thyroid cells derived from a subject, the method comprising contacting the cancerous cells with an antibody according to the invention, in order to inhibit constitutive thyroid stimulating hormone receptor activity in the cells. Preferably regrowth of thyroid cancer cells is prevented or delayed.

There is also provided a method of treating thyroid overactivity due to constitutive thyroid activity, in a subject or in thyroid cells derived from a subject, the method comprising contacting the subject or thyroid cells with an antibody according to the invention, in order to inhibit thyroid overactivity due to constitutive thyroid activity.

The subject treated in the various methods of the invention described above is preferably human.

According to another aspect of the invention there is provided the use of an antibody according to the invention in the treatment of a thyroid-related condition. Alternatively there is provided the use of an antibody according to the invention in the preparation of a medicament for the treatment of a thyroid-related condition.

There is also provided an antibody according to the invention for use in medical therapy. In particular, there is provided the use of an antibody according to the invention for use in the treatment of a thyroid-related condition. The thyroid-related condition may be selected from thyroid overactivity, Graves' eye disease, neonatal hyperthyroidism, human chorionic gonadotrophin-induced hyperthyroidism, pre-tibial myxoedema, thyroid cancer and thyroiditis.

According to another aspect of the invention there is provided a method of characterising TSHR antibodies comprising determining binding of a TSHR antibody under test to a polypeptide having a TSHR-related amino acid sequence in which the method involves a method step including the use of an antibody according to the invention. Preferably the method comprises determining the effects of an antibody according to the invention on binding of a TSHR antibody to that polypeptide. The polypeptide having a TSHR-related amino acid sequence preferably comprises full length human TSHR.

According to another aspect of the invention there is provided a method for characterising TSH and related molecules, comprising determining binding of TSH, or a related molecule under test, to a polypeptide having a TSHR-related amino acid sequence, in which the method involves a method step including the use of an antibody according to the invention.

Methods for characterising TSHR antibodies, or TSH and related methods described above may be in an ELISA format.

According to another aspect of the invention there is provided a method of determining TSHR amino acids involved in binding TSHR autoantibodies which act as antagonists, the method comprising providing a polypeptide having a first TSHR-related amino acid sequence to which an antibody according to the invention binds, modifying at least one amino acid in the TSHR-related amino acid sequence and determining the effect of such modification on binding of the antibody.

A method of modifying an antibody according to the invention, the method comprising modifying at least one amino acid of the antibody and determining an effect of such a modification on binding to a TSHR-related sequence. Preferably modified TSHR antibodies are selected which have an enhanced affinity for the TSHR.

According to another aspect of the invention there is provided a method of identifying molecules which inhibit thyroid stimulating antibodies binding to the TSHR, the method comprising providing at least one antibody according to the invention as reference. Preferably molecules under test which prevent thyroid stimulating antibodies binding to the TSHR are selected.

There is also provided a method of identifying molecules which inhibit thyroid blocking antibodies binding to the TSHR, the method comprising providing at least one antibody according to the invention as reference. Preferably molecules which prevent thyroid blocking antibodies binding to TSHR are selected.

BRIEF DESCRIPTION OF THE DRAWINGS

Antibodies and methods in accordance with the invention will now be described, by way of example only, with reference to the accompanying drawings, FIGS. 1 to 4, in which.

Figure 1A:
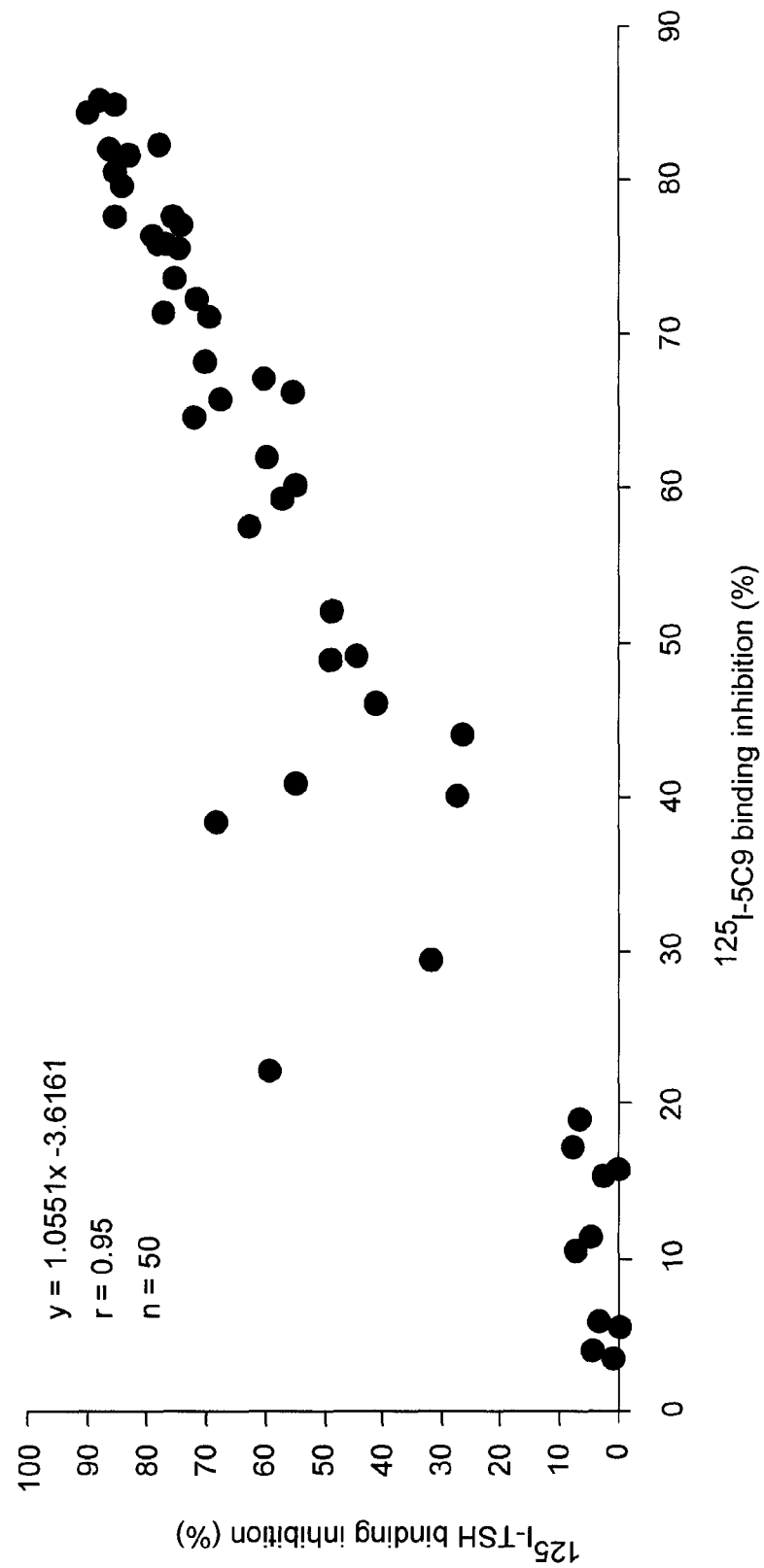
FIG. 1 is a series of three graphs illustrating a comparison of the effects of sera from patients with Graves' disease (n=40) and healthy blood donors (n=10) on $^{125}$I-5C9 IgG, $^{125}$I-TSH or $^{125}$I-M22 binding to TSHR coated tubes.

a $^{125}$I-5C9 IgG vs $^{125}$I-TSH binding
    b $^{125}$I-5C9 IgG vs $^{125}$I-M22 IgG binding
    c $^{125}$I-TSH vs $^{125}$I-M22 IgG binding;

FIG. 2 gives sequences of the variable region sequences of 5C9 heavy chain (HC)
    a the oligonucleotide sequence of 5C9 HC shown in unannotated and annotated forms. In the annotated forms, sequences used for PCR primers are individual Complementarity Determining Regions (CDRs) are boxed; and constant regions are bold.
    b the amino acid sequence of 5C9 HC derived from the oligonucleotide sequence shown in unannotated and annotated forms;

FIG. 3 gives sequences of the variable region sequences of 5C9 light chain (LC):
    a the oligonucleotide sequence of 5C9 LC shown in unannotated and annotated (as per FIG. 2) forms
    b the amino acid sequence of 5C9 LC derived from the oligonucleotide sequence shown in unannotated and annotated forms; and FIG. 4 illustrates the consensus amino acid sequence of the human TSHR (accession no. P16473).

DETAILED DISCLOSURE

Methods
Lymphocyte Isolation and Cloning of the Human Monoclonal TSHR Autoantibody 5C9

The monoclonal autoantibody 5C9 was isolated generally using the procedure described in WO2004/050708A2. Lymphocytes were first isolated from a blood sample collected from a patient with postpartum hypothyroidism and high levels of TRAbs (Local Ethical Committee approval was obtained). The lymphocytes were infected with Epstein Barr Virus (EBV) (European Collection of Cell Cultures—ECACC; Porton Down, SP4 0JG,UK) and cultured on mouse macrophage feeder layers as described in WO2004/050708A2. Immortalised lymphocytes secreting TSHR autoantibodies were fused with a mouse/human hybrid cell line K6H6/B5 (ECACC) and cloned four times by limiting dilution to obtain a single colony. The presence of TSHR autoantibody in cell culture supernatants at different stages of cloning was detected by inhibition of $^{125}$I-labelled TSH binding to the TSHR (WO2004/050708A2). A single clone producing the TSHR autoantibody was expanded and supernatants from the cultures were harvested for autoantibody purification.

Purification and Labelling of 5C9 IgG Preparations

5C9 IgG was purified from culture supernatants using protein A affinity chromatography on MabSelect™ (GE Healthcare, UK) as described in Sanders J, Jeffreys J, Depraetere H, Evans M, Richards T, Kiddie A, Brereton K, Premawardhana L D, Chirgadze D Y, Nunez Miguel R, Blundell T L, Furmaniak J, Rees Smith B 2004 Characteristics of a human monoclonal autoantibody to the thyrotropin receptor: sequence structure and function. Thyroid 2004 14: 560-570) and purity assessed by SDS-polyacrylamide gel electrophoresis (PAGE).

The heavy chain isotype of 5C9 was determined using a radial diffusion assay (The Binding Site; Birmingham, B29 6AT, UK), and the light chain isotype was determined by Western blotting with anti-human kappa chain and anti-human lambda chain specific mouse monoclonal antibodies (Sigma-Aldrich Company Ltd, Poole, UK).

5C9 IgG at 10 mg/mL in 20 mmol/L sodium acetate pH 4.5 was incubated with immobilized pepsin prepared according to the manufacturer's instructions (Perbio Science UK Ltd, Cramlington, UK) for 4½ hours at room temperature with shaking. Thereafter, immobilised pepsin was removed by centrifugation (1000×g, 5 minutes at room temperature) and the supernatant dialysed against 300 mmol/L NaCl, 10 mmol/L Tris-HCl pH 7.5 overnight at 4° C. The dialysed mixture containing 5C9 F(ab')2 and small amounts of intact IgG was separated using a Sephacryl S-300 High Resolution Matrix (GE Healthcare, Chalfont St Giles, UK). The 5C9 F(ab')$_2$ preparations purified in this way did not contain intact IgG as judged by SDS-PAGE and HPLC gel filtration analyses.

Furthermore, F(ab')$_2$ was reduced using a final concentration of 100 mmol/L L-cysteine for 1 hour at 37° C. The reaction was stopped with a final concentration of 50 mmol/L iodoacetamide for 30 minutes at room temperature. The F(ab') was purified using a Sephacryl S-300 column as above. F(ab') preparations purified in this way did not contain F(ab')$_2$ as judged by SDS-PAGE and HPLC gel filtration analysis.

In addition, 5C9 IgG was treated with mercuripapain (Sigma, UK) at an enzyme/protein ratio of 1:100 dialysed into 50 mmol/L NaCl, Tris-HCl pH 9.0 and passed through an anion exchange Sepharose (Q-Sepharose Fast flow from GE Healthcare) column to separate intact IgG or Fc from the Fab preparation. Analysis by SDS-PAGE and gel filtration (Sephacryl S-300 column; as above) indicated that intact IgG was undetectable in the Fab preparation.

5C9 IgG was labelled with $^{125}$I as described in Sanders J, Oda Y, Roberts S, Kiddie A, Richards T, Bolton J, McGrath V, Walters S, Jaskolski D, Furmaniak J, Rees Smith B 1999. The interaction of TSH receptor autoantibodies with $^{125}$I-labelled TSH receptor. Journal of Clinical Endocrinology and Metabolism. 1999 84: 3797-3802) or with biotin hydrazide (Perbio Science, Cramlington, UK).

Inhibition of $^{125}$I-TSH or $^{125}$I-M22 or $^{125}$I-5C9 Binding to the TSHR Binding inhibition assays were carried out using TSHR coated tubes as described in WO2004/050708A2. In the assay, 100 µL of test sample (MAb preparation, patient serum or unlabelled TSH) and 50 µL of start buffer (RSR Ltd) were incubated in TSHR coated tubes for 2 hours at room temperature with gentle shaking. After aspiration, the tubes were washed and 100 µL of $^{125}$I-labelled protein (5×10$^4$ cpm) added and incubated for 1 hour at room temperature with shaking. The tubes were then aspirated, washed and counted in a gamma counter.

Inhibition of labelled protein binding was calculated as:—

$$100 \times \left[1 - \frac{cpm \text{ bound in the presence of test material}}{cpm \text{ bound in the presence of control material}}\right]$$

Control material was a pool of healthy blood donor sera or individual healthy blood donor sera or other materials as indicated in the results of various experiments.

Scatchard Analysis of 5C9 IgG Binding to the TSHR

Unlabelled 5C9 IgG in 50 µL of assay buffer (50 mmol/L NaCl, 10 mmol/L Tris pH 7.8 and 1% Triton X-100) and 50 µL of $^{125}$I-labelled 5C9 IgG (30,000 cpm in assay buffer) were incubated in TSHR coated tubes for 2 hours at room temperature with shaking (maximum binding occurred under these conditions), aspirated, washed twice with 1 mL of assay buffer and counted in a gamma counter. The concentration of IgG bound vs bound/free was plotted (Scatchard G 1949 The attraction of proteins for small molecules and ions. Annals of the New York Academy of Sciences 51: 660-672) to derive the association constant.

Analysis of Stimulation of Cyclic AMP Production

The ability of 5C9 IgG and other preparations to stimulate production of cyclic AMP in Chinese hamster ovary (CHO) cells transfected with the human TSHR was tested as described in WO2004/050708A2. CHO cells expressing either approximately 5×10$^4$ or approximately 5×10$^5$ TSHR per cell were seeded into 96-well plates at 3×10$^4$ cells per well, adapted into DMEM (Invitrogen Ltd, Paisley, UK) without foetal calf serum and then test samples (TSH, IgG or patient serum) added (100 µL diluted in cyclic AMP assay buffer i.e. NaCl free Hank's Buffered Salts solution containing 1 g/L glucose, 20 mmol/L HEPES, 222 mmol/L sucrose, 15 g/L bovine serum albumin and 0.5 mmol/L 3 isobutyl-1-methylxanthine pH 7.4) and incubated for 1 hour at 37° C. After removal of test solutions, cells were lysed and cyclic AMP concentration in the lysates assayed by one of two methods: 1) using a Biotrak enzyme immunoassay system from GE Healthcare, Chalfont St Giles, UK; or 2) using Direct Cyclic AMP Correlate—EIA kits from Assay Designs; Cambridge Bioscience, UK. Results are expressed as pmol/mL of cyclic AMP in the cell lysate (200 µl) or as fmol per cell well.

Measurement of Antagonist (Blocking) Activity

The ability of 5C9 IgG and other preparations to inhibit the stimulating activity of porcine (p) TSH, native human (h) TSH and recombinant human (rh) TSH, MAb M22 and patient serum TRAbs in CHO cells expressing TSHRs was assessed. This was carried out by comparing the stimulatory effect of TSH, M22 or TRAbs in the absence and in the presence of 5C9 IgG (or other preparations being tested). The assay was carried out as described above except 50 μL of 5C9 (or other preparations being tested) diluted in cyclic AMP assay buffer was added to the cell wells followed by 50 μL of TSH or M22 or patient serum (diluted as appropriate in cyclic AMP assay buffer) and incubated and tested as for the stimulating assay described above.

Other MAbs and sera from patients with blocking type TRAbs were tested in this assay in addition to 5C9.

Variable Region Gene Analysis

The variable region genes of the 5C9 heavy and light chains were determined as described in WO2004/050708A2, using total RNA prepared from $1 \times 10^7$ hetero-hybridoma cells secreting 5C9 IgG to produce mRNA for RT-PCR (reverse transcriptase PCR) reactions. Specific IgG1 HC and kappa LC sense and antisense strand oligonucleotide primers were designed using the Medical Research Council's V-base and synthesised by Invitrogen (Paisley, PA4 9RF, UK). The RT reaction was carried out at 50° C. for 15 minutes followed by 40 cycles of PCR at 94° C. for 15 seconds, 50° C. for 30 seconds and 72° C. for 30 seconds. DNA products were cloned into pUC18 and sequenced by the Sanger-Coulson method (Sanger F, Nicklen S, Coulson AR 1977 DNA sequencing with chain terminating inhibitors. Proceedings of the National Academy of Sciences of USA 74: 5463-5467). V region sequences were compared with available sequences of human Ig genes using Ig blast.

Analysis of the Effects of Amino Acid Mutations in the Human TSHR Sequence on 5C9 Activity.

The methods used to introduce specific mutations into the TSHR sequence have been described in patent application WO2006/016121A. Furthermore, the transfection of mutated TSHR constructs into CHO cells using the Flp-In system is also described in WO2006/016121A.

Flp-In-CHO cells expressing either wild type or mutated TSHRs were seeded into 96 well plates and used to test the ability of 5C9 preparations to block the stimulating activity of TSH, M22 or patient serum TRAbs as described above.

5C9 Based Assays for TSHR Antibodies, TSH and Related Molecules.

5C9 IgG at 2.55 mg/mL was dialysed into 100 mmol/L sodium phosphate buffer pH 8.5 and reacted with EZ-Link NHS-LC-Biotin (Perbio) using a molar ratio of IgG to biotin of 1/10. Test serum samples (75 μL) were incubated in TSHR-coated ELISA plate wells (RSR Ltd) for 2 hours at room temperature with shaking (500 shakes per minute). After removing the test samples and washing, biotin labelled 5C9 IgG (2 ng in 100 μL) was added and incubation continued for 25 min at room temp without shaking. The wells were emptied, washed and 100 μL streptavidin-peroxidase (10 ng in 100 μL; RSR Ltd) was added and incubated for 20 min at room temperature without shaking. The wells were then washed three times, the peroxidase substrate tetramethyl benzidine (TMB; 100 μL; RSR Ltd) was added and incubated for 30 minutes at room temperature in the dark without shaking. 50 μL of 0.5 mol/L H2SO4 was then added to stop the reaction and the absorbance of each plate well was read at 450 nm using an ELISA plate reader. Inhibition of 5C9 IgG-biotin binding was calculated as:—

$$100\times\left[1-\frac{\text{test sample absorbance at 450 nm}}{\text{negative control serum absorbance at 450 nm}}\right]$$

Results

Isolation and Cloning of the 5C9 Secreting Cell Line

Lymphocytes ($27\times10^6$) obtained from 20 mL of patient's blood were infected with EBV and plated out at $1\times10^6$ cells per well in a 48 well plate on feeder layers of mouse macrophages. On day 13 post EBV infection the plate well supernatants were monitored for inhibition of $^{125}$I-TSH binding. Cells from the positive wells were expanded and fused with the K6H6/B5 hybridoma cell line and plated out in 96 well plates. One clone stably producing antibody with $^{125}$I-TSH binding inhibiting activity was obtained and re-cloned 4 times. The monoclonal antibody, designated as 5C9, purified from hetero-hybridoma culture supernatants was subclass IgG1 with kappa light chains.

TSHR Binding and Blocking Activities of 5C9 IgG

The ability of different concentrations of 5C9 IgG to inhibit binding of labelled TSH or labelled M22 or labelled 5C9 itself to the TSHR is shown in Table 1. As shown in Table 1, 12% inhibition of $^{125}$I-TSH binding was observed with as little as 0.005 μg/mL of 5C9 IgG and the inhibition increased in a dose dependent manner up to 84% inhibition at 100 μg/mL of 5C9. This can be compared to $^{125}$I-TSH binding inhibition by donor serum IgG; 13% inhibition at 0.05 mg/mL increasing in a dose dependent manner to 94% inhibition at 1 mg/mL. In the case of donor plasma, 16% inhibition of $^{125}$I-TSH binding was observed at 1:160 dilution in healthy blood donor pool serum and 95% inhibition at 1:10 dilution.

5C9 IgG also had an effect on binding of $^{125}$I-M22 IgG to the TSHR coated onto the tubes (Table 1). 9% inhibition of $^{125}$I-M22 IgG binding was observed at 0.01 μg/mL of 5C9 IgG and increasing concentrations resulted in a dose dependent increase of inhibition up to 85% at 100 μg/mL. Donor serum IgG was effective at 0.01 mg/mL causing 9% inhibition and the effect increased in a dose dependent manner to 89% inhibition at 1 mg/mL. Donor serum plasma showed 13% inhibition of $^{125}$I-M22 IgG binding at 1:320 dilution and 91% inhibition at 1:10 dilution.

Unlabelled 5C9 IgG was able to inhibit $^{125}$I-5C9 binding to the TSHR coated tubes in a dose dependent manner (11% inhibition at 0.005 μg/mL up to 88% inhibition at 100 μg/mL) (Table 1). Binding of $^{125}$I-5C9 was also inhibited by donor serum IgG (15% inhibition at 0.05 mg/mL and 91% inhibition at 1 mg/mL) as well as dilutions of donor plasma (10% inhibition at 1:320 dilution and 92% at 1:10 dilution).

The ability of 5C9 IgG to block TSH and M22-mediated stimulation of cyclic AMP in CHO cells expressing the TSHR is shown in Tables 2a-c. Porcine TSH (3 ng/mL) strongly stimulated cyclic AMP production (19,020±2154 fmol/cell well; mean±SD; n=3) (Table 2a). In the presence of 0.1 μg/mL of 5C9 IgG the stimulating activity of porcine TSH was reduced to 11874±4214 fmol/cell well (mean±SD; n=3) and the inhibiting effect was dependent on 5C9 concentration with only 2,208±329 fmol/cell well of cyclic AMP produced in the presence of 1 μg/mL of 5C9 (Table 2a). The lymphocyte donor serum also had a strong inhibiting effect on TSH mediated cyclic AMP stimulation in CHO-TSHR cells. As shown in Table 2a, inhibition of cyclic AMP production down to approximately 6000 Enol/cell well occurred in the presence of donor serum at 1:10 dilution (total serum IgG concentration at this dilution of 1.43 mg/mL) compared to 19000 fmol/cell well in the absence of serum. This effect corresponded to the effect of approximately 0.37 μg/mL of purified 5C9 IgG (calculated from the dilution curve of the effect of different concentrations of 5C9 IgG shown in Table 2a). This indicates that purified 5C9 IgG is approximately 3900 times more active than the donor serum IgG in terms of ability to block the ability of TSH to stimulate cyclic AMP production.

Fragments of 5C9, such as 5C9 F(ab')$_2$ and 5C9 Fab were also effective inhibitors of TSH stimulation. In particular, TSH stimulation inhibiting activity of 5C9 IgG, 5C9 F(ab')$_2$ and 5C9 Fab at 100 μg/mL were the same (Table 2b). At 10 μg/mL all three preparations: 5C9 IgG, 5C9 F(ab')$_2$ and 5C9 Fab were also potent inhibitors of TSH stimulating activity, however, 5C9 IgG appeared to be more effective than 5C9 F(ab')$_2$ or 5C9 Fab (Table 2b).

M22 Fab (3 ng/mL) is a potent stimulator of cyclic AMP (9,432±822 fmol/cell well) (Table 2c) and in the presence of 5C9 the stimulating effect of M22 Fab was inhibited in a dose dependent manner, with cyclic AMP levels reduced to 1,298±134 fmol/cell well in the presence of 0.1 μg/mL of 5C9 IgG. Complete inhibition of M22 stimulation occurred at 100 μg/mL of 5C9 (Table 2c).

Scatchard analysis indicated that $^{125}$I-labelled 5C9 bound to the TSHR with an association constant of 4×10$^{10}$ L/mol.

Inhibition of $^{125}$I-5C9 IgG Binding to the TSHR by Serum TRAbs

The ability of serum TRAbs to inhibit $^{125}$I-5C9 IgG binding to TSHR coated tubes is shown in Table 3 and FIG. 1. The effect of the same serum TRAbs on binding of $^{125}$I-TSH and binding of $^{125}$I-M22 IgG is also shown for comparison.

Figure 1B:
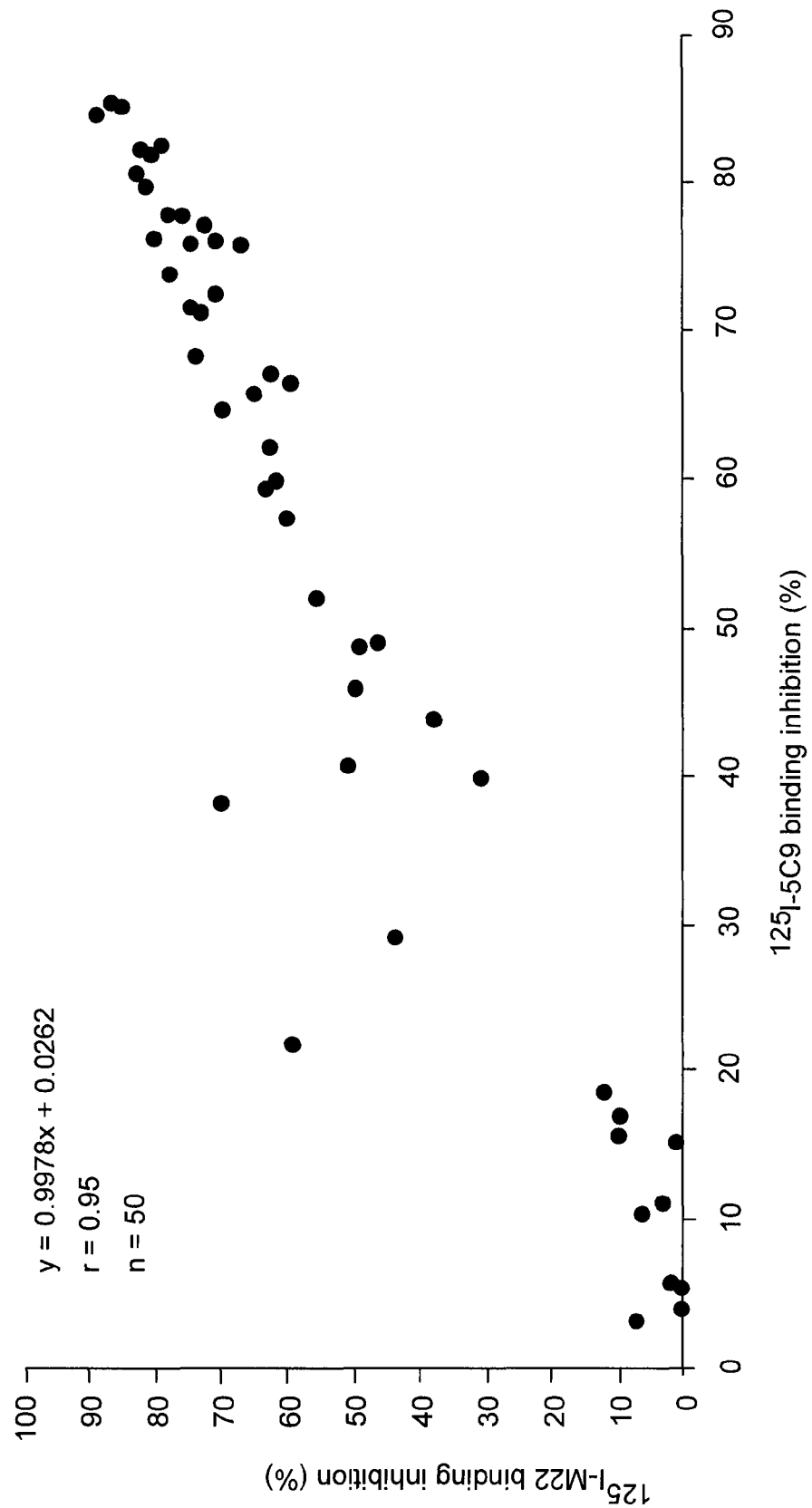
Figure 1C:
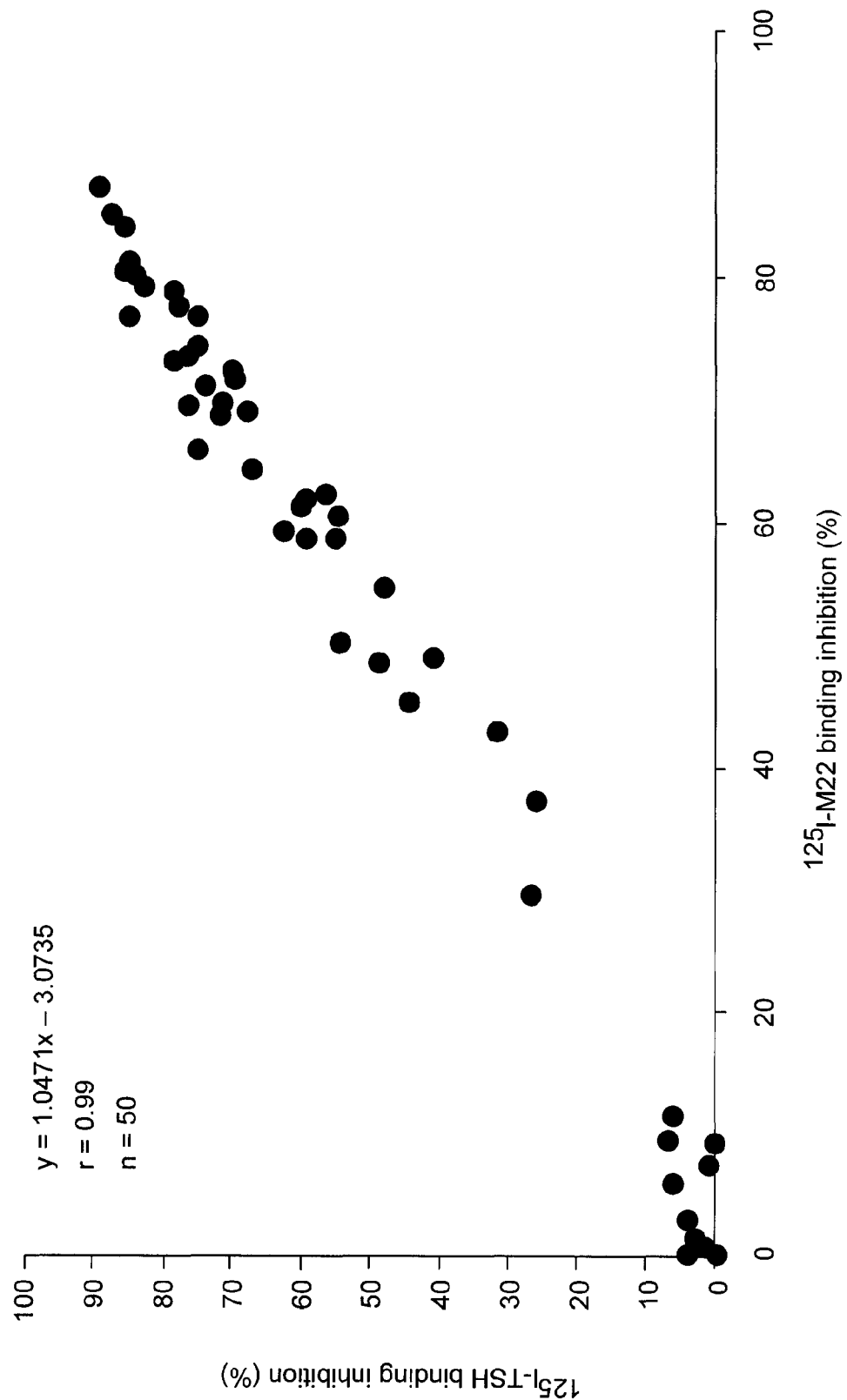

Binding of $^{125}$I-5C9 IgG to the TSHR was not markedly inhibited (inhibition range 3.4-18.9%) by sera from 10 different healthy blood donors (N1-N10, Table 3). Sera from 40 patients with Graves' disease (G1-G40, Table 3) all positive for TSHR autoantibodies in $^{125}$I-TSH and $^{125}$I-M22 inhibition assays (Table 3) inhibited $^{125}$I-5C9 binding to TSHR coated tubes (inhibition range 22.0-85.2%) to a greater extent than sera from healthy blood donors (Table 3). The ability of patient serum TRAbs to inhibit $^{125}$I-5C9 IgG, $^{125}$I-TSH or $^{125}$I-M22 IgG binding to the TSHR was comparable with a Pearson correlation coefficient r=0.95 ($^{125}$I-5C9 IgG versus $^{125}$I-TSH; FIG. 1a) and r=0.95 ($^{125}$I-5C9 IgG versus $^{125}$I-M22 IgG; FIG. 1b). FIG. 1c shows comparison of inhibition of $^{125}$I-TSH and $^{125}$I-M22 IgG by the same sera (Pearson coefficient r=0.99).

These experiments show that 5C9 IgG binding to the TSHR is inhibited effectively by serum TRAbs and that the inhibiting effect of serum TRAb on 5C9 IgG binding is similar to their inhibiting effect on TSH or M22 binding.

Table 4 shows the inhibition of $^{125}$I-5C9 IgG binding by different dilutions of patient serum TRAbs with TSH blocking activity (B1-B5) and patient serum TRAbs with powerful thyroid stimulating activity (S1, S2, S4). Binding of $^{125}$I-5C9 IgG was inhibited in a dose dependent manner by sera B1-B5 sera as well as by sera S1, S2 and S4. The same blocking and stimulating sera also inhibited $^{125}$I-TSH and $^{125}$I-M22 IgG binding in a dose dependent manner, furthermore the percentage of inhibition with all three labelled ligands were comparable at the same dilutions of sera (Table 4a & b).

These results indicate that TSHR autoantibodies with both stimulating and blocking activities inhibit 5C9 binding to the TSHR.

Inhibition of $^{125}$I-5C9 IgG Binding to the TSHR by Mouse MAbs with TSH Binding Inhibiting Activity The ability of different mouse TSHR MAbs with $^{125}$I-TSH binding inhibiting activity to inhibit $^{125}$I-5C9 binding to the TSHR was tested and compared with the effect on $^{125}$I-M22 IgG binding (Table 5). As shown in Table 5 all MAbs that had ability to inhibit $^{125}$I-TSH and $^{125}$I-M22 IgG binding also inhibited $^{125}$I-5C9 binding although in the case of some MAbs the inhibiting effect on $^{125}$I-5C9 and $^{125}$I-M22 binding was weaker than that on $^{125}$I-TSH binding.

These experiments suggest that there is a considerable overlap between the binding sites on the TSHR for 5C9 and those for mouse TSHR MAbs which have the ability to inhibit TSH binding.

Effect of 5C9 IgG on Stimulation of Cyclic AMP Production in CHO Cells Expressing TSHRs by Patient Sera As shown in Table 2, 5C9 IgG was able to block TSH or M22 stimulation of cyclic AMP levels in CHO cells expressing TSHRs. In a different series of experiments the effect of 5C9 IgG on the stimulating activity of patient serum TRAbs was tested and the results are shown in Table 6a. Sera T1-T9 and T11-T18 stimulated cyclic AMP production in CHO-TSHR cells and incubation with a control MAb IgG (2G4 specific for human thyroid peroxidase) had no effect on their stimulating activities. However, in the presence of 5C9 IgG (50 μL of 200 μg/mL), the stimulating activity of all sera tested was markedly reduced (Table 6a).

Dose response effects of 6 different sera (T1, T6, T3, T19, T20, T21) are shown in Tables 6b-g. In these experiments, concentrations of 5C9 IgG ranging from 0.1 μg/mL to 100 μg/mL caused a dose dependent reduction of serum stimulating activity and the effect of 5C9 IgG was comparable to the effect of 9D33, a mouse monoclonal antibody to the TSHR with blocking activity (described in WO2004/050708A2) in all sera tested except serum T3. In the case of T3 serum (Table 6a & 6d) about 50% inhibition of cyclic AMP production in the presence of 100 μg/mL of 5C9 IgG was observed, whereas 100 μg/mL of 9D33 IgG resulted in almost complete inhibition. This suggested that there might be some minor differences between the epitopes recognised by 5C9 and 9D33.

Effect of 5C9 IgG on Basal (i.e. Non-Stimulated) Cyclic AMP Production in CHO Cells Expressing TSHR As well as inhibiting the stimulating activity of TSH and TSHR antibodies, 5C9 inhibited the amount of cyclic AMP produced in the absence of these thyroid stimulators. In particular, Table 6b shows 1207±123 fmol/cell well of cyclic AMP produced in the presence of 100 μg/mL control monoclonal IgG (2G4) reduced to 301±38 fmol/cell well in the presence of 100 μg/mL of 5C9 IgG. The effects of 9D33 IgG were less with 721±183 fmol/cell well produced in the presence of 100 μg/mL 9D33 IgG. Similar results were obtained in the separate experiments shown in Tables 6d, 6e, 6f and 6g. This indicates that 5C9 IgG has a marked effect on the basal or constitutive activity of the TSHR.

Effect of 5C9 IgG on Stimulation of Cyclic AMP Production in CHO Cells Expressing TSHRs Containing Amino Acid Mutations The effects of single amino acid mutations in the TSHR on 5C9 ability to block cyclic AMP stimulating activity of porcine TSH in CHO-TSHR cells are shown in Table 7. In particular, the effect of 5C9 on stimulation of cyclic AMP production was studied in CHO cells expressing the TSHR with the following residues mutated to alanine: Lys 58, Ile 60, Arg 80, Tyr 82, Thr 104, Arg 109, Lys 129, Phe 134, Asp 151, Lys 183, Gln 235, Arg 255, Trp 258, Ser 281. In addition, the effect of a change of charge mutation was studied in the case of TSHR residues: Arg80Asp, Asp151Arg, Lys183Asp, Arg255Asp, in which in accordance with conventional notation the amino acid residue which is replaced, and its position in the primary sequence polypeptide, is indicated before the replacement amino acid residue. Previous studies have shown that change of charge mutation of TSHR Asp160Lys caused a loss of responsiveness of the TSHR to TSH while the response to M22 was not affected (patent application WO2006/016121A). Consequently, the effect of TSHR Asp160Lys mutation on 5C9 biological activity was studied using M22 as a stimulator of cyclic AMP in CHO-TSHR cells (Table 7l).

Out of all the TSHR mutations studied, only three mutations were found to affect the ability of 5C9 to act as an antagonist. Mutation of Lys129 to Ala (Table 7h) resulted in a complete loss of the ability of 5C9 IgG to block TSH stimulation of cyclic AMP production.

Also TSHR mutation Lys183Ala caused a partial reduction of 5C9 IgG blocking activity; 28% inhibition of TSH stimulation was observed at 1 μg/mL when tested with TSHR Lys183Ala mutation compared to 84% inhibition with wild type TSHR (Table 7m). Even at 100 μg/mL of 5C9 IgG, only partial inhibition of TSH stimulation (43%) was detectable in the experiments with TSHR Lys183Ala mutation whereas at this concentration a complete blocking of TSH stimulating activity (93%) was observed in the experiments with wild type receptors (Table 7m). When positively charged Lys 183 was mutated to negatively charged aspartic acid, the effect on 5C9 biological activity was similar to that observed with Lys183Ala mutation (Table 7m). This suggests that Lys183 is important for 5C9 biological activity. In the case of Asp151Ala mutation, a slight reduction of 5C9 IgG blocking activity: 49% inhibition at 1 μg/mL compared to 88% inhibition with wild type (Table 7j) was observed. However, in the presence of 100 μg/mL of 5C9 IgG the activity was the same as with wild type TSHR. When negatively charged Asp151 was mutated to positively charged arginine, a significant reduction in 5C9 IgG blocking activity was not observed (Table 7k).

The effect of TSHR mutations on 5C9 activity can be compared to the effects of TSHR mutations on 9D33 activity. As described in patent application WO2006/016121A, TSHR mutations Lys 58, Arg 80, Tyr 82, Arg 109, Lys 129 and Phe 134 had an effect on 9D33 activity. None of these mutations except Lys129, however, also had an effect on 5C9 activity. Furthermore, none of the mutations except Lys 129 that affected M22 activity (Arg 80, Tyr 82, Glu 107, Arg 109, Lys 129, Phe 130, Lys 183, Tyr 185, Arg 255 and Trp 258) as described in the patent application WO 2006/016121A affected 5C9 activity. In addition, Lys 183 mutation had a partial effect on 5C9 activity and M22 activity but had no effect on 9D33 activity.

These results indicate that there are differences in terms of the TSHR residues important for interaction with the thyroid stimulating human autoantibody M22, with mouse blocking antibody 9D33 and with human blocking autoantibody 5C9. Consequently, a combination of 5C9 with other TSHR antibodies with antagonist activities (such as 9D33) may be a particularly effective means of inhibiting the stimulating activity of patient serum TRAbs, other stimulators and/or TSHR constitutive activity.

Variable Region Sequences of 5C9

Sequence analysis of the genes coding for 5C9 indicated that the HC V region genes were from the VH3-53 family, the D genes from the D2-2 family and the J genes from the JH4 family. In the case of the LC, V region genes were from the 012 family and J region genes from the JK2 germline. The HC nucleotide and amino acid sequences are shown in FIGS. 2*a* and 2*b*, respectively and the LC nucleotide and amino acid sequences are shown in FIGS. 3*a* and 3*b*, respectively.

There are somatic mutations in the HC gene sequence compared to the germline sequences; in particular 1 silent mutation in FWR1, 2 replacement mutations in CDR2, 1 silent and 1 replacement mutation in CDR3 and 1 silent mutation in FWR4. However, the HC V region sequence is characterised by two insertions; one 6 base pairs long between the V and D genes and one 15 base pairs long between the D and J genes. Consequently, the HC CDR1 is 5 amino acids long, CDR2 is 16 amino acids long and the CDR3 is 18 amino acids long (FIG. 2*b*)

In the LC sequence there are: 1 silent mutation in FWR1, 1 replacement mutation in CDR1, 1 replacement mutation in CDR3 and a 6 base pairs long insertion between the V and J genes. The LC CDR1 is made up of 11 amino acids, CDR2 of 7 amino acids and CDR3 of 10 amino acids (FIG. 3*b*).

5C9 Based Assays for Detection of TSH or TRAbs

An example of an ELISA based on 5C9 IgG-biotin binding to TSHR coated plate wells for detection of TSHR autoantibodies is shown in Table 8. In this assay all samples positive for inhibition of TSH-biotin binding were also positive for 5C9 IgG-biotin binding. Furthermore, the absorbance signal, the percent inhibition and the derived units/L values were comparable in the TSH-biotin and 5C9-biotin assays (Table 8).

Effect of 5C9 IgG on Stimulating Activity of Mouse Thyroid Stimulating Monoclonal Antibodies (Mouse TSHR MAbs; TSMAbs) in CHO Cells Expressing TSHRs As shown in Table 9, 5C9 IgG was able to block the stimulation of cyclic AMP production by all five of the TSMAbs (1, 2, 4, 5 and 7) tested. For example TSMAb1 (Table 9) stimulated cyclic AMP levels to 18.94±7.4 pmol/mL while in the presence of 100 μg/mL 5C9 IgG only 1.24±0.07 pmol/mL of cyclic AMP was produced. This can be compared to 16.5±1.1 pmol/mL cyclic AMP levels in the presence of 100 μg/mL of the control MAb 2G4 (Table 9).

The cyclic AMP levels shown in Tables 9, as well as in Tables 10-15 below, are expressed in pmol/mL i.e. the levels of cyclic AMP per cell well are: pmol/mL÷5 (representing 200 μL of sample from each well assayed).

Effect of 5C9 IgG on Stimulating Activity of Native Human TSH and Recombinant Human TSH In CHO Cells Expressing TSHRs The ability of 5C9 IgG to block the cyclic AMP stimulation of porcine TSH is shown in Table 2 and Table 10. In addition 5C9 IgG showed the ability to inhibit cyclic AMP stimulation of both native human TSH (NIBSC reference preparation 81/565 from National Institute for Biological Standards and Control, South Mimms, Potters Bar EN6 3QG UK) and recombinant TSH (NIBSC reference preparation 94/674) (Table 10). In particular stimulation of cyclic AMP production by 100 ng/mL of either recombinant or native human TSH requires 0.1-1.0 μg/mL of 5C9 IgG to obtain complete inhibition of cyclic AMP production. At the time of blood collection for 5C9 isolation the levels of circulating TSH in the donor serum were 160 mU/L (approximately 32 ng/mL), the results obtained (Table 2a and Table 10) indicate that this level of circulating TSH would be completely blocked in the presence of 32-320 ng/mL of 5C9 IgG in the serum. The levels of TSHR autoantibodies in the donor serum were estimated, using inhibition of $^{125}$I-M22 binding to the TSHR (as described in Nakatake N, Sanders J, Richards T, Burne P, Barrett C, Dal Pra C, Presotto F, Betterle C, Furmaniak J, Rees Smith B 2006 Estimation of serum TSH receptor autoantibody concentration and affinity. Thyroid 16: 1077-1084), to be 1700 ng/mL (120 ng/mg) i.e. several fold higher than the concentration of 5C9 required for blocking of thyroid stimulation by TSH.

Effect of 5C9 IgG on Basal (i.e. Non-Stimulated) Cyclic AMP Activity in CHO Cells Expressing TSHR with Activating Mutations S281I, I568T and A623I 5C9 IgG was able to reduce the amount of cyclic AMP produced in CHO cells expressing TSHR with activating mutations when thyroid stimulators (i.e. TSH or TSHR antibodies) were absent. As shown in Table 11a the basal cyclic AMP concentration in CHO cells expressing the TSHR with activating mutation S281I was 9.90±1.51 pmol/mL in the absence of 5C9 and this was decreased to 4.17±0.60 pmol/mL in the presence of 0.01 μg/mL 5C9 IgG and to 3.44±0.63 pmol/mL in the presence of 1 μg/mL 5C9 IgG. The blocking mouse TSHR MAb 9D33 had little effect as did the control MAb 2G4 (Table 11a).

Similar results were obtained with the TSHR activating mutation I568T (Table 11b), which showed a basal cyclic AMP concentration of 21.39±5.31 pmol/mL. This decreased to 5.29±0.75 pmol/mL on addition of 1 μg/mL of 5C9 IgG compared to 20.52±0.95 pmol/mL and 21.65±1.99 pmol/mL in the case of addition of 2G4 IgG and 5C9 IgG, respectively. In the case of a third TSHR activating mutation studied i.e. A623I with basal cyclic AMP concentration of 36.89 pmol/mL addition of 1 μg/mL of 5C9 IgG reduced the cyclic AMP levels to 16.43±1.27 pmol/mL compared to little effects with 1 μg/ml of control IgG 2G4 (28.96±2.29 pmol/mL) or 1 μg/mL of 9D33 IgG (40.09±7.73 pmol/mL) (Table 11c).

These results indicate that 5C9 unlike the mouse blocking MAb 9D33 has a marked effect on cyclic AMP production associated with the TSHR activating mutations even when the mutations are in different parts of the TSHR (i.e. S281I in the extracellular domain, I568T in the second extracellular loop of the transmembrane domain and A623I in the third intracellular loop of the transmembrane domain).

Comparison of the Effect of 5C9 and a Mouse TSHR Blocking Monoclonal Antibody 9D33 and the Mixture of the Two Antibodies on TSH Mediated Stimulation of Cyclic AMP Production in CHO Cells Expressing the Wild Type TSHR The human TSHR blocking MAb 5C9 and the mouse TSHR blocking MAb 9D33 at concentrations as low as 1 μg/mL have the ability to block TSHR cyclic AMP stimulating activity of TSH in CHO-TSHR cells as shown in previous experiments and in Table 12. The effects of the 9D33 IgG and 5C9 IgG on TSH mediated stimulation of cyclic AMP were additive as shown in Table 12; Experiments 1-5). The same additive effect was observed when two different concentrations of TSH (3 ng/mL and 0.3 ng/mL) were used for stimulation (Table 12; Experiments 1-3 and Experiments 4 and 5, respectively).

Comparison of the Effect of 5C9 and a Mouse TSHR Blocking Monoclonal Antibody 9D33 and the Mixture of the Two Antibodies on M22 Mediated Stimulation of Cyclic AMP Production in CHO Cells Expressing the Wild Type TSHR As shown before, 5C9 and 9D33 also are able to inhibit M22 Fab mediated stimulation of cyclic AMP in CHO-TSHR cells. The effects of the 9D33 IgG and 5C9 IgG on M22 mediated stimulation of cyclic AMP were additive (Table 13 Experiments 1-4). The same additive effect was observed when two different concentrations of M22 Fab (3 ng/mL and 0.3 ng/mL) were used for stimulation (Table 13; Experiments 1 and 2 and Experiments 3 and 4, respectively).

The additive effects of 5C9 IgG and 9D33 IgG were similar for both TSH and M22 mediated stimulation of cyclic AMP production (Tables 12 and 13).

Effect of 5C9 on Basal (i.e. Non-Stimulated) Cyclic AMP Activity in CHO Cells Expressing a High Number of Wild Type TSHRs Per Cell A CHO cell line expressing approximately $5 \times 10^5$ receptors per cell showed higher levels of basal (i.e. non-stimulated) cyclic AMP compared to a standard CHO cell line (expressing approximately $5 \times 10^4$ TSHR per cell) used in previous experiments (for example Tables 9-13) i.e. 47.1±11.7 pmol/mL compared to approximately 1.0 pmol/mL, respectively. The effect of 5C9 IgG and 9D33 IgG on wild type TSHR basal activity was assessed using the cell line expressing a high number of receptors per cell. Incubation with 9D33 IgG and a negative control antibody to GAD (5B3) resulted in 0-5.3% inhibition of basal cyclic AMP activity (Table 14; Experiment 1) indicating that the blocking mouse MAb 9D33 or control MAb have no effect on basal cyclic AMP production in CHO cells expressing the wild type TSHR. However, in the case of 5C9 IgG a clear inhibition of basal cyclic AMP activity was observed (Table 14; Experiment 2) with 0.1 μg/mL and 10 μg/mL causing 45.7% and 74.6% inhibition respectively. In addition, 5C9 Fab and 5C9 F(ab') were also effective inhibitors of basal cyclic AMP activity in CHO cells expressing a high number of TSHRs per cell (Table 14 experiment 3). For example, 1 μg/mL and 100 μg/mL of 5C9 Fab showed 39% and 61% inhibition of basal cyclic AMP production, respectively compared to 48% inhibition by 5C9 F(ab') at 100 μg/mL (Table 14 experiment 3).

Effect of Patient Serum TSHR Autoantibodies with Antagonist (i.e. Blocking) Activity on Basal (i.e. Non-Stimulated) Cyclic AMP Activity in CHO Cells Expressing TSHR with Activating Mutation I568T The basal cyclic AMP production by TSHR I568T cells in the presence of cyclic AMP assay buffer of 20.5±8.7 pmol/mL was essentially unaffected by addition of normal pool sera from healthy blood donors (NPS) or 3 different individual healthy blood donor sera (N1-N3) tested at 1/10 and 1/50 dilution. The basal cyclic AMP production in the presence of NPS and N1-N3 sera showed 0-14% inhibition compared to basal cyclic AMP production in the presence of cyclic AMP assay buffer (Table 15). However, in the presence of 4 different sera with high levels of blocking type TRAbs (B2-B5) 23-89% inhibition of basal cyclic AMP production was observed (Table 15). In the presence of 5C9 IgG (1 μg/mL), 83% inhibition of TSHR I568T basal cyclic AMP activity was observed. The dose response effect of 2 blocking sera (B3 and B4) on basal cyclic AMP production in CHO cells expressing TSHR with I568T mutation is also shown in Table 15.

These results indicate that 5C9 has the TSHR blocking activity characteristic of patient blocking TSHR autoantibodies in particular with respect to inhibition of basal cyclic AMP production in the TSHR activating mutant I568T.

Effect of Patient Serum TSHR Autoantibodies with Antagonist Activity on Basal (i.e. Non-Stimulated) Cyclic AMP Activity in CHO Cells Expressing TSHR with Activating Mutation S281I The basal cyclic AMP production by TSHR S281I cells in the presence of cyclic AMP assay buffer was 11.2±2.0 pmol/mL and incubation with healthy blood donor pool sera or individual healthy blood donor sera (diluted 1/10 or 1/50) had no effect (Table 16). In contrast, in the presence of 4 different sera with high levels of blocking type of TRAbs (B2-B5) 31-56% inhibition of basal cyclic AMP production was observed (Table 16). 5C9 IgG at 1 μg/mL caused 71% inhibition of basal cyclic AMP activity in the experiments with TSHR S281I.

Effect of Patient Serum TSHR Autoantibodies with Antagonist Activity on Basal (i.e. Non-Stimulated) Cyclic AMP Activity in CHO Cells Expressing TSHR with Activating Mutation A623I The basal cyclic AMP production in the case of TSHR A623I cells was 43.5±11.2 pmol/mL in the presence of cyclic AMP assay buffer and was essentially unaffected by incubation with healthy blood donor pool or individual sera (Table 17). Incubation with four different sera with high levels of blocking type of TRAbs (B2-B5) caused—1% to 56% inhibition of cyclic AMP in these experiments (Table 17). This can be compared with 49% inhibition by 5C9 IgG at 1 µg/mL in the same experiment.

Effect of Patient Serum TSHR Autoantibodies with Antagonist Activity on Basal (i.e. Non-Stimulated) Cyclic AMP Activity in CHO Cells Expressing Approximately $5\times10^5$ Wild Type TSHRs Per Cell The basal cyclic AMP production in CHO cells expressing higher number of wild type TSHRs per cell was 28.1±0.7 pmol/mL in this series of experiments. When the cells were incubated with healthy blood donor pool or individual sera (N1-N3) at 1/10 dilutions basal cyclic AMP levels ranged between 99% and 146% of cyclic AMP levels in the presence of cyclic AMP assay buffer while at 1/50 dilutions the range was from 93% to 137%. Out of 4 sera with blocking type TSHR autoantibodies tested, one serum (B2) had no effect on basal cyclic AMP production (Table 18). In the case of two sera (B3 and B5) the levels of cyclic AMP increased relative to the levels observed in the presence of cyclic AMP assay buffer (Table 18). It may well be that sera B3 and B5 contain a mixture of TSHR autoantibodies with stimulating and blocking activities. In contrast, serum B4 had a clear inhibiting effect on basal cyclic AMP production at 1/10 and 1/50 dilution i.e. 31% and 61% respectively of basal cyclic AMP levels relative to the levels in the presence of cyclic AMP assay buffer (Table 18). This can be compared to the levels in the presence of 5C9 IgG at 1 µg/mL of 33% relative to the levels in the presence of cyclic AMP assay buffer (Table 18).

Overall 5C9 IgG shows similar effects on basal cyclic AMP production in CHO cells transfected with wild type TSHR or with TSHR with activating mutations to the effects observed with sera from patients positive for blocking type TSHR autoantibodies. However, the effect of individual patient sera varies in the case of different mutations (Table 19). In the case of wild type TSHR some sera show a stimulating effect presumably due to the presence of TSHR stimulating autoantibodies as well as blocking autoantibodies (Table 19).

Effect of 5C9 on Stimulation of Cyclic AMP Production in CHO Cells Expressing TSHRs Containing Amino Acid Mutations The effect of 5C9 on stimulation of cyclic AMP production in CHO cells expressing TSHRs with amino acid mutations was extended to include the following mutations to alanine: Asp43, Glu61, His105, Glu107, Phe130, Glu178, Tyr185, Asp203, Tyr206, Lys209, Asp232, Lys250, Glu251, Thr257, Arg274, Asp276 (Table 20 a-p and summarised in Table 21).

Mutation of TSHR amino acids Asp43, Glu61, His105, Glu107, Tyr185, Asp232 and Thr275 to alanine had no effect on 5C9 IgG's ability to inhibit TSH stimulated cyclic AMP production. The ability of 5C9 to inhibit TSH stimulated cyclic AMP production was reduced by mutation of TSHR Phe130, Glu178, Asp203, Tyr206, Lys250, Glu251 and Asp276 to alanine. In the case of 2 mutations Lys209Ala and Asp274Ala, the ability of 5C9 IgG to inhibit TSH mediated cyclic AMP production was enhanced.

In summary (Tables 7, 20 and 21), 10 TSHR residues Lys129, Phe130, Asp151, Glu178, Lys183, Asp203, Tyr206, Lys250, Glu251 and Asp276 all reduced the ability of 5C9 to inhibit cyclic AMP stimulation by TSH compared to the wild type TSHR. Mutation of TSHR Lys129 and Asp203 showed the greatest effect and caused complete inhibition of 5C9 activity.

Effect of Blocking Sera B2-B5 on TSH Mediated Stimulation of Cyclic AMP Production in CHO Cells Expressing Wild Type TSHR Compared to Mutated TSHR Asp203Ala The blocking effect at 1 µg/mL 5C9 on the wild type TSHR (92% inhibition of TSH induced cyclic AMP stimulation) was reduced to 4% in the case of TSHR Asp203Ala mutation (Table 22).

Blocking serum B4 activity was unaffected by TSHR Asp203Ala mutation while a slight reduction in percent inhibition of TSH induced cyclic AMP stimulation was seen with blocking sera B2 and B3 in the case of TSHR Asp203Ala compared to the wild type TSHR.

In the case of one serum B5, a marked reduction in percent inhibition of TSH induced cyclic AMP stimulation was observed; i.e. 69% inhibition compared to 30% inhibition in wild type and mutated TSHR respectively.

The effect of TSHR Asp203Ala mutation on 5C9 activity was greater than the effect on the activity of blocking sera, however the blocking activity of 3/4 sera tested was affected to varying degrees. This may indicate that the binding sites for blocking TSHR autoantibodies and 5C9 overlap but there are some differences in the actual TSHR amino acids in contact with different sera.

SUMMARY AND CONCLUSIONS

The experiments described above provide evidence that an antibody in accordance with the invention such as 5C9 is able to block stimulating activity of different thyroid stimulators, including human and mouse TSHR stimulating antibodies, native human and animal TSH and recombinant human TSH. Furthermore, evidence is provided that two different blocking type antibodies, i.e. a human MAb 5C9 and a mouse MAb 9D33 that, when tested individually, have the ability to block TSH or M22 meditated stimulation of cyclic AMP in CHO cells expressing the TSHR, show additive blocking effect on TSH or M22 stimulation when mixed together.

Antibodies in accordance with the invention such as 5C9 have a novel effect on the TSHR basal (i.e. non-stimulated) cyclic AMP activity. These effects have been studied by experiments using TSHR transfected CHO cells having higher levels of basal cyclic AMP i.e. the blocking effect of antibodies in accordance with the invention, such as 5C9, on basal cyclic AMP activity has been confirmed. Furthermore, it has been shown that some sera with TSHR autoantibodies with blocking (antagonist) activity have the ability to block basal cyclic AMP activity in these TSHR transfected cells. The experiments also provide evidence of the blocking effect of antibodies in accordance with the invention, such as 5C9, and serum TSHR blocking autoantibodies on basal cyclic AMP activity associated with activating TSHR mutations.

These results emphasise that 5C9 is a human MAb showing the characteristics of blocking type TSHR autoantibodies i.e. that it is representative of patient serum TSHR autoantibodies associated with autoimmune thyroid disease.

The experiments described also allowed identification of some of the TSHR amino acids important for the blocking activity of antibodies in accordance with the invention.

Overall, the results indicate that antibodies in accordance with the invention, such as 5C9, show similar TSHR binding activity and similar biological effects on TSHR function as TSHR blocking autoantibodies found in different sera from patients with autoimmune thyroid disease. Consequently, having characteristics and biological activity of serum blocking TSHR autoantibodies, antibodies in accordance with the invention, such as 5C9, have applications for inactivation of the TSHR in various clinical conditions. These conditions include TSHR activation mediated by TSH, TSHR activation mediated by thyroid stimulating TSHR autoantibodies, basal (non-stimulated, constitutive) TSHR activity and TSHR activation associated with activating TSHR mutations. Consequently, antibodies in accordance with the invention, such as 5C9 have applications for management and control of the conditions associated with TSHR activation mentioned above; for example Graves' disease, Graves' ophthalmopathy, hyperthyroidism due to TSHR activating mutations, hyperthyroidism due to abnormal levels of TSH (pathological or pharmacological), thyroid cancer and thyroid cancer metastases.

TABLE 1

Inhibition of binding of $^{125}$I-TSH, $^{125}$I-M22 IgG or $^{125}$I-5C9 IgG to TSHR coated tubes by 5C9 IgG, lymphocyte donor IgG and lymphocyte donor plasma

| Sample | $^{125}$I-TSH (% inhibition) | $^{125}$I-M22 IgG (% inhibition) | $^{125}$I-5C9 (% inhibition) |
|---|---|---|---|
| Donor plasma (diluted in HBD pool) | | | |
| 1/5 | 97 | 92 | 93 |
| 1/10 | 95 | 91 | 92 |
| 1/20 | 82 | 85 | 82 |
| 1/40 | 57 | 75 | 56 |
| 1/80 | 30 | 53 | 29 |
| 1/160 | 16 | 29 | 13 |
| 1/320 | 8 | 13 | 10 |
| Donor IgG (diluted in 1 mg/mL HBD pool IgG) | | | |
| 1 mg/mL | 94 | 89 | 91 |
| 0.5 mg/mL | 90 | 86 | 89 |
| 0.25 mg/mL | 63 | 79 | 64 |
| 0.1 mg/mL | 29 | 51 | 26 |
| 0.05 mg/mL | 13 | 29 | 15 |
| 0.025 mg/mL | 2 | 17 | 5 |
| 0.01 mg/mL | 5 | 9 | 1 |
| 5C9 IgG (diluted in 100 µg/mL 2G4) | | | |
| 100 µg/mL | 84 | 85 | 88 |
| 50 µg/mL | 76 | 81 | 80 |
| 25 µg/mL | 67 | 69 | 71 |
| 10 µg/mL | 54 | 60 | 59 |
| 5 µg/mL | 47 | 53 | 54 |
| 2.5 µg/mL | 42 | 43 | 49 |
| 1 µg/mL | 37 | 31 | 42 |
| 0.5 µg/mL | 33 | 32 | 41 |
| 0.1 µg/mL | 29 | 22 | 34 |
| 0.05 µg/mL | 25 | 19 | 30 |
| 0.01 µg/mL | 13 | 9 | 15 |
| 0.005 µg/mL | 12 | 5 | 11 |
| 0.001 µg/mL | 3 | 2 | 3 |

Average % binding of labelled tracer to TSHR coated tubes was:
14% in the experiments with $^{125}$I-TSH;
21% in the experiments with $^{125}$I-M22 IgG
and 20% in the experiments with $^{125}$I-5C9
HBD pool = pool of healthy blood donor sera
2G4 = control IgG (human MAb to thyroid peroxidase).

TABLE 2a

Effect of 5C9 IgG or lymphocyte donor serum IgG on TSH stimulation of cyclic AMP production in CHO cells expressing human TSHR

| Sample | IgG concentration | Cyclic AMP (fmol/cell well; mean ± SD, n = 3) |
|---|---|---|
| pTSH (3 ng/mL) only | | 19020 ± 2154 |
| 5C9 IgG only | 1 µg/mL | 141 ± 5 |
| 5C9 IgG + pTSH (3 ng/mL) | 1 µg/mL | 2208 ± 329 |
| 5C9 IgG + pTSH (3 ng/mL) | 0.5 µg/mL | 4754 ± 876 |
| 5C9 IgG + pTSH (3 ng/mL) | 0.1 µg/mL | 11874 ± 4214 |
| 5C9 IgG + pTSH (3 ng/mL) | 0.08 µg/mL | 14525 ± 3690 |
| 5C9 IgG + pTSH (3 ng/mL) | 0.06 µg/mL | 13290[1] |
| 5C9 IgG + pTSH (3 ng/mL) | 0.04 µg/mL | 13928 ± 1572 |
| 5C9 IgG + pTSH (3 ng/mL) | 0.02 µg/mL | 16432 ± 9286 |
| 5C9 IgG + pTSH (3 ng/mL) | 0.01 µg/mL | 18969 ± 5308 |
| Cyclic AMP assay buffer only | | 207 ± 51 |
| Donor serum[a] 1/10 | 1.43 mg/mL[b] | 1102 ± 46 |
| Donor serum 1/10 + pTSH (3 ng/mL) | 1.43 mg/mL | 5931 ± 350 |
| Donor serum 1/20 + pTSH (3 ng/mL) | 0.715 mg/mL | 16886 ± 728 |
| Donor serum 1/30 + pTSH (3 ng/mL) | 0.477 mg/mL | 16453 ± 3455 |
| Donor serum 1/40 + pTSH (3 ng/mL) | 0.358 mg/mL | 17716 ± 1753 |
| Donor serum 1/50 + pTSH (3 ng/mL) | 0.286 mg/mL | 17928 ± 4772 |
| Donor serum 1/100 + pTSH (3 ng/mL) | 0.143 mg/mL | 18226 ± 2268 |

[1]single determination
[a]Donor serum was diluted in cyclic AMP assay buffer as indicated
[b]IgG concentration of undiluted serum determined by nephelometry was 14.3 mg/mL
5C9 IgG and TSH were diluted in cyclic AMP assay buffer.

TABLE 2b

Inhibition of TSH induced cyclic AMP production in CHO cells expressing TSHR by 5C9 IgG, F(ab')$_2$ and Fab fragments

| Sample | Cyclic AMP (fmol/cell well; mean ± SD, n = 3) |
|---|---|
| Example 1 | |
| Cyclic AMP assay buffer only | 586 ± 148 |
| TSH 3 ng/mL only | 18557 ± 363 |
| 5C9 Fab 100 µg/mL only | 235 ± 35 |
| 5C9 Fab 100 µg/mL + TSH | 938 ± 93 |
| 5C9 Fab 10 µg/mL + TSH | 1283 ± 239 |
| 5C9 F(ab')$_2$ 100 µg/mL only | 204 ± 12 |
| 5C9 F(ab')$_2$ 100 µg/mL + TSH | 877 ± 195 |
| 5C9 F(ab')$_2$ 10 µg/mL + TSH | 916 ± 188 |
| 5C9 IgG 100 µg/mL only | 237 ± 54 |
| 5C9 IgG 100 µg/mL + TSH | 754 ± 177 |
| 5C9 IgG 10 µg/mL + TSH | 247 ± 115 |
| 2G4 IgG 100 µg/mL + TSH | 6082[1] |
| Example 2 | |
| Cyclic AMP assay buffer only | 584 ± 111 |
| TSH 3 ng/mL only | 19363 ± 5198 |
| 2G4 IgG 100 µg/mL only | 608 ± 169 |
| 2G4 IgG 100 µg/mL + TSH | 18147 ± 972 |
| 2G4 IgG 10 µg/mL + TSH | 18114 ± 6544 |
| 5C9 F(ab')$_2$ 100 µg/mL only | 414 ± 22 |
| 5C9 F(ab')$_2$ 100 µg/mL + TSH | 1058 ± 223 |
| 5C9 F(ab')$_2$ 10 µg/mL + TSH | 1333 ± 443 |
| 5C9 IgG 100 µg/mL only | 338 ± 108 |
| 5C9 IgG 100 µg/mL + TSH | 1109 ± 375 |
| 5C9 IgG 10 µg/mL + TSH | 723 ± 71 |
| 5C9 Fab 100 µg/mL only | 212 ± 37 |
| 5C9 Fab 100 µg/mL + TSH | 867 ± 127 |
| 5C9 Fab 10 µg/mL + TSH | 4131 ± 776 |

[1]mean of duplicate samples
2G4 = control IgG (human MAb to thyroid peroxidase).
Antibody and TSH preparations were diluted in cyclic AMP assay buffer.

TABLE 2c

Effect of 5C9 IgG and 9D33 IgG on stimulation of cyclic AMP production in CHO cells expressing human TSHR by TSH or M22 Fab

| Test sample | Cyclic AMP production (fmol/cell well; mean ± SD n = 3) |
|---|---|
| Cyclic AMP assay buffer only | 473 ± 21 |
| pTSH 3 ng/mL only | 12,270 ± 980 |
| 5C9 IgG 100 µg/mL only | 426 ± 27 |
| 5C9 IgG 10 µg/mL only | 360 ± 53 |
| 5C9 IgG 1 µg/mL only | 376 ± 18 |
| 5C9 IgG 0.1 µg/mL only | 404 ± 42 |
| 5C9 IgG 0.01 µg/mL only | 578 ± 65 |
| 5C9 IgG 0.001 µg/mL only | 554 ± 47 |
| 5C9 IgG 100 µg/mL + pTSH 3 ng/mL | 1094 ± 70 |
| 5C9 IgG 10 µg/mL + pTSH 3 ng/mL | 1028 ± 47 |
| 5C9 IgG 1 µg/mL + pTSH 3 ng/mL | 1872 ± 168 |
| 5C9 IgG 0.1 µg/mL + pTSH 3 ng/mL | 3920 ± 464 |
| 5C9 IgG 0.01 µg/mL + pTSH 3 ng/mL | 15,050 ± 386 |
| 5C9 IgG 0.001 µg/mL + pTSH 3 ng/mL | 14,147 ± 1,310 |
| 9D33 IgG 100 µg/mL only | 626 ± 127 |
| 9D33 IgG 100 µg/mL + pTSH 3 ng/mL | 2,218 ± 5 |
| M22 Fab 3 ng/mL only | 9,432 ± 822 |
| 5C9 IgG 100 µg/mL + M22 Fab 3 ng/mL | 354 ± 56 |
| 5C9 IgG 10 µg/mL + M22 Fab 3 ng/mL | 638[1] ± 190 |
| 5C9 IgG 1 µg/mL + M22 Fab 3 ng/mL | 956 ± 169 |
| 5C9 IgG 0.1 µg/mL + M22 Fab 3 ng/mL | 1,298 ± 134 |
| 5C9 IgG 0.01 µg/mL + M22 Fab 3 ng/mL | 9,978 ± 919 |
| 5C9 IgG 0.001 µg/mL + M22 Fab 3 ng/mL | 11,614 ± 393 |
| 9D33 IgG 100 µg/mL + M22 Fab 3 ng/mL | 1,048 ± 10 |

[1]mean of duplicate samples
9D33 is a mouse antibody which blocks both TSH and TRAb mediated stimulation of cyclic AMP production in CHO cells expressing the TSHR.
Antibody and TSH preparations were diluted in cyclic AMP assay buffer.

TABLE 3

Binding of $^{125}$I-5C9 IgG, $^{125}$I-TSH and $^{125}$I-M22 IgG binding to TSHR coated tubes and inhibition by patient serum samples

| Serum sample | $^{125}$I-5C9 binding inhibition (%) | $^{125}$I-TSH binding inhibition (%) | $^{125}$I-M22 binding inhibition (%) |
|---|---|---|---|
| N1 | 15.7 | 0 | 9.3 |
| N2 | 3.3 | 1.2 | 7.2 |
| N3 | 15.3 | 1.9 | 0.7 |
| N4 | 4.0 | 4.2 | 0 |
| N5 | 18.9 | 6.3 | 11.4 |
| N6 | 5.9 | 2.9 | 1.4 |
| N7 | 17.1 | 7.2 | 9.4 |
| N8 | 5.5 | 0 | 0 |
| N9 | 11.2 | 4.2 | 2.9 |
| N10 | 10.5 | 6.5 | 5.8 |
| G1 | 79.6 | 83.6 | 80.5 |
| G2 | 75.8 | 77.5 | 73.5 |
| G3 | 82.2 | 77.5 | 78.1 |
| G4 | 77.7 | 74.9 | 74.8 |
| G5 | 77.0 | 73.6 | 71.5 |
| G6 | 64.7 | 71.6 | 69.1 |
| G7 | 75.6 | 74.3 | 66.0 |
| G8 | 73.7 | 74.7 | 77 |
| G9 | 76.1 | 78.5 | 79.2 |
| G10 | 75.9 | 75.8 | 69.9 |
| G11 | 81.6 | 82.5 | 79.7 |
| G12 | 71.6 | 76.6 | 73.9 |
| G13 | 72.3 | 71.1 | 70.2 |
| G14 | 81.9 | 85.8 | 80.9 |
| G15 | 84.9 | 85.3 | 84.4 |
| G16 | 80.5 | 84.9 | 81.7 |
| G17 | 85.0 | 86.9 | 85.3 |
| G18 | 84.9 | 85 | 84.2 |
| G19 | 85.1 | 87.3 | 85.4 |
| G20 | 84.4 | 89.3 | 87.7 |
| G21 | 77.6 | 84.9 | 77.0 |
| G22 | 67.1 | 59.7 | 61.5 |
| G23 | 57.5 | 62.2 | 59.5 |
| G24 | 65.7 | 67.1 | 64.4 |
| G25 | 59.3 | 56.3 | 62.3 |
| G26 | 38.4 | 67.7 | 69.4 |
| G27 | 22.0 | 59.1 | 58.9 |
| G28 | 68.3 | 69.7 | 72.8 |
| G29 | 40.9 | 54.2 | 50.4 |
| G30 | 71.2 | 69.1 | 72 |
| G31 | 62.2 | 59.2 | 62.0 |
| G32 | 46.0 | 40.6 | 49.2 |
| G33 | 44.0 | 25.9 | 37.2 |
| G34 | 52.0 | 48 | 55.0 |
| G35 | 60.1 | 54.4 | 60.7 |
| G36 | 29.3 | 31.4 | 43.2 |
| G37 | 49.0 | 44.1 | 45.5 |
| G38 | 40.1 | 26.7 | 29.8 |
| G39 | 66.4 | 54.7 | 58.9 |
| G40 | 48.8 | 48.5 | 48.5 |

N1-10 = sera from healthy blood donors
G1-G40 = sera from patients with a history of Graves' disease
Results are means of closely agreeing duplicate determinations $$\% \text{ inhibition} = 100 - \left(\frac{A}{B} \times 100\right)$$

where A = binding in the presence of test serum; B = binding in the presence of a pool of healthy blood donor serum (HBD pool).
$^{125}$I-5C9 in presence of HBD pool gave 20% binding, $^{125}$I-TSH in presence of HBD pool gave 12% binding and $^{125}$I-M22 in presence of HBD pool gave 17% binding.

TABLE 4a

Comparison of the inhibition of $^{125}$I-5C9 IgG, $^{125}$I-TSH and $^{125}$I-M22 IgG, binding to TSHR coated tubes by patient serum with either blocking or stimulating activity

| Test samples | $^{125}$I-5C9 binding inhibition (%) | $^{125}$I-TSH binding inhibition (%) | $^{125}$I-M22 binding inhibition (%) |
|---|---|---|---|
| Assay calibrators | | | |
| 40 U/L | 87 | 90 | 84.4 |
| 8 U/L | 62 | 67 | 63.0 |
| 2 U/L | 15 | 27 | 25.6 |
| 1 U/L | 4.3 | 15 | 14.8 |
| Positive control serum | 34 | 35 | 38.7 |
| Blocking sera | | | |
| B1 | | | |
| 1/5 | 93 | 95 | 91.7 |
| 1/10 | 92 | 94 | 89.2 |
| 1/20 | 91 | 91 | 85.9 |
| 1/40 | 85 | 80 | 78.8 |
| 1/80 | 67 | 55 | 67.4 |
| 1/160 | 33 | 33 | 45.9 |
| 1/320 | 20 | 17 | 26.4 |
| B2 | | | |
| 1/5 | 92 | 91 | 86.6 |
| 1/10 | 85 | 85 | 79.5 |
| 1/20 | NT | 73 | 66.2 |
| 1/40 | 68 | 51 | 50.0 |
| 1/80 | 42 | 34 | 29.7 |
| 1/160 | 19 | 22 | 20.3 |
| 1/320 | NT | 13 | 7.8 |
| B3 | | | |
| 1/5 | 89 | 93 | 85.5 |
| 1/10 | 82 | 84 | 76.3 |
| 1/20 | 62 | 64 | 61.7 |

TABLE 4a-continued

Comparison of the inhibition of $^{125}$I-5C9 IgG, $^{125}$I-TSH and $^{125}$I-M22 IgG, binding to TSHR coated tubes by patient serum with either blocking or stimulating activity

| Test samples | $^{125}$I-5C9 binding inhibition (%) | $^{125}$I-TSH binding inhibition (%) | $^{125}$I-M22 binding inhibition (%) |
|---|---|---|---|
| 1/40 | 37 | 44 | 42.5 |
| 1/80 | 14 | 26 | 26.2 |
| 1/160 | NT | 12 | 16.6 |
| 1/320 | NT | 7 | 8.9 |
| B4 | | | |
| 1/5 | 93 | 94 | 90.3 |
| 1/10 | 93 | 95 | 88.5 |
| 1/20 | 92 | 93 | 85.1 |
| 1/40 | 89 | 89 | 81.1 |
| 1/80 | 78 | 76 | 72.1 |
| 1/160 | 56 | 54 | 56.9 |
| 1/320 | 34 | 37 | 39.9 |
| B5 | | | |
| 1/5 | 94 | 93 | 90.3 |
| 1/10 | 91 | 92 | 87.0 |
| 1/20 | 87 | 87 | 82.2 |
| 1/40 | 74 | 72 | 71.7 |
| 1/80 | 56 | 47 | 54.6 |
| 1/160 | 31 | 29 | 36.4 |
| 1/320 | 19 | 17 | 21.4 |
| Stimulating serum | | | |
| S1 | | | |
| 1/5 | 89 | 91 | 84.9 |
| 1/10 | 80 | 84 | 75.4 |
| 1/20 | 63 | 67 | 62.9 |
| 1/40 | 42 | 50 | 46.2 |
| 1/80 | 26 | 34 | 31.9 |
| 1/160 | 9 | 21 | 16.3 |
| 1/320 | 16 | 4 | 10.6 |

TABLE 4b

| Test samples | $^{125}$I-5C9 binding inhibition (%) | $^{125}$I-TSH binding inhibition (%) | $^{125}$I-M22 binding inhibition (%) |
|---|---|---|---|
| Assay calibrators | | | |
| 40 U/L | 87.2 | 90.4 | 82.2 |
| 8 U/L | 62.0 | 67.2 | 63.3 |
| 2 U/L | 21.3 | 22.0 | 27.9 |
| 1 U/L | 15.0 | 13.0 | 21.8 |
| Positive control serum | 34.2 | 31.4 | 38.6 |
| HBD pool | 6.2 | −0.6 | 12.5 |
| S2 | | | |
| Neat | 91.8 | 95.1 | 88.6 |
| 1/5 | 76.7 | 84.5 | 72.7 |
| 1/10 | 62.3 | 71.4 | 66.4 |
| 1/20 | 48.2 | 57.0 | 51.9 |
| 1/40 | 31.8 | 39.3 | 41.4 |
| 1/80 | 21.3 | 19.4 | 32.9 |
| 1/160 | 16.8 | 9.7 | 25.1 |
| S4 | | | |
| Neat | 91.0 | 92.9 | 86.2 |
| 1/5 | 71.0 | 72.4 | 68.7 |
| 1/10 | 55.5 | 55.6 | 57.4 |
| 1/20 | 39.9 | 34.0 | 46.3 |
| 1/40 | 27.3 | 16.4 | 35.4 |
| 1/80 | 17.0 | 8.6 | 25.4 |
| 1/160 | 16.1 | 2.1 | 19.5 |

B1-B5 are patient sera with high levels of TRAb with antagonist (blocking) activity.
B3 is serum from the lymphocyte donor for 5C9
S1, S2 and S4 are patient sera with high levels of TRAb with agonist (stimulating) activity
Assay calibrators 40 U/L, 8 U/L, 2 U/L and 1 U/L are dilutions of M22 IgG in a pool of healthy blood donor sera (HBD pool) with activities in U/L of NIBSC 90/672 assessed by inhibition of labelled TSH binding to TSHR coated tubes.

$$\% \text{ inhibition} = 100 - \left(\frac{A}{B} \times 100\right)$$

where A = test sample; B = HBD pool
NT = not tested
1/5, 1/10 etc indicate dilution factor of test sera in HBD pool, neat = undiluted serum In the presence of the HBD pool approximately 20%, 17% and 12% of the $^{125}$I-labelled M22 IgG, 5C9 IgG and TSH respectively bound to the TSHR coated tubes.

TABLE 5

Inhibition of $^{125}$I-labelled TSH, $^{125}$I-M22 IgG and $^{125}$I-5C9 IgG binding to TSHR coated tubes by different concentrations of mouse MAbs to the TSHR

| Test sample | | $^{125}$I-TSH (% inhib) | $^{125}$I-M22 IgG (% inhib) | $^{125}$I-5C9 IgG (% inhib) |
|---|---|---|---|---|
| 5C9 IgG | 100 μg/mL | 50 | 53 | 65.5 |
| 5C9 IgG | 10 μg/mL | 30 | 22 | 42 |
| 5C9 IgG | 1 μg/mL | 21 | 14 | 27 |
| 5C9 IgG | 0.1 μg/mL | 8 | 6 | 10 |
| 5C9 IgG | 0.01 μg/mL | 2 | 5 | 0 |
| 7C71 IgG[1] | 100 μg/mL | 65 | 68 | 82 |
| 7C71 IgG | 10 μg/mL | 55 | 64 | 65 |
| 7C71 IgG | 1 μg/mL | 47 | 58 | 53 |
| 7C71 IgG | 0.1 μg/mL | 28 | 37 | 17 |
| 7C71 IgG | 0.01 μg/mL | 8 | 14 | 5 |
| 10C31 IgG[1] | 100 μg/mL | 68 | 69 | 76 |
| 10C31 IgG | 10 μg/mL | 56 | 71 | 62 |
| 10C31 IgG | 1 μg/mL | 52 | 62 | 54 |
| 10C31 IgG | 0.1 μg/mL | 39 | 48 | 36 |
| 10C31 IgG | 0.01 μg/mL | 15 | 24 | 8 |
| 2E71 IgG[1] | 100 μg/mL | 51 | 63 | 60 |
| 2E71 IgG | 10 μg/mL | 41 | 62 | 52 |
| 2E71 IgG | 1 μg/mL | 35.5 | 59 | 48 |
| 2E71 IgG | 0.1 μg/mL | 30 | 43 | 32 |
| 2E71 IgG | 0.01 μg/mL | 14.5 | 15 | 17.5 |
| 3E71 IgG[1] | 100 μg/mL | 49 | 51 | 65 |
| 3E71 IgG | 10 μg/mL | 37 | 51 | 50 |
| 3E71 IgG | 1 μg/mL | 37 | 45 | 40 |

TABLE 5-continued

Inhibition of $^{125}$I-labelled TSH, $^{125}$I-M22 IgG and $^{125}$I-5C9 IgG binding to TSHR coated tubes by different concentrations of mouse MAbs to the TSHR

| Test sample | | | $^{125}$I-TSH (% inhib) | $^{125}$I-M22 IgG (% inhib) | $^{125}$I-5C9 IgG (% inhib) |
|---|---|---|---|---|---|
| 3E71 IgG | 0.1 | μg/mL | 21.5 | 28 | 21 |
| 3E71 IgG | 0.01 | μg/mL | 12 | 15 | 3 |
| 14D3 IgG[1] | 100 | μg/mL | 57 | 62 | 63 |
| 14D3 IgG | 10 | μg/mL | 52 | 60 | 50.5 |
| 14D3 IgG | 1 | μg/mL | 37 | 37 | 35 |
| 14D3 IgG | 0.1 | μg/mL | 12.5 | 15 | 10 |
| 14D3 IgG | 0.01 | μg/mL | 4 | 3 | 1 |
| 16E5 IgG[1] | 100 | μg/mL | 48 | 53 | 59 |
| 16E5 IgG | 10 | μg/mL | 44 | 51 | 53 |
| 16E5 IgG | 1 | μg/mL | 39 | 40 | 47 |
| 16E5 IgG | 0.1 | μg/mL | 26 | 22 | 34 |
| 16E5 IgG | 0.01 | μg/mL | 9 | 12 | 20 |
| 17D2 IgG[1] | 100 | μg/mL | 56 | 49 | 55 |
| 17D2 IgG | 10 | μg/mL | 43 | 39 | 43 |
| 17D2 IgG | 1 | μg/mL | 24 | 24 | 26 |
| 17D2 IgG | 0.1 | μg/mL | 7 | 13 | 11 |
| 17D2 IgG | 0.01 | μg/mL | 3 | 1 | 3 |
| M22 IgG | 100 | μg/mL | 95 | 95 | 88 |
| M22 IgG | 10 | μg/mL | 95 | 94 | 89 |
| M22 IgG | 1 | μg/mL | 94 | 93 | 87 |
| M22 IgG | 0.1 | μg/mL | 77 | 79 | 72 |
| M22 IgG | 0.01 | μg/mL | 22 | 32 | 24 |
| 9D33 IgG[2] | 100 | μg/mL | 69 | 61 | 70 |
| 9D33 IgG | 10 | μg/mL | 65 | 60 | 60 |
| 9D33 IgG | 1 | μg/mL | 55 | 48 | 48 |
| 9D33 IgG | 0.1 | μg/mL | 31 | 27 | 29 |
| 9D33 IgG | 0.01 | μg/mL | 8 | 13 | 13 |
| 2G4 IgG[3] | 100 | μg/mL | 3 | 3 | 6 |
| 2G4 IgG | 10 | μg/mL | 3 | 4 | 10 |
| 2G4 IgG | 1 | μg/mL | 0 | 0 | 8 |
| 2G4 IgG | 0.1 | μg/mL | 4 | 6 | 4 |
| 2G4 IgG | 0.01 | μg/mL | 0 | 0 | 0 |
| 2B4 IgG[4] | 100 | μg/mL | 88.5 | 30 | 72 |
| 2B4 IgG | 10 | μg/mL | 85 | 19 | 48 |
| 2B4 IgG | 1 | μg/mL | 82 | 9 | 42 |
| 2B4 IgG | 0.1 | μg/mL | 56 | 12 | 23 |
| 2B4 IgG | 0.01 | μg/mL | 13.5 | 1 | 8 |
| 8E3 IgG[4] | 100 | μg/mL | 82.5 | 27 | 65 |
| 8E3 IgG | 10 | μg/mL | 72 | 18 | 42 |
| 8E3 IgG | 1 | μg/mL | 53 | 8 | 23 |
| 8E3 IgG | 0.1 | μg/mL | 17 | 0.5 | 9 |
| 8E3 IgG | 0.01 | μg/mL | 5 | 0 | 0 |
| 4E2 IgG[4] | 100 | μg/mL | 76 | 24 | 32 |
| 4E2 IgG | 10 | μg/mL | 74 | 21 | 32 |
| 4E2 IgG | 1 | μg/mL | 57 | 15 | 20 |
| 4E2 IgG | 0.1 | μg/mL | 25 | 2 | 11 |
| 4E2 IgG | 0.01 | μg/mL | 4 | 1 | 5 |
| 1D5 IgG[4] | 100 | μg/mL | 77 | 26 | 26 |
| 1D5 IgG | 10 | μg/mL | 72 | 20 | 20 |
| 1D5 IgG | 1 | μg/mL | 55 | 8 | 13 |
| 1D5 IgG | 0.1 | μg/mL | 23 | 0 | 3 |
| 1D5 IgG | 0.01 | μg/mL | 4 | 0 | 0 |
| 7C4 IgG[4] | 100 | μg/mL | 78 | 24 | 51 |
| 7C4 IgG | 10 | μg/mL | 76 | 22 | 35 |
| 7C4 IgG | 1 | μg/mL | 72 | 22 | 36 |
| 7C4 IgG | 0.1 | μg/mL | 38 | 7 | 19 |
| 7C4 IgG | 0.01 | μg/mL | 9 | 6 | 6 |
| 3E6 IgG[4] | 100 | μg/mL | 84 | 46 | 55 |
| 3E6 IgG | 10 | μg/mL | 79 | 31 | 40 |
| 3E6 IgG | 1 | μg/mL | 71 | 16 | 29 |
| 3E6 IgG | 0.1 | μg/mL | 28 | 5 | 9 |
| 3E6 IgG | 0.01 | μg/mL | 3 | 0 | 6 |
| 1C52 IgG[4] | 100 | μg/mL | 64 | 22 | 30 |
| 1C52 IgG | 10 | μg/mL | 39 | 9 | 15 |
| 1C52 IgG | 1 | μg/mL | 22 | 5 | 15 |
| 1C52 IgG | 0.1 | μg/mL | 5 | 4 | 11 |
| 1C52 IgG | 0.01 | μg/mL | 0 | 2 | 10 |
| 7B72 IgG[4] | 100 | μg/mL | 88 | 32 | 39 |
| 7B72 IgG | 10 | μg/mL | 77 | 21 | 27 |
| 7B72 IgG | 1 | μg/mL | 50 | 14 | 22 |
| 7B72 IgG | 0.1 | μg/mL | 16 | 2 | 13 |
| 7B72 IgG | 0.01 | μg/mL | 8 | 1 | 4 |
| 8E2 IgG[5] | 100 | μg/mL | 52 | 52 | 32 |
| 8E2 IgG | 10 | μg/mL | 24.5 | 24 | 12 |

TABLE 5-continued

Inhibition of $^{125}$I-labelled TSH, $^{125}$I-M22 IgG and $^{125}$I-5C9 IgG binding to TSHR coated tubes by different concentrations of mouse MAbs to the TSHR

| Test sample | | $^{125}$I-TSH (% inhib) | $^{125}$I-M22 IgG (% inhib) | $^{125}$I-5C9 IgG (% inhib) |
|---|---|---|---|---|
| 8E2 IgG | 1 μg/mL | 8 | 3 | 1 |
| 8E2 IgG | 0.1 μg/mL | 13 | 1 | 8 |
| 8E2 IgG | 0.01 μg/mL | 0 | 0 | 13 |
| 18C5 IgG[6] | 100 μg/mL | 57 | 50 | 51 |
| 18C5 IgG | 10 μg/mL | 17 | 14 | 24 |
| 18C5 IgG | 1 μg/mL | 3.5 | 2 | 17 |
| 18C5 IgG | 0.1 μg/mL | 3 | 0 | 13 |
| 18C5 IgG | 0.01 μg/mL | 0.7 | 0 | 14 |
| 2G2 IgG[7] | 100 μg/mL | 0.1 | 0 | 11 |
| 2G2 IgG | 10 μg/mL | 3 | 0.6 | 10 |
| 2G2 IgG | 1 μg/mL | 6 | 1.5 | 12 |
| 2G2 IgG | 0.1 μg/mL | 2 | 0.2 | 9 |
| 2G2 IgG | 0.01 μg/mL | 2 | 1.4 | 11 |

Antibodies were diluted in a pool of healthy blood donor sera (HBD pool).

$$\% \text{ inhibition} = 100 - \left(\frac{A}{B} \times 100\right)$$

where A = % binding in the presence of test sample; B = % binding in the presence of HBD pool.
[1] mouse TSHR MAb with thyroid stimulating activity
[2] mouse TSHR MAb which blocks both TSH and TRAb mediated stimulation of cyclic AMP production (see Table 2)
[3] human MAb to thyroid peroxidase MAb (negative control)
[4] mouse TSHR MAb with TSH blocking activity (recognises an epitope formed by TSHR amino acids 381-385)
[5] mouse TSHR MAb with TSH blocking activity (recognises an epitope formed by TSHR amino acids 36-42)
[6] mouse TSHR MAb with TSH blocking activity (recognises an epitope formed by TSHR amino acids 246-260)
[7] mouse Tg MAb (negative control)

In the presence of HBD pool, approximately 13%, 24% and 15% of $^{125}$I-labelled 5C9 IgG, M22 IgG and TSH respectively bound to the TSHR coated tubes.

TABLE 6a

Effect of 5C9 IgG on stimulation of cyclic AMP production in CHO cells expressing human TSHR by TRAb in patient sera

| Test sample | Cyclic AMP (fmol/cell well mean ± SD; n = 3) |
|---|---|
| Experiment 1a | |
| Cyclic AMP assay buffer only | 378 ± 21 |
| HBD pool only | 352 ± 38 |
| HBD pool + 2G4 IgG | 316 ± 54 |
| HBD pool + 5C9 IgG | 136 ± 46 |
| T1 only | 13734 ± 580 |
| T1 + 2G4 IgG | 10928 ± 740 |
| T1 + 5C9 IgG | 142 ± 4 |
| T2 only | 1716 ± 185 |
| T2 + 2G4 IgG | 1362 ± 190 |
| T2 + 5C9 IgG | 146 ± 4 |
| T3 only | 11722 ± 1280 |
| T3 + 2G4 IgG | 11948 ± 3200 |
| T3 + 5C9 IgG | 5660 ± 790 |
| T4 only | 6388 ± 820 |
| T4 + 2G4 IgG | 6022 ± 710 |
| T4 + 5C9 IgG | 188 ± 65 |
| T5 only | 3084 ± 990 |
| T5 + 2G4 IgG | 2152 ± 240 |
| T5 + 5C9 IgG | 152 ± 15 |
| T6 only | 14802 ± 1475 |
| T6 + 2G4 IgG | 10878 ± 675 |
| T6 + 5C9 IgG | 232 ± 25 |
| Experiment 1b | |
| Cyclic AMP assay buffer only | 434 ± 52 |
| HBD pool only | 518 ± 216 |
| HBD pool + 2G4 IgG | 378 ± 34 |
| HBD pool + 5C9 IgG | 178 ± 47 |
| T7 only | 7388 ± 1250 |
| T7 + 2G4 IgG | 5696 ± 715 |
| T7 + 5C9 IgG | ud |
| T8 only | 1736[1] |
| T8 + 2G4 IgG | 1392[1] |
| T8 + 5C9 IgG | ud |
| T9 only | 5052[1] |
| T9 + 2G4 IgG | 5000[1] |
| T9 + 5C9 IgG | ud |
| Experiment 1c | |
| Cyclic AMP assay buffer only | 366 ± 316 |
| HBD pool only | 646 ± 62 |
| HBD pool + 2G4 IgG | 496 ± 42 |
| HBD pool + 5C9 IgG | 294 ± 92 |
| T13 only | 4030 ± 1146 |
| T13 + 2G4 IgG | 3330 ± 63 |
| T13 + 5C9 IgG | 540 ± 36 |
| T14 only | 5490 ± 197 |
| T14 + 2G4 IgG | 4470 ± 1867 |
| T14 + 5C9 IgG | 510 ± 146 |
| T15 only | 2130 ± 387 |
| T15 + 2G4 IgG | 2380 ± 320 |
| T15 + 5C9 IgG | ud |
| T16 only | 4990 ± 155 |
| T16 + 2G4 IgG | 5270 ± 941 |
| T16 + 5C9 IgG | ud |
| T17 only | 4410 ± 470 |
| T17 + 2G4 IgG | 4460 ± 288 |
| T17 + 5C9 IgG | ud |
| T18 only | 910 ± 126 |
| T18 + 2G4 IgG | 830 ± 21 |
| T18 + 5C9 IgG | ud |
| Experiment 1d | |
| Cyclic AMP assay buffer only | 487 ± 75 |
| HBD pool only | 285 ± 71 |
| HBD pool + 2G4 IgG | 311 ± 68 |

TABLE 6a-continued

Effect of 5C9 IgG on stimulation of cyclic AMP production in CHO cells expressing human TSHR by TRAb in patient sera

| Test sample | Cyclic AMP (fmol/cell well mean ± SD; n = 3) |
|---|---|
| HBD pool + 5C9 IgG | 108 ± 33 |
| T11 only | 4052 ± 233 |
| T11 + 2G4 IgG | 4659 ± 1260 |
| T11 + 5C9 IgG | 154 ± 33 |
| T12 only | 4058 ± 721 |
| T12 + 2G4 IgG | 5556 ± 593 |
| T12 + 5C9 IgG | 145 ± 24 | ud = undetectable
[1] = duplicate determination
HBD pool is a pool of healthy blood donor serum; 1:10 dilution in cyclic AMP assay buffer was used in these experiments.
T1-T9 and T11-T18 are sera which stimulate cyclic AMP production in CHO cells expressing the TSHR. T1-T9 and T11-T18 were tested diluted 1:10 in cyclic AMP assay buffer
2G4 is a human monoclonal antibody to thyroid peroxidase (negative control).
2G4 IgG and 5C9 IgG were tested at 100 µg/mL.

TABLE 6b

Dose response effects of 5C9 IgG and 9D33 IgG on stimulation of cyclic AMP production in CHO cells expressing human TSHR by TRAb in patient sera Experiment 2

| Test samples | Cyclic AMP (fmol/cell well mean ± SD; n = 3) |
|---|---|
| Cyclic AMP assay buffer only | 707 ± 147 |
| HBD pool only | 503 ± 80 |
| T1 only | 20336 ± 1539 |
| 100 µg/mL 2G4 IgG (negative control IgG) only | 1207 ± 123 |
| T1 + 100 µg/mL 2G4 IgG | 22078 ± 2546 |
| T1 + 10 µg/mL 2G4 IgG | 18868 ± 1806 |
| T1 + 1 µg/mL 2G4 IgG | 19025 ± 1450 |
| T1 + 0.1 µg/mL 2G4 IgG | 16659 ± 1031 |
| T1 + 0.01 µg/mL 2G4 IgG | 20876 ± 1887 |
| T1 + 0.001 µg/mL 2G4 IgG | 18134 ± 2126 |
| 100 µg/mL 9D33 IgG only | 721 ± 183 |
| T1 + 100 µg/mL 9D33 IgG | 1061 ± 104 |
| T1 + 10 µg/mL 9D33 IgG | 1464 ± 191 |
| T1 + 1 µg/mL 9D33 IgG | 4990 ± 1670 |
| T1 + 0.1 µg/mL 9D33 IgG | 17867 ± 2220 |
| T1 + 0.01 µg/mL 9D33 IgG | 19943 ± 1834 |
| T1 + 0.001 µg/mL 9D33 IgG | 21648 ± 502 |
| 100 µg/mL 5C9 IgG only | 301 ± 38 |
| T1 + 100 µg/mL 5C9 IgG | 724 ± 28 |
| T1 + 10 µg/mL 5C9 IgG | 1119 ± 348 |
| T1 + 1 µg/mL 5C9 IgG | 2428 ± 594 |
| T1 + 0.1 µg/mL 5C9 IgG | 16152 ± 3577 |
| T1 + 0.01 µg/mL 5C9 IgG | 20314 ± 279 |
| T1 + 0.001 µg/mL 5C9 IgG | 16868 ± 912 |

T1 is a patient serum sample which stimulates cyclic AMP production in CHO cells expressing the TSHR; 1:10 dilution in cyclic AMP assay buffer was used in these experiments.
2G4 is a human monoclonal antibody to thyroid peroxidase (negative control).
9D33 is a mouse monoclonal antibody to the TSHR which blocks both TSH and TRAb stimulated cyclic AMP production (see Table 2).

TABLE 6c

Dose response effects of 5C9 IgG on stimulation of cyclic AMP production in CHO cells expressing human TSHR by patient sera TRAb Experiment 3

| Test samples | Cyclic AMP (fmol/cell well mean ± SD; n = 3) |
|---|---|
| Cyclic AMP assay buffer only | 757 ± 138 |
| HBD pool only | 512 ± 76 |
| T6 only | 14216 ± 3985 |
| 100 µg/mL 9D33 IgG only | 729 ± 31 |
| T6 + 100 µg/mL 9D33 IgG | 1052 ± 702 |
| T6 + 10 µg/mL 9D33 IgG | 2256 ± 1088 |
| T6 + 1 µg/mL 9D33 IgG | 5447 ± 313 |
| T6 + 0.1 µg/mL 9D33 IgG | 8700 ± 665 |
| T6 + 0.01 µg/mL 9D33 IgG | 10290 ± 495 |
| T6 + 0.001 µg/mL 9D33 IgG | 10296[1] |
| 100 µg/mL 5C9 IgG only | 360 ± 38 |
| T6 + 100 µg/mL 5C9 IgG | 295 ± 30 |
| T6 + 10 µg/mL 5C9 IgG | 1027 ± 368 |
| T6 + 1 µg/mL 5C9 IgG | 2368 ± 528 |
| T6 + 0.1 µg/mL 5C9 IgG | 9533 ± 1679 |
| T6 + 0.01 µg/mL 5C9 IgG | 13883 ± 1718 |
| T6 + 0.001 µg/mL 5C9 IgG | 11843 ± 1241 |

[1] single determination
See Tables 6a and 6b for explanatory footnotes.

TABLE 6d

Dose response effects of 5C9 IgG on stimulation of cyclic AMP production in CHO cells expressing human TSHR by TRAb in patient sera

| Sample | Cyclic AMP (fmol/cell well mean ± SD; n = 3) |
|---|---|
| Cyclic AMP assay buffer only | 622 ± 79 |
| HBD pool only | 479 ± 53 |
| T3 only | 14023 ± 2487 |
| 100 µg/mL 2G4 IgG only | 745 ± 136 |
| T3 + 100 µg/mL 2G4 IgG | 12086 ± 2613 |
| T3 + 10 µg/mL 2G4 IgG | 12862 ± 250 |
| T3 + 1 µg/mL 2G4 IgG | 12931 ± 891 |
| T3 + 0.1 µg/mL 2G4 IgG | 13853 ± 1589 |
| T3 + 0.01 µg/mL 2G4 IgG | 11939 ± 131 |
| T3 + 0.001 µg/mL 2G4 IgG | 13650 ± 1679 |
| 100 µg/mL 9D33 IgG only | 616 ± 111 |
| T3 + 100 µg/mL 9D33 IgG | 1597 ± 323 |
| T3 + 10 µg/mL 9D33 IgG | 4262 ± 367 |
| T3 + 1 µg/mL 9D33 IgG | 7385 ± 554 |
| T3 + 0.1 µg/mL 9D33 IgG | 11960 ± 1390 |
| T3 + 0.01 µg/mL 9D33 IgG | 12178 ± 1676 |
| T3 + 0.001 µg/mL 9D33 IgG | 12159 ± 2970 |
| 100 µg/mL 5C9 IgG only | 212 ± 40 |
| T3 + 100 µg/mL 5C9 IgG | 6136 ± 558 |
| T3 + 10 µg/mL 5C9 IgG | 7806 ± 793 |
| T3 + 1 µg/mL 5C9 IgG | 8075 ± 610 |
| T3 + 0.1 µg/mL 5C9 IgG | 10414 ± 1094 |
| T3 + 0.01 µg/mL 5C9 IgG | 13743 ± 1687 |
| T3 + 0.001 µg/mL 5C9 IgG | 11641 ± 2168 |

See Tables 6a and 6b for explanatory footnotes.

TABLE 6e

Dose response effects of 5C9 IgG on stimulation of cyclic AMP production in CHO cells expressing human TSHR by TRAb patient sera

| Sample | Cyclic AMP (fmol/cell well mean ± SD; n = 3) |
|---|---|
| Cyclic AMP assay buffer only | 616 ± 161 |
| HBD pool only | 312 ± 56 |
| T19 only | 6014 ± 280 |
| 100 µg/mL 2G4 IgG only | 1058 ± 75 |
| T19 + 100 µg/mL 2G4 IgG | 7142 ± 215 |
| T19 + 10 µg/mL 2G4 IgG | 6182 ± 46 |
| T19 + 1 µg/mL 2G4 IgG | 7280 ± 1052 |
| T19 + 0.1 µg/mL 2G4 IgG | 7275 ± 145 |
| T19 + 0.01 µg/mL 2G4 IgG | 6820 ± 729 |
| T19 + 0.001 µg/mL 2G4 IgG | 7620 ± 870 |
| 100 µg/mL 9D33 IgG only | 592 ± 168 |

TABLE 6e-continued

Dose response effects of 5C9 IgG on stimulation of cyclic AMP production in CHO cells expressing human TSHR by TRAb patient sera

| Sample | Cyclic AMP (fmol/cell well mean ± SD; n = 3) |
|---|---|
| T19 + 100 µg/mL 9D33 IgG | 550 ± 65 |
| T19 + 10 µg/mL 9D33 IgG | 448 ± 76 |
| T19 + 1 µg/mL 9D33 IgG | 404 ± 36 |
| T19 + 0.1 µg/mL 9D33 IgG | 2394[1] |
| T19 + 0.01 µg/mL 9D33 IgG | 5765[1] |
| T19 + 0.001 µg/mL 9D33 IgG | 7088 ± 668 |
| 100 µg/mL 5C9 IgG only | 186[2] |
| T19 + 100 µg/mL 5C9 IgG | 220 ± 90 |
| T19 + 10 µg/mL 5C9 IgG | 275 ± 150 |
| T19 + 1 µg/mL 5C9 IgG | 187 ± 34 |
| T19 + 0.1 µg/mL 5C9 IgG | 375 ± 129 |
| T19 + 0.01 µg/mL 5C9 IgG | 5747 ± 411 |
| T19 + 0.001 µg/mL 5C9 IgG | 6467[1] |

[1]mean of duplicate sample
[2]single determination
See Tables 6a and 6b for explanatory footnotes.

TABLE 6f

Dose response effects of 5C9 IgG on stimulation of cyclic AMP production in CHO cells expressing human TSHR by TRAb in patient sera

| Sample | Cyclic AMP (fmol/cell well mean ± SD; n = 3) |
|---|---|
| Cyclic AMP assay buffer only | 255 ± 40 |
| HBD pool only | 200 ± 82 |
| T20 only | 4764 ± 732 |
| 100 µg/mL 2G4 IgG only | 835 ± 94 |
| T20 + 100 µg/mL 2G4 IgG | 6684 ± 931 |
| T20 + 10 µg/mL 2G4 IgG | 4571 ± 776 |
| T20 + 1 µg/mL 2G4 IgG | 5744 ± 727 |
| T20 + 0.1 µg/mL 2G4 IgG | 4323 ± 849 |
| T20 + 0.01 µg/mL 2G4 IgG | 6396 ± 1314 |
| T20 + 0.001 µg/mL 2G4 IgG | 6789 ± 893 |
| 100 µg/mL 9D33 IgG only | 382 ± 142 |
| T20 + 100 µg/mL 9D33 IgG | 287 ± 164 |
| T20 + 10 µg/mL 9D33 IgG | 204 ± 49 |
| T20 + 1 µg/mL 9D33 IgG | 980[1] |
| T20 + 0.1 µg/mL 9D33 IgG | 5362 ± 574 |
| T20 + 0.01 µg/mL 9D33 IgG | 5389 ± 1139 |
| T20 + 0.001 µg/mL 9D33 IgG | 7514 ± 785 |
| 100 µg/mL 5C9 IgG only | 224 ± 109 |
| T20 + 100 µg/mL 5C9 IgG | NT |
| T20 + 10 µg/mL 5C9 IgG | NT |
| T20 + 1 µg/mL 5C9 IgG | 181[1] |
| T20 + 0.1 µg/mL 5C9 IgG | 2184 ± 1078 |
| T20 + 0.01 µg/mL 5C9 IgG | 6486 ± 436 |
| T20 + 0.001 µg/mL 5C9 IgG | 4856[1] |

[1]mean of duplicate sample
NT = not tested
See Tables 6a and 6b for explanatory footnotes.

TABLE 6g

Dose response effects of 5C9 IgG on stimulation of cyclic AMP production in CHO cells expressing human TSHR by TRAb in patient sera

| Sample | Cyclic AMP (fmol/cell well mean ± SD; n = 3) |
|---|---|
| Cyclic AMP assay buffer only | 466 ± 65 |
| HBD pool only | 390 ± 118 |
| T21 only | 9781 ± 1672 |
| 100 µg/mL 2G4 IgG only | 999 ± 55 |
| T21 + 100 µg/mL 2G4 IgG | 10848 ± 373 |
| T21 + 10 µg/mL 2G4 IgG | 10355 ± 469 |
| T21 + 1 µg/mL 2G4 IgG | 10831 ± 140 |
| T21 + 0.1 µg/mL 2G4 IgG | 12215 ± 793 |
| T21 + 0.01 µg/mL 2G4 IgG | 13014 ± 855 |
| T21 + 0.001 µg/mL 2G4 IgG | 10500 ± 162 |
| 100 µg/mL 9D33 IgG only | 534 ± 89 |
| T21 + 100 µg/mL 9D33 IgG | 442 ± 32 |
| T21 + 10 µg/mL 9D33 IgG | 605 ± 254 |
| T21 + 1 µg/mL 9D33 IgG | 1383 ± 66 |
| T21 + 0.1 µg/mL 9D33 IgG | 8719 ± 389 |
| T21 + 0.01 µg/mL 9D33 IgG | 10772 ± 799 |
| T21 + 0.001 µg/mL 9D33 IgG | 10229 ± 714 |
| 100 µg/mL 5C9 IgG only | 253 ± 25 |
| T21 + 100 µg/mL 5C9 IgG | 210 ± 60 |
| T21 + 10 µg/mL 5C9 IgG | 303 ± 107 |
| T21 + 1 µg/mL 5C9 IgG | 418 ± 65 |
| T21 + 0.1 µg/mL 5C9 IgG | 7483 ± 415 |
| T21 + 0.01 µg/mL 5C9 IgG | 10441 ± 122 |
| T21 + 0.001 µg/mL 5C9 IgG | 11281 ± 911 |

See Tables 6a and 6b for explanatory footnotes.

TABLE 7a

TSH induced cyclic AMP production in CHO cells expressing wild type TSHR and TSHR with Lys58 mutated to Alanine. Effect of different dilutions of 5C9 IgG

| Test sample | Cyclic AMP produced (fmol/cell well; mean ± SD, n = 3) | | Mutated/wild type (%) |
|---|---|---|---|
| | Wild type TSHR | Mutated TSHR | |
| Cyclic AMP assay buffer only | 315 ± 39 | 822 ± 52 | 260 |
| TSH only | 10730 ± 1737 | 13228 ± 1428 | 123 |
| 2G4 10 µg/mL + TSH | 11707 ± 2291 | 12883 ± 2107 | 110 |
| 2G4 100 µg/mL + TSH | 9640 ± 1664 | 10148 ± 3680 | 105 |
| 5C9 0.01 µg/mL + TSH | 7341 ± 343 | 7913 ± 880 | 108 |
| 5C9 0.1 µg/mL + TSH | 4635 ± 257 | 4815[1] | 104 |
| 5C9 1.0 µg/mL + TSH | 918 ± 159 | 1794 ± 308 | 195 |
| 5C9 10 µg/mL + TSH | 351 ± 187 | 955 ± 405 | 272 |
| 5C9 100 µg/mL + TSH | 528 ± 363 | 1001 ± 306 | 190 |
| 5C9 100 µg/mL only | 47 ± 15 | <25 | — |

[1]mean of duplicate determinations
pTSH concentration = 3 ng/mL
All dilutions in cyclic AMP assay buffer
2G4 is a human monoclonal antibody to thyroid peroxidase (negative control for 5C9).

TABLE 7b

TSH induced cyclic AMP production in CHO cells expressing wild type TSHR and TSHR with Ile60 mutated to Alanine. Effect of different dilutions of 5C9 IgG

| Test sample | Cyclic AMP produced (fmol/cell well; mean ± SD, n = 3) | | Mutated/wild type (%) |
|---|---|---|---|
| | Wild type TSHR | Mutated TSHR | |
| Cyclic AMP assay buffer only | 470 ± 92 | 837 ± 78 | 114 |
| TSH only | 18654[1] | 22935 ± 2542 | 123 |
| 2G4 10 µg/mL + TSH | 17555[1] | 22960 ± 4312 | 131 |
| 2G4 100 µg/mL + TSH | 18654 ± 3979 | 24488 ± 4501 | 131 |
| 5C9 0.01 µg/mL + TSH | 8018 ± 276 | 18952 ± 1811 | 236 |
| 5C9 0.1 µg/mL + TSH | 7097 ± 613 | 11609 ± 1415 | 164 |
| 5C9 1.0 µg/mL + TSH | 1568 ± 133 | 3290 ± 64 | 210 |
| 5C9 10 µg/mL + TSH | 1772 ± 632 | 1211 ± 343 | 68 |

TABLE 7b-continued

TSH induced cyclic AMP production in CHO cells expressing wild type TSHR and TSHR with Ile60 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| 5C9 100 μg/mL + TSH | 1733 ± 132 | 3134 ± 794 | 181 |
| 5C9 100 μg/mL only | 61 ± 8 | 260 ± 43 | 426 |

See Table 7a for explanatory footnotes.

TABLE 7c

TSH induced cyclic AMP production in CHO cells expressing wild type TSHR and TSHR with Arg80 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 775 ± 66 | 1165 ± 32 | 150 |
| TSH only | 12467 ± 510 | 12930 ± 179 | 104 |
| 2G4 10 μg/mL + TSH | 13600 ± 1555 | 14849 ± 462 | 109 |
| 2G4 100 μg/mL + TSH | 11726 ± 177 | 13539 ± 314 | 115 |
| 5C9 0.01 μg/mL + TSH | 14410 ± 1331 | 14273 ± 1845 | 99 |
| 5C9 0.1 μg/mL + TSH | 11256 ± 1627 | 9278 ± 837 | 82 |
| 5C9 1.0 μg/mL + TSH | 6704 ± 791 | 1358 ± 500 | 20 |
| 5C9 10 μg/mL + TSH | 2107 ± 264 | 1163 ± 415 | 55 |
| 5C9 100 μg/mL + TSH | 2234 ± 540 | 518 ± 133 | 23 |
| 5C9 100 μg/mL only | 244 ± 92 | 494 ± 163 | 202 |

See Table 7a for explanatory footnotes.

TABLE 7d

TSH induced cyclic AMP production in CHO cells expressing wild type TSHR and TSHR with Arg80 mutated to Aspartic acid. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 548 ± 67 | 637 ± 96 | 116 |
| TSH only | 13598 ± 3445 | 19400 ± 1684 | 143 |
| 2G4 10 μg/mL + TSH | 14795 ± 2776 | 19430 ± 1779 | 131 |
| 2G4 100 μg/mL + TSH | 15500 ± 897 | 16003 ± 237 | 103 |
| 5C9 0.01 μg/mL + TSH | 13082[1] | 21021 ± 2838 | 161 |
| 5C9 0.1 μg/mL + TSH | 6326 ± 358 | 4420 ± 182 | 70 |
| 5C9 1.0 μg/mL + TSH | 2635 ± 326 | 1912 ± 101 | 73 |
| 5C9 10 μg/mL + TSH | 1906 ± 146 | 1249 ± 329 | 66 |
| 5C9 100 μg/mL + TSH | 1613 ± 176 | 1274 ± 15 | 79 |
| 5C9 100 μg/mL only | 300 ± 45 | 523 ± 3 | 174 |

See Table 7a for explanatory footnotes.

TABLE 7e

TSH induced cyclic AMP production in CHO cells expressing wild type TSHR and TSHR with Tyr82 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 557 ± 27 | 1219 ± 49 | 219 |
| TSH only | 12674 ± 234 | 15327 ± 2041 | 121 |
| 2G4 10 μg/mL + TSH | 13587 ± 967 | 17585[1] | 129 |
| 2G4 100 μg/mL + TSH | 13518 ± 894 | 15395 ± 1777 | 113 |
| 5C9 0.01 μg/mL + TSH | 13902 ± 1970 | 15737 ± 1442 | 113 |
| 5C9 0.1 μg/mL + TSH | 6250 ± 1143 | 12692 ± 3138 | 203 |
| 5C9 1.0 μg/mL + TSH | 1600 ± 467 | 2955 ± 732 | 185 |
| 5C9 10 μg/mL + TSH | 822 ± 99 | 1646 ± 308 | 200 |
| 5C9 100 μg/mL + TSH | 978 ± 102 | 1028 ± 216 | 105 |
| 5C9 100 μg/mL only | 289 ± 30 | 1427 ± 419 | 494 |

See Table 7a for explanatory footnotes.

TABLE 7f

TSH induced cyclic AMP production in CHO cells expressing wild type TSHR and TSHR with Thr104 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 590 ± 59 | 640 ± 95 | 108 |
| TSH only | 11294 ± 1307 | 14247 ± 3093 | 126 |
| 2G4 10 μg/mL + TSH | 14255 ± 1410 | 13227 ± 1782 | 93 |
| 2G4 100 μg/mL + TSH | 13422 ± 2337 | 15499 ± 2042 | 115 |
| 5C9 0.01 μg/mL + TSH | 12307 ± 1080 | 11733 ± 422 | 95 |
| 5C9 0.1 μg/mL + TSH | 7097 ± 79 | 9506 ± 738 | 134 |
| 5C9 1.0 μg/mL + TSH | 3699 ± 391 | 6196 ± 1075 | 168 |
| 5C9 10 μg/mL + TSH | 1796 ± 417 | 3094 ± 740 | 172 |
| 5C9 100 μg/mL + TSH | 2218 ± 395 | 3110 ± 412 | 140 |
| 5C9 100 μg/mL only | 195 ± 23 | 264 ± 102 | 135 |

See Table 7a for explanatory footnotes.

TABLE 7g

TSH induced cyclic AMP production in CHO cells expressing wild type TSHR and TSHR with Arg109 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 381 ± 28 | 675 ± 50 | 177 |
| TSH only | 13823 ± 5141 | 9769 ± 372 | 71 |
| 2G4 10 μg/mL + TSH | 14428 ± 8959 | 9524 ± 1014 | 66 |
| 2G4 100 μg/mL + TSH | 19307 ± 3130 | 8800 ± 631 | 46 |
| 5C9 0.01 μg/mL + TSH | 10820 ± 1644 | 9651 ± 1066 | 89 |
| 5C9 0.1 μg/mL + TSH | 4011 ± 1290 | 1719 ± 40 | 43 |
| 5C9 1.0 μg/mL + TSH | 1206 ± 88 | 827 ± 157 | 69 |
| 5C9 10 μg/mL + TSH | 706 ± 282 | 827 ± 147 | 117 |
| 5C9 100 μg/mL + TSH | 1230 ± 120 | 561 ± 164 | 46 |
| 5C9 100 μg/mL only | 228 ± 45 | 335 ± 14 | 147 |

See Table 7a for explanatory footnotes.

TABLE 7h

TSH induced cyclic AMP production in CHO cells expressing wild type TSHR and TSHR with Lys129 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 370 ± 97 | 590 ± 17 | 159 |
| TSH only | 15632 ± 2362 | 15502 ± 547 | 99 |
| 2G4 10 µg/mL + TSH | 11344 ± 3278 | 14787 ± 986 | 130 |
| 2G4 100 µg/mL + TSH | 12580 ± 2397 | 14148 ± 1033 | 112 |
| 5C9 0.01 µg/mL + TSH | 10545 ± 161 | 12161 ± 1797 | 115 |
| 5C9 0.1 µg/mL + TSH | 2714 ± 154 | 13257 ± 2414 | 488 |
| 5C9 1.0 µg/mL + TSH | 1008 ± 229 | 12837 ± 1148 | 1274 |
| 5C9 10 µg/mL + TSH | 548 ± 26 | 11175[1] | 2039 |
| 5C9 100 µg/mL + TSH | 491 ± 73 | 15929 ± 1228 | 3244 |
| 5C9 100 µg/mL only | 107 ± 18 | 217 ± 36 | 203 |

See Table 7a for explanatory footnotes.

TABLE 7i

TSH induced cyclic AMP production in CHO cells expressing wild type TSHR and TSHR with Phe134 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 347 ± 88 | 867 ± 129 | 250 |
| TSH only | 17641 ± 2133 | 15497 ± 1691 | 88 |
| 2G4 10 µg/mL + TSH | 13759 ± 116 | 17235 ± 1602 | 125 |
| 2G4 100 µg/mL + TSH | 11224 ± 4039 | 16213 ± 1948 | 144 |
| 5C9 0.01 µg/mL + TSH | 13584 ± 1268 | 15872 ± 1140 | 117 |
| 5C9 0.1 µg/mL + TSH | 8702 ± 1542 | 6368 ± 778 | 73 |
| 5C9 1.0 µg/mL + TSH | 4542 ± 104 | 1944 ± 838 | 43 |
| 5C9 10 µg/mL + TSH | 2394 ± 44 | 1058 ± 189 | 44 |
| 5C9 100 µg/mL + TSH | 1393 ± 128 | 1069 ± 65 | 77 |
| 5C9 100 µg/mL only | 212 ± 6 | 337 ± 60 | 159 |

See Table 7a for explanatory footnotes.

TABLE 7j

TSH induced cyclic AMP production in CHO cells expressing wild type TSHR and TSHR with Asp151 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 508 ± 341 | 1236 ± 88 | 243 |
| TSH only | 11266 ± 76 | 10455 ± 771 | 93 |
| 2G4 10 µg/mL + TSH | 15208 ± 1686 | 10713 ± 1859 | 70 |
| 2G4 100 µg/mL + TSH | 11915 ± 1366 | 10416 ± 3434 | 114 |
| 5C9 0.01 µg/mL + TSH | 11245 ± 1583 | 12616 ± 1295 | 112 |
| 5C9 0.1 µg/mL + TSH | 6949 ± 99 | 9956 ± 983 | 143 |
| 5C9 1.0 µg/mL + TSH | 1388 ± 238 | 6450 ± 2088 | 465 |
| 5C9 10 µg/mL + TSH | 380 ± 108 | 2276 ± 1238 | 599 |
| 5C9 100 µg/mL + TSH | 945 ± 180 | 1535 ± 378 | 162 |
| 5C9 100 µg/mL only | 176 ± 49 | 395 ± 42 | 224 |

See Table 7a for explanatory footnotes.

TABLE 7k

TSH induced cyclic AMP production in CHO cells expressing wild type TSHR and TSHR with Asp151 mutated to Arginine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 703 ± 107 | 768 ± 82 | 109 |
| TSH only | 11131 ± 3208 | 19990 ± 458 | 180 |
| 2G4 10 µg/mL + TSH | 15927 ± 2244 | 18846 ± 3293 | 118 |
| 2G4 100 µg/mL + TSH | 13643 ± 3195 | 21275 ± 1580 | 156 |
| 5C9 0.01 µg/mL + TSH | 12351 ± 5559 | 18254 ± 1877 | 148 |
| 5C9 0.1 µg/mL + TSH | 6694 ± 3111 | 10561 ± 1025 | 158 |
| 5C9 1.0 µg/mL + TSH | 2754 ± 166 | 2591 ± 472 | 94 |
| 5C9 10 µg/mL + TSH | 1217[1] | 1609 ± 69 | 132 |
| 5C9 100 µg/mL + TSH | 1572 ± 515 | 2330 ± 273 | 148 |
| 5C9 100 µg/mL only | 260 ± 156 | 409 ± 88 | 157 |

See Table 7a for explanatory footnotes.

TABLE 7l

M22 induced cyclic AMP production in CHO cells expressing wild type TSHR and TSHR with Asp160 mutated to Lysine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 787 ± 119 | 1252 ± 274 | 159 |
| M22 only | 16750 ± 1515 | 14288 ± 1260 | 85 |
| 2G4 10 µg/mL + M22 | 16188 ± 1463 | 15476 ± 468 | 96 |
| 2G4 100 µg/mL + M22 | 15505 ± 2665 | 12638 ± 819 | 82 |
| 5C9 0.01 µg/mL + M22 | 16719 ± 541 | 15239 ± 445 | 91 |
| 5C9 0.1 µg/mL + M22 | 9385 ± 4006 | 7704 ± 703 | 82 |
| 5C9 1.0 µg/mL + M22 | 821 ± 268 | 963 ± 204 | 117 |
| 5C9 10 µg/mL + M22 | 208 ± 89 | 642 ± 386 | 309 |
| 5C9 100 µg/mL + M22 | 301 ± 182 | 657 ± 87 | 218 |
| 5C9 100 µg/mL only | 429 ± 49 | 458 ± 8 | 107 |
| M22 only (repeat determination) | 16702 ± 2170 | 18892 ± 2113 | 113 |

M22 concentration = 3 ng/mL
See Table 7a for other explanatory footnotes.

TABLE 7m

TSH induced cyclic AMP production in CHO cells expressing wild type TSHR and TSHR with Lys183 mutated to Alanine. Effect of different dilutions of 5C9 IgG

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 642 ± 34 | 1153 ± 236 | 180 |
| TSH only | 22385 ± 532 | 20210 ± 1366 | 90 |
| 2G4 10 µg/mL + TSH | 20148 ± 2625 | 23254 ± 3027 | 115 |
| 2G4 100 µg/mL + TSH | 19926[1] | 22442 ± 2489 | 113 |
| 5C9 0.01 µg/mL + TSH | 17974[1] | 23284 ± 2243 | 130 |
| 5C9 0.1 µg/mL + TSH | 11499 ± 892 | 24289 ± 720 | 211 |
| 5C9 1.0 µg/mL + TSH | 3489 ± 606 | 14586 ± 155 | 418 |
| 5C9 10 µg/mL + TSH | 1234 ± 357 | 7568 ± 605 | 618 |
| 5C9 100 µg/mL + TSH | 1456 ± 838 | 11448 ± 933 | 786 |
| 5C9 100 µg/mL only | 384 ± 19 | 747 ± 230 | 195 |

See Table 7a for explanatory footnotes.

TABLE 7n

TSH induced cyclic AMP production in CHO cells expressing wild type TSHR and TSHR with Lys183 mutated to Aspartic acid. Effect of different dilutions of 5C9 IgG

| Test sample | Cyclic AMP produced (fmol/cell well; mean ± SD, n = 3) Wild type TSHR | Mutated TSHR | Mutated/ wild type (%) |
|---|---|---|---|
| Cyclic AMP assay buffer only | 486 ± 151 | 737 ± 54 | 152 |
| TSH only | 14730 ± 1647 | 17668 ± 597 | 120 |
| 2G4 10 µg/mL + TSH | 14234 ± 1097 | 17133 ± 2281 | 120 |
| 2G4 100 µg/mL + TSH | 14737 ± 1905 | 16071 ± 1188 | 109 |
| 5C9 0.01 µg/mL + TSH | 12911 ± 2357 | 20614 ± 2552 | 160 |
| 5C9 0.1 µg/mL + TSH | 8577 ± 615 | 17344 ± 2898 | 202 |
| 5C9 1.0 µg/mL + TSH | 3424 ± 135 | 12655 ± 835 | 370 |
| 5C9 10 µg/mL + TSH | 1114 ± 112 | 6587 ± 1480 | 591 |
| 5C9 100 µg/mL + TSH | 1720 ± 119 | 9007 ± 1295 | 524 |
| 5C9 100 µg/mL only | <12.5 | 54 ± 8 | — |

See Table 7a for explanatory footnotes.

TABLE 7o

TSH induced cyclic AMP production in CHO cells expressing wild type TSHR and TSHR with Gln235 mutated to Alanine. Effect of different dilutions of 5C9 IgG

| Test sample | Cyclic AMP produced (fmol/cell well; mean ± SD, n = 3) Wild type TSHR | Mutated TSHR | Mutated/ wild type (%) |
|---|---|---|---|
| Cyclic AMP assay buffer only | 478 ± 94 | 713 ± 52 | 149 |
| TSH only | 14882 ± 944 | 15844 ± 922 | 106 |
| 2G4 10 µg/mL + TSH | 17754 ± 3150 | 18900 ± 3098 | 106 |
| 2G4 100 µg/mL + TSH | 12991[1] | 18598 ± 2708 | 143 |
| 5C9 0.01 µg/mL + TSH | 7181 ± 618 | 17535 ± 3692 | 244 |
| 5C9 0.1 µg/mL + TSH | 7784 ± 1111 | 7437 ± 1183 | 96 |
| 5C9 1.0 µg/mL + TSH | 2545 ± 471 | 2416 ± 423 | 95 |
| 5C9 10 µg/mL + TSH | 532 ± 65 | 1023 ± 400 | 192 |
| 5C9 100 µg/mL + TSH | 747 ± 114 | 727 ± 168 | 97 |
| 5C9 100 µg/mL only | 119 ± 28 | 256 ± 86 | 215 |

See Table 7a for explanatory footnotes.

TABLE 7p

TSH induced cyclic AMP production in CHO cells expressing wild type TSHR and TSHR with Arg255 mutated to Alanine. Effect of different dilutions of 5C9 IgG

| Test sample | Cyclic AMP produced (fmol/cell well; mean ± SD, n = 3) Wild type TSHR | Mutated TSHR | Mutated/ wild type (%) |
|---|---|---|---|
| Cyclic AMP assay buffer only | 538 ± 12 | 797 ± 113 | 148 |
| TSH only | 14362 ± 3305 | 15243 ± 2093 | 106 |
| 2G4 10 µg/mL + TSH | 14444 ± 3161 | 19042 ± 1085 | 132 |
| 2G4 100 µg/mL + TSH | 16810 ± 3461 | 17710 ± 4886 | 105 |
| 5C9 0.01 µg/mL + TSH | 6624 ± 1236 | 8124 ± 395 | 123 |
| 5C9 0.1 µg/mL + TSH | 3788 ± 838 | 4137 ± 537 | 109 |
| 5C9 1.0 µg/mL + TSH | 966 ± 150 | 1941 ± 113 | 201 |
| 5C9 10 µg/mL + TSH | 867 ± 100 | 692 ± 152 | 80 |
| 5C9 100 µg/mL + TSH | 1013 ± 247 | 809 ± 248 | 80 |
| 5C9 100 µg/mL only | 32[1] | 248 ± 94 | 775 |

See Table 7a for explanatory footnotes.

TABLE 7q

TSH induced cyclic AMP production in CHO cells expressing wild type TSHR and TSHR with Arg255 mutated to Aspartic acid. Effect of different dilutions of 5C9 IgG

| Test sample | Cyclic AMP produced (fmol/cell well; mean ± SD, n = 3) Wild type TSHR | Mutated TSHR | Mutated/ wild type (%) |
|---|---|---|---|
| Cyclic AMP assay buffer only | 620 ± 33 | 616[1] | 99 |
| TSH only | 17531 ± 1730 | 18081 ± 2439 | 103 |
| 2G4 10 µg/mL + TSH | 19870 ± 2766 | 15519 ± 702 | 78 |
| 2G4 100 µg/mL + TSH | 18265 ± 1999 | 19638 ± 1505 | 108 |
| 5C9 0.01 µg/mL + TSH | 17518 ± 2407 | 15654 ± 148 | 89 |
| 5C9 0.1 µg/mL + TSH | 6604 ± 1552 | 5583 ± 655 | 85 |
| 5C9 1.0 µg/mL + TSH | 3375 ± 227 | 1932 ± 677 | 57 |
| 5C9 10 µg/mL + TSH | 1244 ± 565 | 735 ± 9 | 59 |
| 5C9 100 µg/mL + TSH | 1506 ± 151 | 1414 ± 568 | 94 |
| 5C9 100 µg/mL only | 278 ± 125 | 559 ± 97 | 201 |

See Table 7a for explanatory footnotes.

TABLE 7r

TSH induced cyclic AMP production in CHO cells expressing wild type TSHR and TSHR with Trp258 mutated to Alanine. Effect of different dilutions of 5C9 IgG

| Test sample | Cyclic AMP produced (fmol/cell well; mean ± SD, n = 3) Wild type TSHR | Mutated TSHR | Mutated/ wild type (%) |
|---|---|---|---|
| Cyclic AMP assay buffer only | 354 ± 28 | 382 ± 55 | 108 |
| TSH only | 21023 ± 2104 | 7095 ± 1086 | 33 |
| 2G4 10 µg/mL + TSH | 19564 ± 1076 | 7070 ± 148 | 36 |
| 2G4 100 µg/mL + TSH | 21591 ± 2652 | 6066 ± 336 | 28 |
| 5C9 0.01 µg/mL + TSH | 19471 ± 1456 | 6619 ± 511 | 34 |
| 5C9 0.1 µg/mL + TSH | 10455 ± 1968 | 1944 ± 168 | 19 |
| 5C9 1.0 µg/mL + TSH | 2616 ± 118 | 1127 ± 24 | 43 |
| 5C9 10 µg/mL + TSH | 1192 ± 253 | 357 ± 11 | 30 |
| 5C9 100 µg/mL + TSH | 1316 ± 283 | 484 ± 247 | 37 |
| 5C9 100 µg/mL only | 211 ± 35 | 423 ± 109 | 200 |

See Table 7a for explanatory footnotes.

TABLE 7s

TSH induced cyclic AMP production in CHO cells expressing wild type TSHR and TSHR with Ser281 mutated to Alanine. Effect of different dilutions of 5C9 IgG

| Test sample | Cyclic AMP produced (fmol/cell well; mean ± SD, n = 3) Wild type TSHR | Mutated TSHR | Mutated/ wild type (%) |
|---|---|---|---|
| Cyclic AMP assay buffer only | 496 ± 72 | 1094 ± 132 | 221 |
| TSH only | 13562 ± 3416 | 26450[1] | 195 |
| 2G4 10 µg/mL + TSH | 16805 ± 1139 | 25086 ± 1730 | 149 |
| 2G4 100 µg/mL + TSH | 14334 ± 860 | 27672 ± 3549 | 193 |
| 5C9 0.01 µg/mL + TSH | 13791 ± 3221 | 28966 ± 3443 | 210 |
| 5C9 0.1 µg/mL + TSH | 9071 ± 1696 | 15560 ± 5836 | 172 |
| 5C9 1.0 µg/mL + TSH | 3732 ± 514 | 3550 ± 725 | 95 |
| 5C9 10 µg/mL + TSH | 802 ± 215 | 1551 ± 545 | 193 |
| 5C9 100 µg/mL + TSH | 1078 ± 158 | 1601 ± 720 | 149 |
| 5C9 100 µg only | 201 ± 41 | 785 ± 188 | 391 |

See Table 7a for explanatory footnotes.

TABLE 8

Comparison of serum TRAb assay results obtained with ELISAs based on inhibition of TSH-biotin binding or 5C9 IgG-biotin binding

| Test samples | TSH-biotin reference assay | | | 5C9 IgG-biotin assay | | |
|---|---|---|---|---|---|---|
| | Abs 450 nm | % inhibition | Concentration (U/L) | Abs 450 nm | % inhibition | Concentration (U/L) |
| Assay negative control | 2.143 | 0 | 0 | 2.421 | 0 | 0 |
| Assay calibrators | | | | | | |
| 1 U/L | 1.821 | 15 | 1 | 2.027 | 16 | 1 |
| 2 U/L | 1.564 | 27 | 2 | 1.747 | 28 | 2 |
| 8 U/L | 0.66 | 69 | 8 | 0.532 | 78 | 8 |
| 40 U/L | 0.132 | 94 | 40 | 0.092 | 96 | 40 |
| Assay positive control | 1.273 | 41 | 3.22 | 1.344 | 44 | 3.28 |
| Patient sera | | | | | | |
| A | 2.122 | 1 | 0.14 | 2.209 | 9 | 0.44 |
| B | 1.081 | 50 | 4.24 | 1.029 | 58 | 4.54 |
| C | 0.225 | 90 | 26.03 | 0.173 | 93 | 18.4 |
| D | 2.069 | 3 | 0.24 | 2.27 | 6 | 0.31 |
| E | 1.789 | 16 | 1.12 | 2.189 | 10 | 0.49 |
| F | 1.454 | 32 | 2.43 | 1.791 | 26 | 1.85 |
| G | 1.053 | 51 | 4.41 | 1.123 | 54 | 4.12 |
| H | 1.242 | 42 | 3.37 | 1.309 | 46 | 3.4 |
| I | 0.208 | 90 | 28.01 | 0.174 | 93 | 18.32 |
| Healthy blood donor sera | | | | | | |
| 4276 | 2.182 | −2 | 0 | 2.451 | −1 | 0 |
| 4280 | 2.292 | −7 | 0 | 2.621 | −8 | 0 |
| 4281 | 2.138 | 0 | 0 | 2.529 | −4 | 0 |
| 4282 | 2.204 | −3 | 0 | 2.6 | −7 | 0 |
| 4284 | 2.306 | −8 | 0 | 2.613 | −8 | 0 |
| 4285 | 2.328 | −9 | 0 | 2.756 | −14 | 0 |
| 4286 | 2.34 | −9 | 0 | 2.691 | −11 | 0 |
| 4289 | 2.381 | −11 | 0 | 2.628 | −9 | 0 |

Assay calibrators 40 U/L, 8 U/L, 2 U/L and 1 U/L are dilutions of M22 IgG in a pool of healthy blood donor sera (HBD pool) with activities in U/L of NIBSC 90/672 assessed by inhibition of labelled TSH binding to TSHR coated tubes. Assay negative control is an HBD pool.

TABLE 9

Effects of 5C9 IgG on TSHR stimulation by thyroid stimulating mouse MAbs (mTSMAbs)

| | Cyclic AMP concentration (mean pmol/mL ± SD; n = 3) in CHO cells expressing wild type TSHR after addition of TSMAb and:- | | |
|---|---|---|---|
| Test Sample[a] | Buffer only | 5C9 IgG 100 μg/mL | 2G4 IgG[b] 100 μg/mL |
| TSMAb 1 1 μg/mL | 18.94 ± 7.4 | 1.24 ± 0.07 | 16.5 ± 1.1 |
| TSMAb 2 1 μg/mL | 9.71 ± 0.96 | 2.26 ± 0.05 | 8.96 ± 1.28 |
| TSMAb 4 10 ng/mL | 34.5 ± 2.04 | 2.20 ± 0.20 | 33.1 ± 1.25 |
| TSMAb 5 100 ng/mL | 27.26 ± 2.14 | 0.85 ± 0.01 | 22.5 ± 2.4 |
| TSMAb 7 100 ng/mL | 9.90 ± 1.52 | 1.26 ± 0.59 | 9.07 ± 0.65 |
| Buffer only | 3.39 ± 1.35 | 1.56 ± 1.84 | 4.32 ± 0.95 |

[a]dilution in cyclic AMP assay buffer
[b]2G4 is a control human monoclonal autoantibody to thyroid peroxidase.

TABLE 10

Effect of 5C9 IgG on TSHR stimulation by different preparations of TSH

| Test sample diluted in cyclic AMP assay buffer | Cyclic AMP concentration (pmol/mL mean ± SD; n = 3) in CHO cells expressing wild type TSHR |
|---|---|
| Experiment 1 | |
| Buffer only | 0.37 ± 0.15 |
| Native human TSH 100 ng/mL only | 36.14 ± 1.83 |
| Native human TSH 100 ng/mL and 0.001 μg/mL 5C9 IgG. | 36.0 ± 6.1 |
| Native human TSH 100 ng/mL and 0.01 μg/mL 5C9 IgG | 18.0 ± 5.4 |
| Native human TSH 100 ng/mL and 0.1 μg/mL 5C9 IgG | 0.20 ± 0.06 |
| Native human TSH 100 ng/mL and 1.0 μg/mL 5C9 IgG | 0.14 ± 0.02 |
| Native human TSH 100 ng/mL and 10 μg/mL 5C9 IgG | 0.11 ± 0.04 |
| Native human TSH 100 ng/mL and 100 μg/mL 5C9 IgG | 0.16 ± 0.03 |
| Recombinant human TSH 100 ng/mL only | 12.73 ± 4.0 |
| Recombinant human TSH 100 ng/mL and 0.001 μg/mL 5C9 IgG. | 13.63 ± 1.7 |
| Recombinant human TSH 100 ng/mL and 0.01 μg/mL 5C9 IgG | 8.13 ± 2.13 |
| Recombinant human TSH 100 ng/mL and 0.1 μg/mL 5C9 IgG | 0.12 ± 0.06 |
| Recombinant human TSH 100 ng/mL and 1.0 μg/mL 5C9 IgG | 0.10 ± 0.03 |

TABLE 10-continued

Effect of 5C9 IgG on TSHR stimulation by different preparations of TSH

| Test sample diluted in cyclic AMP assay buffer | Cyclic AMP concentration (pmol/mL mean ± SD; n = 3) in CHO cells expressing wild type TSHR |
|---|---|
| Recombinant human TSH 100 ng/mL and 10 µg/mL 5C9 IgG | 0.12 ± 0.05 |
| Recombinant human TSH 100 ng/mL and 100 µg/mL 5C9 IgG | 0.19 ± 0.08 |
| Experiment 2 | |
| Buffer only | 0.18 ± 0.08 |
| Native human TSH 100 ng/mL only | 40.8 ± 6.92 |
| Native human TSH 100 ng/mL and 0.001 µg/mL 5C9 IgG. | 37.6 ± 6.35 |
| Native human TSH 100 ng/mL and 0.01 µg/mL 5C9 IgG | 34.4 ± 2.28 |
| Native human TSH 100 ng/mL and 0.1 µg/mL 5C9 IgG | 15.8 ± 1.39 |
| Native human TSH 100 ng/mL and 1.0 µg/mL 5C9 IgG | 0.13 ± 0.03 |
| Native human TSH 100 ng/mL and 10 µg/mL 5C9 IgG | 0.18 ± 0.05 |
| Native human TSH 100 ng/mL and 100 µg/mL 5C9 IgG | 0.21 ± 0.10 |
| Recombinant human TSH 100 ng/mL only | 16.72 ± 2.90 |
| Recombinant human TSH 100 ng/mL and 0.001 µg/mL 5C9 IgG. | 20.0 ± 1.73 |
| Recombinant human TSH 100 ng/mL and 0.01 µg/mL 5C9 IgG | 20.6 ± 1.57 |
| Recombinant human TSH 100 ng/mL and 0.1 µg/mL 5C9 IgG | 7.39 ± 1.74 |
| Recombinant human TSH 100 ng/mL and 1.0 µg/mL 5C9 IgG | 0.07 ± 0.01 |
| Recombinant human TSH 100 ng/mL and 10 µg/mL 5C9 IgG | 0.07 ± 0.01 |
| Recombinant human TSH 100 ng/mL and 100 µg/mL 5C9 IgG | 0.11 ± 0.03 |
| Native porcine TSH 0.3 ng/mL only | 40.2 ± 4.0 |
| Native porcine TSH 0.3 ng/mL and 0.001 µg/mL 5C9 IgG. | 32.7 ± 4.0 |
| Native porcine TSH 0.3 ng/mL and 0.01 µg/mL 5C9 IgG | 28.2 ± 2.04 |
| Native porcine TSH 0.3 ng/mL and 0.1 µg/mL 5C9 IgG | 18.0 ± 1.36 |
| Native porcine TSH 0.3 ng/mL and 1.0 µg/mL 5C9 IgG | 2.14 ± 0.85 |
| Native porcine TSH 0.3 ng/mL and 10 µg/mL 5C9 IgG | 0.20 ± 0.14 |
| Native porcine TSH 0.3 ng/mL and 100 µg/mL 5C9 IgG | 0.18 ± 0.13 |
| Experiment 3 | |
| Buffer only | 2.0 ± 0.8 |
| Native human TSH 100 ng/mL only | 31.1 ± 2.55 |
| Native human TSH 100 ng/mL and 0.001 µg/mL 5C9 IgG. | 36.0 ± 3.27 |
| Native human TSH 100 ng/mL and 0.01 µg/mL 5C9 IgG | 28.4 ± 3.55 |
| Native human TSH 100 ng/mL and 0.1 µg/mL 5C9 IgG | 7.22 ± 3.20 |
| Native human TSH 100 ng/mL and 1.0 µg/mL 5C9 IgG | 0.67 ± 0.46 |
| Native human TSH 100 ng/mL and 10 µg/mL 5C9 IgG | 0.8 ± 0.45 |
| Native human TSH 100 ng/mL and 100 µg/mL 5C9 IgG | 1.35 ± 1.0 |
| Recombinant human TSH 100 ng/mL only | 26.4 ± 3.53 |
| Recombinant human TSH 100 ng/mL and 0.001 µg/mL 5C9 IgG. | 25.6 ± 2.45 |
| Recombinant human TSH 100 ng/mL and 0.01 µg/mL 5C9 IgG | 22.9 ± 7.4 |
| Recombinant human TSH 100 ng/mL and 0.1 µg/mL 5C9 IgG | 1.18 ± 0.49 |
| Recombinant human TSH 100 ng/mL and 1.0 µg/mL 5C9 IgG | 0.81 ± 0.05 |
| Recombinant human TSH 100 ng/mL and 10 µg/mL 5C9 IgG | 0.74 ± 0.42 |
| Recombinant human TSH 100 ng/mL and 100 µg/mL 5C9 IgG | 0.88 ± 0.55 |
| Native porcine TSH 0.3 ng/mL only | 35.7 ± 4.82 |
| Native porcine TSH 0.3 ng/mL and 0.001 µg/mL 5C9 IgG. | 38.2 ± 2.54 |
| Native porcine TSH 0.3 ng/mL and 0.01 µg/mL 5C9 IgG | 26.6 ± 3.22 |
| Native porcine TSH 0.3 ng/mL and 0.1 µg/mL 5C9 IgG | 10.1 ± 1.79 |
| Native porcine TSH 0.3 ng/mL and 1.0 µg/mL 5C9 IgG | 2.28 ± 0.71 |
| Native porcine TSH 0.3 ng/mL and 10 µg/mL 5C9 IgG | 0.68 ± 0.21 |
| Native porcine TSH 0.3 ng/mL and 100 µg/mL 5C9 IgG | 1.03 ± 0.63 |

TABLE 11a

Effects of 5C9 IgG and 9D33 IgG on the constitutive activity of TSHR with an activating mutation S281I

| Test sample diluted in cyclic AMP assay buffer | Cyclic AMP concentration (pmol/mL mean ± SD; n = 3) in CHO cells expressing TSHR S281I |
|---|---|
| Buffer only | 9.90 ± 1.51 |
| 0.001 µg/mL 2G4 IgG[a] | 6.83 ± 0.37 |
| 0.01 µg/mL 2G4 IgG | 7.74 ± 0.78 |
| 0.1 µg/mL 2G4 IgG | 8.58 ± 1.12 |
| 1 µg/mL 2G4 IgG | 8.37 ± 1.10 |
| 0.001 µg/mL 5C9 IgG | 4.31 ± 0.16 |
| 0.01 µg/mL 5C9 IgG | 4.17 ± 0.60 |
| 0.1 µg/mL 5C9 IgG | 3.20 ± 0.63 |
| 1 µg/mL 5C9 IgG | 3.44 ± 0.63 |
| 0.001 µg/mL 9D33 IgG | 5.97 ± 0.94 |
| 0.01 µg/mL 9D33 IgG | 9.27 ± 1.4 |
| 0.1 µg/mL 9D33 IgG | 8.13 ± 0.72 |
| 1 µg/mL 9D33 IgG | 7.33 ± 1.17 |

[a]2G4 is a control human monoclonal antibody to thyroid peroxidase.

TABLE 11b

Effect of 5C9 IgG and 9D33 IgG on the constitutive activity of TSHR with an activating mutation I568T

| Test sample diluted in cyclic AMP assay buffer | Cyclic AMP concentration (pmol/mL mean ± SD; n = 3) in CHO cells expressing TSHR I568T |
|---|---|
| Buffer only | 21.39 ± 5.31 |
| 0.001 µg/mL 2G4 IgG | 19.13 ± 2.77 |
| 0.01 µg/mL 2G4 IgG | 16.67 ± 1.87 |
| 0.1 µg/mL 2G4 IgG | 19.92 ± 0.91 |
| 1 µg/mL 2G4 IgG | 20.52 ± 0.95 |
| 0.001 µg/mL 5C9 IgG | 18.81 ± 1.39 |
| 0.01 µg/mL 5C9 IgG | 9.24 ± 0.83 |
| 0.1 µg/mL 5C9 IgG | 6.02 ± 1.93 |
| 1 µg/mL 5C9 IgG | 5.29 ± 0.75 |
| 0.001 µg/mL 9D33 IgG | 16.58 ± 0.00 |
| 0.01 µg/mL RSR-B2 IgG | 17.03 ± 2.36 |
| 0.1 µg/mL RSR-B2 IgG | 19.96 ± 1.66 |
| 1 µg/mL RSR-B2 IgG | 21.65 ± 1.99 |

TABLE 11c

Effect of 5C9 IgG and 9D33 IgG on the constitutive activity of TSHR with an activating mutation A623I

| Test sample diluted in cyclic AMP assay buffer | Cyclic AMP concentration (pmol/mL mean ± SD; n = 3) in CHO cells expressing TSHR A623I |
|---|---|
| Buffer only | 36.89[a] |
| 0.001 µg/mL 2G4 IgG | 28.46 ± 2.31 |
| 0.01 µg/mL 2G4 IgG | 33.44 ± 1.12 |
| 0.1 µg/mL 2G4 IgG | 30.40 ± 7.93 |
| 1 µg/mL 2G4 IgG | 28.96 ± 2.29 |
| 0.001 µg/mL 5C9 IgG | 26.52 ± 1.33 |
| 0.01 µg/mL 5C9 IgG | 27.03 ± 2.13 |
| 0.1 µg/mL 5C9 IgG | 19.79 ± 0.48 |
| 1 µg/mL 5C9 IgG | 16.43 ± 1.27 |
| 0.001 µg/mL 9D33 IgG | 29.55 ± 3.15 |
| 0.01 µg/mL 9D33 IgG | 27.64 ± 3.49 |
| 0.1 µg/mL 9D33 IgG | 31.78 ± 9.18 |
| 1 µg/mL 9D33 IgG | 40.09 ± 7.73 |

[a]duplicate determination

TABLE 12

Effects of 5C9 plus 9D33 on blocking of pTSH stimulation of cyclic AMP production in CHO cells expressing wild type TSHR.

| Test sample in cyclic AMP assay buffer | Cyclic AMP concentration (pmol/mL mean ± SD; n = 3) |
|---|---|
| Experiment 1 | |
| Buffer only | 1.9 ± 1.0 |
| TSH 3 ng/mL | 48.5 ± 14 |
| 10 µg/mL 9D33 | 2.9 ± 1.0 |
| 10 µg/mL 5C9 | 0.45 ± 0.31 |
| 10 µg/mL 9D33 + 10 µg/mL 5C9 | 1.12 ± 0.4 |
| 10 µg/mL 9D33 + TSH | 23.8 ± 8.7 |
| 10 µg/mL 5C9 + TSH | 3.7 ± 2.7 |
| 10 µg/mL 9D33 + 10 µg/mL 5C9 + TSH | 4.9 (n = 2) |
| 1 µg/mL 9D33 + TSH | 28.7 ± 1.8 |
| 1 µg/mL 5C9 + TSH | 13.9 ± 3.1 |
| 1 µg/mL 9D33 + 1 µg/mL 5C9 + TSH | 12.6 ± 2.5 |
| Experiment 2 | |
| Buffer only | 0.72 ± 0.63 |
| TSH 3 ng/mL | 34.3 ± 3.1 |
| 10 µg/mL 9D33 | 1.6 ± 1.3 |
| 10 µg/mL 5C9 | 0.4 ± 0.4 |
| 10 µg/mL 9D33 + 10 µg/mL 5C9 | 0.03 (n = 1) |
| 10 µg/mL 9D33 + TSH | 9.5 ± 1.7 |
| 10 µg/mL 5C9 + TSH | 3.1 ± 1.0 |
| 10 µg/mL 9D33 + 10 µg/mL 5C9 + TSH | 3.3 ± 2.0 |
| 1 µg/mL 9D33 + TSH | 19.0 ± 3.2 |
| 1 µg/mL 5C9 + TSH | 6.1 ± 0.6 |
| 1 µg/mL 9D33 + 1 µg/mL 5C9 + TSH | 5.9 ± 0.6 |
| Experiment 3 | |
| Buffer only | 0.99 ± 0.03 |
| TSH 3 ng/mL | 51.3 ± 5.0 |
| 100 µg/mL 9D33 | 1.14 ± 0.13 |
| 100 µg/mL 5C9 | 0.50 ± 0.04 |
| 100 µg/mL 9D33 + 100 µg/mL 5C9 | 0.66 ± 0.9 |
| 100 µg/mL 9D33 + TSH | 10.53 ± 0.84 |
| 100 µg/mL 5C9 + TSH | 1.4 ± 0.18 |
| 100 µg/mL 9D33 + 100 µg/mL 5C9 + TSH | 1.3 ± 0.36 |
| 10 µg/mL 9D33 + TSH | 13.5 ± 2.9 |
| 10 µg/mL 5C9 + TSH | 1.9 ± 1.1 |
| 10 µg/mL 9D33 + 10 µg/mL 5C9 + TSH | 1.2 ± 0.1 |
| 1 µg/mL 9D33 + TSH | 27.8 ± 2.2 |
| 1 µg/mL 5C9 + TSH | 5.4 ± 1.8 |
| 1 µg/mL 9D33 + 1 µg/mL 5C9 + TSH | 5.2 ± 0.3 |
| 0.1 µg/mL 9D33 + TSH | 35.1 ± 2.3 |
| 0.1 µg/mL 5C9 + TSH | 18.7 ± 3.4 |
| 0.1 µg/mL 9D33 + 0.1 µg/mL 5C9 + TSH | 14.4 ± 1.0 |
| 0.01 µg/mL 9D33 + TSH | 47.1 ± 1.9 |
| 0.01 µg/mL 5C9 + TSH | 33.9 ± 7.8 |
| 0.01 µg/mL 9D33 + 0.01 µg/mL 5C9 + TSH | 27.8 ± 1.3 |
| Experiment 4 | |
| Buffer only | 1.4 ± 0.5 |
| TSH 0.3 ng/mL | 46.6 ± 12.9 |
| 100 µg/mL 9D33 | 0.99 ± 0.62 |
| 100 µg/mL 5C9 | 0.15 ± 0.12 |
| 100 µg/mL 9D33 + 100 µg/mL 5C9 | 0.41 ± 0.40 |
| 100 µg/mL 9D33 + TSH | 3.53 ± 1.1 |
| 100 µg/mL 5C9 + TSH | 0.29 ± 0.15 |
| 100 µg/mL 9D33 + 100 µg/mL 5C9 + TSH | 0.63 ± 0.38 |
| 10 µg/mL 9D33 + TSH | 4.23 ± 0.81 |
| 10 µg/mL 5C9 + TSH | 0.23 ± 0.08 |
| 10 µg/mL 9D33 + 10 µg/mL 5C9 + TSH | 0.52 ± 0.15 |
| 1 µg/mL 9D33 + TSH | 9.01 ± 0.67 |
| 1 µg/mL 5C9 + TSH | 1.65 ± 0.47 |
| 1 µg/mL 9D33 + 1 µg/mL 5C9 + TSH | 1.21 ± 0.67 |
| 0.1 µg/mL 9D33 + TSH | 20.2 ± 2.2 |
| 0.1 µg/mL 5C9 + TSH | 6.2 ± 1.8 |
| 0.1 µg/mL 9D33 + 0.1 µg/mL 5C9 + TSH | 7.6 ± 1.3 |
| Experiment 5 | |
| Buffer only | 1.83 ± 0.64 |
| TSH 0.3 ng/mL | 17.26 ± 1.5 |
| 10 µg/mL 9D33 | 2.07 ± 0.52 |
| 10 µg/mL 5C9 | 0.38 ± 0.2 |
| 10 µg/mL 9D33 + 10 µg/mL 5C9 | 0.96 ± 0.14 |
| 10 µg/mL 9D33 + TSH | 3.57 ± 0.58 |
| 10 µg/mL 5C9 + TSH | 1.17 ± 0.00 |
| 10 µg/mL 9D33 + 10 µg/mL 5C9 + TSH | 1.58 ± 0.20 |
| 5 µg/mL 9D33 + TSH | 3.71 ± 0.10 |
| 5 µg/mL 5C9 + TSH | 1.21 ± 0.36 |
| 1 µg/mL 9D33 + TSH | 6.38 ± 1.35 |
| 1 µg/mL 5C9 + TSH | 2.57 ± 0.65 |
| 1 µg/mL 9D33 + 1 µg/mL 5C9 + TSH | 1.46 ± 0.59 |
| 0.1 µg/mL 9D33 + TSH | 14.67 ± 4.69 |
| 0.1 µg/mL 5C9 + TSH | 12.43 ± 1.59 |
| 0.1 µg/mL 9D33 + 0.1 µg/mL 5C9 + TSH | 9.99 ± 3.78 |

TABLE 13

Effect of 5C9 plus 9D33 on blocking of M22 Fab mediated stimulation of cyclic AMP production in CHO cells expressing wild type TSHR

| Test sample in cyclic AMP assay buffer | Cyclic AMP concentration (pmol/mL mean ± SD; n = 3) |
|---|---|
| Experiment 1 | |
| Buffer only | 1.45 ± 0.46 |
| M22 3 ng/mL | 49.1 ± 9.8 |
| 100 µg/mL 9D33 | 1.51 ± 0.22 |
| 100 µg/mL 5C9 | 0.35 ± 0.30 |
| 100 µg/mL 9D33 + 100 µg/mL 5C9 | 1.57 ± 0.13 |
| 100 µg/mL 9D33 + M22 | 2.13 ± 0.74 |

TABLE 13-continued

Effect of 5C9 plus 9D33 on blocking of M22 Fab mediated stimulation of cyclic AMP production in CHO cells expressing wild type TSHR

| Test sample in cyclic AMP assay buffer | Cyclic AMP concentration (pmol/mL mean ± SD; n = 3) |
|---|---|
| 100 µg/mL 5C9 + M22 | 0.35 ± 0.08 |
| 100 µg/mL 9D33 + 100 µg/mL 5C9 + M22 | 0.70 ± 0.40 |
| 10 µg/mL 9D33 + M22 | 2.5 ± 0.8 |
| 10 µg/mL 5C9 + M22 | 0.36 ± 0.25 |
| 10 µg/mL 9D33 + 10 µg/mL 5C9 + M22 | 0.52 ± 0.12 |
| 1 µg/mL 9D33 + M22 | 5.25 ± 0.55 |
| 1 µg/mL 5C9 + M22 | 0.93 ± 0.07 |
| 1 µg/mL 9D33 + 1 µg/mL 5C9 + M22 | 0.69 ± 0.13 |
| 0.1 µg/mL 9D33 + M22 | 27.6 ± 2.5 |
| 0.1 µg/mL 5C9 + M22 | 6.0 ± 2.6 |
| 0.1 µg/mL 9D33 + 0.1 µg/mL 5C9 + M22 | 13.7 ± 7.5 |
| 0.01 µg/mL 9D33 + M22 | 47.5 ± 4.5 |
| 0.01 µg/mL 5C9 + M22 | 48.1 ± 5.4 |
| 0.01 µg/mL 9D33 + 0.01 µg/mL 5C9 ± M22 | 47.5 ± 4.5 |
| Experiment 2 | |
| Buffer only | 1.69 ± 0.47 |
| M22 3 ng/mL | 68.3 ± 6.3 |
| 100 µg/mL 9D33 | 1.76 ± 0.43 |
| 100 µg/mL 5C9 | 0.69 ± 0.18 |
| 100 µg/mL 9D33 + 100 µg/mL 5C9 | 1.16 ± 0.35 |
| 100 µg/mL 9D33 + M22 | 1.42 ± 1.20 |
| 100 µg/mL 5C9 + M22 | undetectable |
| 100 µg/mL 9D33 + 100 µg/mL 5C9 ± M22 | 0.14 (n = 2) |
| 10 µg/mL 9D33 + M22 | 0.67 (n = 2) |
| 10 µg/mL 5C9 + M22 | 0.14 (n = 1) |
| 10 µg/mL 9D33 + 10 µg/mL 5C9 + M22 | 2.41 (n = 1) |
| 1 µg/mL 9D33 + M22 | 6.03 ± 1.15 |
| 1 mg/mL 5C9 + M22 | 2.54 (n = 1) |
| 1 µg/mL 9D33 + 1 µg/mL 5C9 + M22 | 1.51 (n = 1) |
| 0.1 µg/mL 9D33 + M22 | 38.7 ± 8.1 |
| 0.1 µg/mL 5C9 + M22 | 4.17 ± 1.7 |
| 0.1 µg/mL 9D33 + 0.1 µg/mL 5C9 + M22 | 5.17 ± 2.85 |
| 0.01 µg/mL 9D33 + M22 | 60.2 ± 8.0 |
| 0.01 µg/mL 5C9 + M22 | 57.3 ± 13.7 |
| 0.01 µg/mL 9D33 + 0.01 µg/mL 5C9 + M22 | 40.4 ± 5.3 |
| 0.001 µg/mL 9D33 + M22 | 79.1 ± 26.3 |
| 0.001 µg/mL 5C9 + M22 | 63.3 ± 19.0 |
| 0.001 µg/mL 9D33 + 0.001 µg/mL 5C9 + M22 | 40.2 ± 8.7 |
| Experiment 3 | |
| Buffer only | 0.86 ± 0.12 |
| M22 0.3 ng/mL | 21.8 ± 3.23 |
| 100 µg/mL 9D33 | 0.88 ± 0.30 |
| 100 µg/mL 5C9 | 0.58 ± 0.28 |
| 100 µg/mL 9D33 + 100 µg/mL 5C9 | 0.81 ± 0.36 |
| 100 µg/mL 9D33 + M22 | 1.03 ± 0.32 |
| 100 µg/mL 5C9 + M22 | 0.05 (n = 2) |
| 100 µg/mL 9D33 + 100 µg/mL 5C9 + M22 | 0.06 (n = 2) |
| 10 µg/mL 9D33 + M22 | 0.97 ± 0.48 |
| 10 µg/mL 5C9 + M22 | 0.20 (n = 2) |
| 10 µg/mL 9D33 + 10 µg/mL 5C9 + M22 | 0.14 ± 0.08 |
| 1 µg/mL 9D33 + M22 | 0.83 ± 0.21 |
| 1 µg/mL 5C9 + M22 | 0.02 (n = 2) |
| 1 µg/mL 9D33 + 1 µg/mL 5C9 + M22 | 0.13 ± 0.13 |
| 0.1 µg/mL 9D33 + M22 | 5.38 ± 1.71 |
| 0.1 µg/mL 5C9 + M22 | 1.43 ± 1.09 |
| 0.1 µg/mL 9D33 + 0.1 µg/mL 5C9 + M22 | 2.39 ± 1.0 |
| 0.01 µg/mL 9D33 + M22 | 15.2 ± 1.42 |
| 0.01 µg/mL 5C9 + M22 | 13.1 ± 1.34 |
| 0.01 µg/mL 9D33 + 0.01 µg/mL 5C9 + M22 | 12.7 ± 3.4 |
| 0.001 µg/mL 9D33 + M22 | 12.8 ± 1.60 |
| 0.001 µg/mL 5C9 + M22 | 13.3 ± 0.89 |
| 0.001 µg/mL 9D33 + 0.001 µg/mL 5C9 + M22 | 15.8 ± 2.15 |
| Experiment 4 | |
| Buffer only | 1.29 ± 0.68 |
| M22 0.3 ng/mL | 31.1 ± 9.4 |
| 100 µg/mL 9D33 | 2.38 ± 1.11 |
| 100 µg/mL 5C9 | 0.12 ± 0.09 |
| 100 µg/mL 9D33 + 100 µg/mL 5C9 | 0.81 ± 0.15 |
| 100 µg/mL 9D33 + M22 | 2.00 ± 0.87 |
| 100 µg/mL 5C9 + M22 | 0.22 ± 0.11 |
| 100 µg/mL 9D33 + 100 µg/mL 5C9 + M22 | 0.40 ± 0.18 |
| 10 µg/mL 9D33 + M22 | 1.25 ± 0.09 |
| 10 µg/mL 5C9 + M22 | 0.40 ± 0.17 |
| 10 µg/mL 9D33 + 10 µg/mL 5C9 + M22 | 0.45 ± 0.31 |
| 1 µg/mL 9D33 + M22 | 2.66 ± 0.64 |
| 1 µg/mL 5C9 + M22 | 0.21 ± 0.18 |
| 1 µg/mL 9D33 + 1 µg/mL 5C9 + M22 | 0.14 ± 0.07 |
| 0.1 µg/mL 9D33 + M22 | 27.6 ± 2.5 |
| 0.1 µg/mL 5C9 + M22 | 6.0 ± 2.6 |
| 0.1 µg/mL 9D33 + 0.1 µg/mL 5C9 + M22 | 7.2 ± 3.9 |
| 0.01 µg/mL 9D33 + M22 | 38.9 ± 6.4 |
| 0.01 µg/mL 5C9 + M22 | 31.5 ± 4.0 |
| 0.01 µg/mL 9D33 + 0.01 µg/mL 5C9 + M22 | 20.6 ± 5.3 |
| 0.001 µg/mL 9D33 + M22 | 43.2 ± 7.9 |
| 0.001 µg/mL 5C9 + M22 | 33.1 ± 4.0 |
| 0.001 µg/mL 9D33 + 0.001 µg/mL 5C9 + M22 | 25.3 ± 6.0 |

TABLE 14

Effect of 5C9 and 9D33 IgG on basal cyclic AMP production in CHO cells expressing wild type TSHR (approximately $5 \times 10^5$ receptors per cell)

Experiment 1

| Test Sample | Cyclic AMP concentration pmol/mL (mean ± SD; n = 3) | % Inhibition of basal cyclic AMP production. |
|---|---|---|
| Cyclic AMP assay buffer only | 47.1 ± 11.7 | 0 |
| 3 ng/mL TSH | 152.0 ± 28.2 | −ve |
| 5B3[a] IgG 100 µg/mL | 44.5 ± 5.2 | 5.3 |
| 5B3[a] IgG 10 µg/mL | 45.4 ± 6.3 | 3.4 |
| 5B3[a] IgG 1 µg/mL | 52.0 ± 12.1 | −ve |
| 9D33 IgG 100 µg/mL | 74.2 ± 7.2 | −ve |
| 9D33 IgG 10 µg/mL | 56.5 ± 4.0 | −ve |
| 9D33 IgG 1 µg/mL | 65.8 ± 9.8 | −ve |
| 9D33 IgG 0.1 µg/mL | 61.7 ± 13.3 | −ve |
| 9D33 IgG 0.01 µg/mL | 52.0 ± 5.1 | −ve |
| 9D33 IgG 0.001 µg/mL | 61.6 ± 3.8 | −ve |

In control CHO cells, not expressing the TSHR, basal cyclic AMP production in the presence of cyclic AMP assay buffer was 1.02 ± 0.06 pmol/mL (mean ± SD; n = 3) and in the presence of 3 ng/mL TSH was 0.74 ± 0.32 pmol/mL (mean ± SD; n = 3).
−ve = negative i.e. no inhibition of cyclic AMP production.
[a]5B3 is a human monoclonal antibody to glutamic acid decarboxylase (GAD) (negative control for 5C9).

TABLE 14-continued

Experiment 2

| Test Sample | Cyclic AMP concentration pmol/mL (mean ± SD; n = 3) | % Inhibition of basal cyclic AMP production. |
|---|---|---|
| Cyclic AMP assay buffer only | 58.0 ± 15.2 | 0 |
| 3 ng/mL TSH | 156.5 ± 22.2 | −ve |
| 5B3[a] IgG 100 µg/mL | 52.7 ± 7.8 | 9.1 |
| 5B3[a] IgG 10 µg/mL | 43.7 ± 10.4 | 24.7 |
| 5B3[a] IgG 1 µg/mL | 55.9 ± 12.2 | 3.7 |
| 5C9 IgG 100 µg/mL | 26.2 ± 2.7 | 54.9 |
| 5C9 IgG 10 µg/mL | 14.7 ± 1.7 | 74.6 |
| 5C9 IgG 1 µg/mL | 16.8 ± 4.2 | 71.0 |
| 5C9 IgG 0.1 µg/mL | 31.5 ± 8.8 | 45.7 |
| 5C9 IgG 0.01 µg/mL | 36.4 ± 4.5 | 37.2 |
| 5C9 IgG 0.001 µg/mL | 51.7 ± 9.8 | 10.8 |

In control CHO cells, not expressing the TSHR, basal cyclic AMP production in the presence of cyclic AMP assay buffer was 0.03 pmol/mL (n = 2) and in the presence of 3 ng/mL TSH was 0.40 ± 0.09 pmol/mL. (mean + SD; n = 3).
−ve = negative i.e. no inhibition of cyclic AMP production.
[a]5B3 is a human monoclonal antibody to glutamic acid decarboxylase (GAD) (negative control for 5C9).

Experiment 3
Effects of 5C9 Fab and F(ab') on basal cyclic AMP production in CHO cells expressing wild type TSHR

| Test Sample in cyclic AMP assay buffer | Cyclic AMP concentration pmol/mL (mean ± SD; n = 3) | % Inhibition of basal cyclic AMP production |
|---|---|---|
| Cyclic AMP assay buffer only | 59.4 ± 8.6 | 0 |
| 9D33 IgG 100 µg/mL | 67.8 ± 1.0 | −ve |
| 9D33 IgG 10 µg/mL | 79.4 ± 9.8 | −ve |
| 9D33 IgG 1 µg/mL | 71.5 ± 8.8 | −ve |
| 9D33 IgG 0.1 µg/mL | 75.6 ± 8.9 | −ve |
| 9D33 IgG 0.01 µg/mL | 60.5 ± 7.5 | −ve |
| 9D33 IgG 0.001 µg/mL | 52.3 ± 6.3 | 12 |
| 5C9 IgG 100 µg/mL | 26.2 ± 1.8 | 56 |
| 5C9 IgG 10 µg/mL | 24.5 ± 5.8 | 59 |
| 5C9 IgG 1 µg/mL | 22.9 ± 2.1 | 61 |
| 5C9 IgG 0.1 µg/mL | 59.1 ± 2.6 | 1 |
| 5C9 IgG 0.01 µg/mL | 64.3 ± 8.4 | −ve |
| 5C9 IgG 0.001 µg/mL | 67.3 ± 9.8 | −ve |
| 5C9 Fab 100 µg/mL | 23.3 ± 2.3 | 61 |
| 5C9 Fab 10 µg/mL | 32.1 ± 4.8 | 46 |
| 5C9 Fab 1 µg/mL | 36.4 ± 1.5 | 39 |
| 5C9 Fab 0.1 µg/mL | 52.8 ± 1.9 | 11 |
| 5C9 Fab 0.01 µg/mL | 61.1 ± 2.4 | −ve |
| 5C9 Fab 0.001 µg/mL | 62.5 ± 7.3 | −ve |
| 5C9 F(ab') 100 µg/mL | 30.9 ± 2.6 | 48 |
| 5C9 F(ab') 10 µg/mL | 36.5 ± 3.4 | 39 |
| 5C9 F(ab') 1 µg/mL | 45.9 ± 4.5 | 23 |
| 5C9 F(ab') 0.1 µg/mL | 48.2 ± 3.1 | 19 |
| 5C9 F(ab') 0.01 µg/mL | 62.3 ± 5.7 | −ve |
| 5C9 F(ab') 0.001 µg/mL | 57.9 ± 9.1 | 3 |

In control CHO cells, not expressing the TSHR, basal cyclic AMP production in the presence of cyclic AMP assay buffer was 0.03 pmol/mL (n = 2) and in the presence of 3 ng/mL TSH was 0.40 ± 0.09 pmol/mL. (mean ± SD; n = 3).
−ve = negative i.e. no inhibition of cyclic AMP production.
F(ab') prepared by reduction of F(ab')$_2$; see text for details.

TABLE 15

Effect of patient sera TSHR autoantibodies with antagonist activity (B2-B5) on basal cyclic AMP in levels in CHO cells expressing the TSHR I568T activating mutation

Experiment 1

| Test Sample and serum dilution | Cyclic AMP concentration pmol/mL (mean ± SD; n = 3) | % Inhibition of basal cyclic AMP production. |
|---|---|---|
| Cyclic AMP assay buffer only | 20.5 ± 8.7 | 0 |
| HBD pool/10 | 19.5 ± 3.4 | 5 |
| HBD pool/50 | 25.7 ± 2.8 | −ve |
| N1/10 | 20.7 ± 5.5 | −ve |
| N1/50 | 18.5 ± 1.5 | 10 |
| N2/10 | 23.3 ± 1.7 | −ve |
| N2/50 | 17.6 ± 1.8 | 14 |
| N3/10 | 20.3 ± 2.4 | 1 |
| N3/50 | 23.6 ± 5.9 | −ve |
| B2/10 | 5.3 ± 1.3 | 74 |
| B2/50 | 9.6 ± 2.8 | 53 |
| B3/10 | 8.3 ± 3.1 | 60 |
| B3/50 | 10.5 ± 2.5 | 49 |
| B4/10 | 2.2 ± 0.5 | 89 |
| B4/50 | 3.0 ± 0.3 | 86 |
| B5/10 | 15.9 ± 3.3 | 23 |
| B5/50 | 14.5 ± 1.3 | 29 |

Experiment 2

| Test Sample and serum dilution | Cyclic AMP concentration pmol/mL (mean ± SD; n = 3) | % Inhibition of basal cyclic AMP stimulation |
|---|---|---|
| Cyclic AMP assay buffer only | 19.7 ± 3.7 | 0 |
| HBD pool/10 | 28.0 ± 1.6 | −ve |
| HBD pool/50 | 18.1 ± 3.9 | 8 |
| HBD pool/100 | 18.0 ± 1.6 | 9 |
| HBD pool/500 | 17.8 ± 1.3 | 10 |
| HBD pool/1000 | 20.7 ± 2.9 | −ve |
| HBD pool/5000 | 15.6 ± 2.1 | 20 |
| B3/10 | 14.7 ± 2.2 | 25 |
| B3/50 | 13.7 ± 1.3 | 31 |
| B3/100 | 12.6 ± 0.6 | 36 |
| B3/500 | 19.0 ± 0.8 | 4 |
| B3/1000 | 18.4 ± 4.6 | 7 |
| B3/5000 | 17.6 ± 0.9 | 11 |
| B4/10 | 4.0 ± 0.5 | 80 |
| B4/50 | 3.6 ± 0.8 | 81 |
| B4/100 | 3.8 ± 1.1 | 81 |
| B4/500 | 7.2 ± 2.6 | 64 |
| B4/1000 | 12.0 ± 0.6 | 39 |
| B4/5000 | 17.7 ± 2.7 | 10 |

−ve = negative i.e. no inhibition of cyclic AMP production.
HBD pool = pool of healthy blood donor sera
N1-N3 = individual healthy blood donor sera
All sera were diluted in cyclic AMP assay buffer.

TABLE 16

Effect of patient sera TSHR autoantibodies with antagonist activity (B2-B5) on basal cyclic AMP levels in CHO cells expressing the TSHR S281I activating mutation

| Test Sample and serum dilution | Cyclic AMP concentration pmol/mL (mean ± SD; n = 3) | % Inhibition of basal cyclic AMP production |
|---|---|---|
| Cyclic AMP assay buffer only | 11.2 ± 2.0 | 0 |
| HBD/10 | 12.1 ± 0.6 | −8 |
| HBD/50 | 10.0 ± 2.0 | 11 |

TABLE 16-continued

Effect of patient sera TSHR autoantibodies with antagonist activity (B2-B5) on basal cyclic AMP levels in CHO cells expressing the TSHR S281I activating mutation

| Test Sample and serum dilution | Cyclic AMP concentration pmol/mL (mean ± SD; n = 3) | % Inhibition of basal cyclic AMP production |
|---|---|---|
| N1/10 | 8.0 ± 1.6 | 28 |
| N1/50 | 10.8 ± 3.3 | 4 |
| N2/10 | 8.8 ± 1.4 | 21 |
| N2/50 | 8.8 ± 2.3 | 22 |
| N3/10 | 10.0 ± 0.8 | 17 |
| N3/50 | 9.3 ± 1.7 | 17 |
| B2/10 | 7.7 ± 039 | 31 |
| B2/50 | 5.7 ± 1.3 | 49 |
| B3/10 | 5.4 ± 0.5 | 52 |
| B3/50 | 6.6 ± 1.1 | 41 |
| B4/10 | 5.4 ± 1.1 | 52 |
| B4/50 | 4.9 ± 0.7 | 56 |
| B5/10 | 9.1 ± 2.5 | 18 |
| B5/50 | 7.6 ± 0.8 | 32 |

See Table 15 for explanatory footnotes.
5C9 IgG at 1 μg/mL caused 71% inhibition of basal cyclic AMP activity in the experiments with TSHR S281I.

TABLE 17

Effect of patient sera TSHR autoantibodies with antagonist activity (B2-B5) on basal cyclic AMP levels in CHO cells expressing the TSHR A623I activating mutation

| Test Sample and serum dilution | Cyclic AMP concentration pmol/mL (mean ± SD; n = 3) | % Inhibition of basal cyclic AMP production |
|---|---|---|
| Cyclic AMP assay buffer only | 43.5 ± 11.2 | 0 |
| HBD pool/10 | 34.7 ± 4.5 | 20 |
| HBD pool/50 | 49.9 ± 5.7 | −15 |
| N1/10 | 32.1 ± 2.5 | 26 |
| N1/50 | 43.9 ± 12.0 | −1 |
| N2/10 | 51.1 ± 8.4 | −17 |
| N2/50 | 32.6 ± 2.1 | 26 |
| N3/10 | 47.2 ± 7.1 | −10 |
| N3/50 | 57.3 ± 16.5 | −32 |
| B2/10 | 28.8 ± 1.1 | 34 |
| B2/50 | 43.9 ± 2.7 | −1 |
| B3/10 | 33.5 ± 3.5 | 23 |
| B3/50 | 44.2 ± 12.7 | −1 |
| B4/10 | 27.2 ± 6.6 | 37 |
| B4/50 | 23.9 ± 1.0 | 45 |

TABLE 17-continued

Effect of patient sera TSHR autoantibodies with antagonist activity (B2-B5) on basal cyclic AMP levels in CHO cells expressing the TSHR A623I activating mutation

| Test Sample and serum dilution | Cyclic AMP concentration pmol/mL (mean ± SD; n = 3) | % Inhibition of basal cyclic AMP production |
|---|---|---|
| B5/10 | 19.2 ± 6.3 | 56 |
| B5/50 | 40.6 ± 10.9 | 7 |

See Table 15 for explanatory footnotes.
5C9 IgG at 1 μg/mL caused 49% inhibition of basal cyclic AMP activity in experiments with TSHR A623I.

TABLE 18

Effect of patient sera TSHR autoantibodies with antagonist activity (B2-B5) on basal cyclic AMP levels in CHO cell line expressing wild type TSHR (approximately $5 \times 10^5$ receptors per cell)

| Test Sample and serum dilution | Cyclic AMP concentration pmol/mL (mean ± SD; n = 3) | Change in basal cyclic AMP production (%) |
|---|---|---|
| Cyclic AMP assay buffer only | 28.1 ± 0.7 | 100 |
| HBD/10 | 37.5 ± 6.9 | 133 |
| HBD/50 | 37.2 ± 2.4 | 132 |
| N1/10 | 27.7 ± 5.7 | 99 |
| N1/50 | 26.0 ± 4.8 | 93 |
| N2/10 | 41.0 ± 2.7 | 146 |
| N2/50 | 27.0 ± 1.2 | 96 |
| N3/10 | 34.3 ± 2.7 | 122 |
| N3/50 | 38.5 ± 7.8 | 137 |
| B2/10 | 39.7 ± 1.7 | 141 |
| B2/50 | 41.4 ± 3.8 | 147 |
| B3/10 | 74.0 ± 11.2 | 263 |
| B3/50 | 46.5 ± 8.7 | 165 |
| B4/10 | 8.7 ± 0.3 | 31 |
| B4/50 | 17.2 ± 1.9 | 61 |
| B5/10 | 54.2 ± 6.0 | 193 |
| B5/50 | 48.0 ± 10.5 | 171 |

Change in basal cyclic AMP production (%) =
$$\frac{\text{cyclic AMP production in the presence of test sample}}{\text{cyclic AMP production in the presence of cyclic AMP buffer}} \times 100$$

In the presence of 5C9 IgG at 1 μg/mL, basal cyclic AMP levels decreased to 33% relative to levels in the presence of cyclic AMP assay buffer.

TABLE 19

Summary of the effects of patient sera TSHR autoantibodies with antagonist activity (B2-B5) on basal cyclic AMP levels in TSHR transfected CHO cells

| CHO cells transfected with | Cyclic AMP concentration (fmol/cell well; mean ±SD, n = 3) in the presence of:- | | | | | |
|---|---|---|---|---|---|---|
| | HBD pool | B2 | B3 | B4 | B5 | 5C9 IgG |
| Wild type TSHR | 5531 ± 1140 | 7949 ± 340 | 14804 ± 2240 | 1740 ± 68 | 10849 ± 1206 | 1872 ± 288 |
| TSHR I568T | 3900 ± 671 | 1066 ± 266 | 1660 ± 628 | 438 ± 90 | 3180 ± 650 | 548 ± 78 |
| TSHR A623I | 6420 ± 968 | 5760 ± 224 | 6700 ± 704 | 5440 ± 1324 | 7680 ± 1260 | 1914 ± 176 |
| TSHR S281I | 2420 ± 130 | 1538 ± 175 | 1080 ± 96 | 1080 ± 218 | 1822 ± 494 | 655 ± 60 |

HBD pool = pool of healthy blood donor sera.
HBD pool and sera B2-B5 were used at 1:10 dilution in cyclic AMP assay buffer.
5C9 IgG was used at a concentration of 1 μg/mL in cyclic AMP assay buffer.
B2-B5 blocked both TSH and M22 stimulation of cyclic AMP production in CHO cells expressing wild type TSHR.

TABLE 20a

Effect of 5C9 IgG on pTSH stimulated cyclic AMP production in CHO cells expressing wild type TSHR and TSHR with Asp43 mutated to Alanine.

| Test sample | Cyclic AMP produced (fmol/cell well; mean ± SD, n = 3) | | Mutated/wild type (%) |
| --- | --- | --- | --- |
| | Wild type TSHR | Mutated TSHR | |
| Cyclic AMP assay buffer only | 277 ± 109 | 173 ± 81 | 76 |
| TSH only | 13924 ± 717 | 11651 ± 465 | 84 |
| 5B3[a] 10 µg/mL + TSH | 14263 ± 2791 | 17452 ± 2160 | 122 |
| 5B3[a] 100 µg/mL + TSH | 18892 ± 1222 | 12685[1] | 67 |
| 5C9 0.01 µg/mL + TSH | 13145[1] | 12722 ± 695 | 97 |
| 5C9 0.1 µg/mL + TSH | 7813 ± 505 | 6726 ± 488 | 86 |
| 5C9 1.0 µg/mL + TSH | 2021 ± 515 | 471 ± 217 | 23 |
| 5C9 10 µg/mL + TSH | 306 ± 287 | 119 ± 68 | 39 |
| 5C9 100 µg/mL + TSH | 84 ± 93 | 31[2] | 37 |
| 5C9 100 µg/mL only | 47 ± 23 | 206 ± 107 | 438 |

[1] mean of duplicate determinations
[2] single determination
pTSH concentration = 3 ng/mL
All dilutions in cyclic AMP assay buffer
[a] 5B3 is a human monoclonal antibody to glutamic acid decarboxylase (GAD) (negative control for 5C9).

TABLE 20b

Effect of 5C9 IgG on pTSH stimulated cyclic AMP production in CHO cells expressing wild type TSHR and TSHR with Glu61 mutated to Alanine.

| Test sample | Cyclic AMP produced (fmol/cell well; mean ± SD, n = 3) | | Mutated/wild type (%) |
| --- | --- | --- | --- |
| | Wild type TSHR | Mutated TSHR | |
| Cyclic AMP assay buffer only | 210 ± 101 | 146 ± 22 | 70 |
| TSH only | 12818 ± 2224 | 15398 ± 982 | 120 |
| 5B3[a] 10 µg/mL + TSH | 11522 ± 2220 | 19750 ± 2950 | 171 |
| 5B3[a] 100 µg/mL + TSH | 14090 ± 2394 | 15680 ± 2708 | 111 |
| 5C9 0.01 µg/mL + TSH | 13806 ± 1188 | 18050 ± 2948 | 131 |
| 5C9 0.1 µg/mL + TSH | 2886 ± 422 | 2114 ± 592 | 73 |
| 5C9 1.0 µg/mL + TSH | 536 ± 150 | 766 ± 354 | 143 |
| 5C9 10 µg/mL + TSH | 254 ± 208 | 346 ± 292 | 136 |
| 5C9 100 µg/mL + TSH | 202[1] | 328 ± 96 | 162 |
| 5C9 100 µg/mL only | 218 ± 46 | 254 ± 48 | 117 |

See Table 20a for explanatory footnotes.

TABLE 20c

Effect of 5C9 IgG on pTSH stimulated cyclic AMP production in CHO cells expressing wild type TSHR and TSHR with His105 mutated to Alanine.

| Test sample | Cyclic AMP produced (fmol/cell well; mean ± SD, n = 3) | | Mutated/wild type (%) |
| --- | --- | --- | --- |
| | Wild type TSHR | Mutated TSHR | |
| Cyclic AMP assay buffer only | 245 ± 98 | 590 ± 72 | 241 |
| TSH only | 14214 ± 2111 | 17979 ± 1735 | 126 |
| 5B3[a] 10 µg/mL + TSH | 13214 ± 3233 | 21359 ± 1501 | 162 |
| 5B3[a] 100 µg/mL + TSH | 17232 ± 2641 | 24044 ± 3398 | 140 |
| 5C9 0.01 µg/mL + TSH | 16652 ± 2252 | 24168 ± 1690 | 145 |
| 5C9 0.1 µg/mL + TSH | 3511 ± 590 | 2869 ± 1460 | 82 |
| 5C9 1.0 µg/mL + TSH | 454 ± 11 | 561 ± 393 | 124 |
| 5C9 10 µg/mL + TSH | 289 ± 84 | 434 ± 392 | 150 |
| 5C9 100 µg/mL + TSH | 223[1] | 134[1] | 60 |
| 5C9 100 µg/mL only | 234 ± 50 | 520 ± 198 | 222 |

See Table 20a for explanatory footnotes.

TABLE 20d

Effect of 5C9 IgG on pTSH stimulated cyclic AMP production in CHO cells expressing wild type TSHR and TSHR with Glu107 mutated to Alanine.

| Test sample | Cyclic AMP produced mol/cell well; mean ± SD, n = 3) | | Mutated/wild type (%) |
| --- | --- | --- | --- |
| | Wild type TSHR | Mutated TSHR | |
| Experiment 1 | | | |
| Cyclic AMP assay buffer only | 326 ± 157 | 1898 ± 594 | 582 |
| TSH only | 14838 ± 1396 | 13435 ± 2613 | 91 |
| 5B3[a] 10 µg/mL + TSH | 14018 ± 3049 | 17074 ± 1442 | 122 |
| 5B3[a] 100 µg/mL + TSH | 15949 ± 1340 | 16009 ± 4606 | 100 |
| 5C9 0.01 µg/mL + TSH | 17001 ± 5209 | 15008 ± 1053 | 88 |
| 5C9 0.1 µg/mL + TSH | 5950[1] | 5783 ± 3213 | 97 |
| 5C9 1.0 µg/mL + TSH | 1058 ± 396 | 394 ± 314 | 37 |
| 5C9 10 µg/mL + TSH | 496 ± 52 | 449 ± 116 | 91 |
| 5C9 100 µg/mL + TSH | 193 ± 196 | 203 ± 56 | 105 |
| 5C9 100 µg/mL only | 1266 ± 359 | 462 ± 324 | 36 |
| Experiment 2 | | | |
| Cyclic AMP assay buffer only | 167 ± 148 | 1824 ± 354 | 1092 |
| TSH only | 17569 ± 3919 | 19358 ± 2365 | 110 |
| 5B3[a] 10 µg/mL + TSH | 11692 ± 1161 | 21255 ± 2597 | 182 |
| 5B3[a] 100 µg/mL + TSH | 24141 ± 1869 | 22933 ± 6554 | 95 |
| 5C9 0.01 µg/mL + TSH | 18585 ± 5353 | 21028 ± 1432 | 113 |
| 5C9 0.1 µg/mL + TSH | 4221 ± 1003 | 1544 ± 732 | 37 |
| 5C9 1.0 µg/mL + TSH | 738 ± 48 | 28[1] | 4 |
| 5C9 10 µg/mL + TSH | 214 ± 343 | 321 ± 514 | 150 |
| 5C9 100 µg/mL + TSH | 238[1] | 64[2] | 27 |
| 5C9 100 µg/mL only | 211 ± 75 | 408 ± 138 | 193 |

See Table 20a for explanatory footnotes.

TABLE 20e

Effect of 5C9 IgG on pTSH stimulated cyclic AMP production in CHO cells expressing wild type TSHR and TSHR with Phe130 mutated to Alanine.

| Test sample | Cyclic AMP produced (fmol/cell well; mean ± SD, n = 3) | | Mutated/wild type (%) |
| --- | --- | --- | --- |
| | Wild type TSHR | Mutated TSHR | |
| Cyclic AMP assay buffer only | 345 ± 119 | 410 ± 85 | 119 |
| TSH only | 15897 ± 1291 | 16392 ± 1318 | 103 |
| 5B3[a] 10 µg/mL + TSH | 18414 ± 1662 | 15765 ± 1088 | 86 |
| 5B3[a] 100 µg/mL + TSH | 19561 ± 1078 | 21673 ± 3165 | 111 |
| 5C9 0.01 µg/mL + TSH | 15255 ± 2166 | 17414 ± 1020 | 114 |
| 5C9 0.1 µg/mL + TSH | 2712 ± 462 | 9015 ± 1835 | 332 |
| 5C9 1.0 µg/mL + TSH | 398 ± 378 | 2235 ± 1635 | 562 |
| 5C9 10 µg/mL + TSH | 151 ± 195 | 1139 ± 146 | 754 |
| 5C9 100 µg/mL + TSH | 240 ± 199 | 603 ± 141 | 251 |
| 5C9 100 µg/mL only | 334 ± 75 | 446 ± 41 | 134 |

See Table 20a for explanatory footnotes.

TABLE 20f

Effect of 5C9 IgG on pTSH stimulated cyclic AMP production in CHO cells expressing wild type TSHR and TSHR with Glu178 mutated to Alanine.

| Test sample | Cyclic AMP produced (fmol/cell well; mean ± SD, n = 3) | | Mutated/wild type (%) |
| --- | --- | --- | --- |
| | Wild type TSHR | Mutated TSHR | |
| Cyclic AMP assay buffer only | 183 ± 77 | 366 ± 300 | 200 |
| TSH only | 8900 ± 1185 | 7666 ± 1659 | 86 |

TABLE 20f-continued

Effect of 5C9 IgG on pTSH stimulated cyclic AMP production in CHO cells expressing wild type TSHR and TSHR with Glu178 mutated to Alanine.

| Test sample | Cyclic AMP produced (fmol/cell well; mean ± SD, n = 3) Wild type TSHR | Mutated TSHR | Mutated/wild type (%) |
|---|---|---|---|
| 5B3[a] 10 µg/mL + TSH | 9160 ± 3180 | 10828 ± 1650 | 118 |
| 5B3[a] 100 µg/mL + TSH | 12920 ± 1300 | 9428 ± 1350 | 73 |
| 5C9 0.01 µg/mL + TSH | 12580 ± 2700 | 8166 ± 195 | 65 |
| 5C9 0.1 µg/mL + TSH | 4354 ± 920 | 7314 ± 1830 | 168 |
| 5C9 1.0 µg/mL + TSH | 688 ± 140 | 3570 ± 850 | 519 |
| 5C9 10 µg/mL + TSH | 630 ± 140 | 1904 ± 360 | 302 |
| 5C9 100 µg/mL + TSH | 712[1] | 894 ± 120 | 126 |
| 5C9 100 µg/mL only | 196 ± 58 | 134 ± 153 | 68 |

See Table 20a for explanatory footnotes.

TABLE 20g

Effect of 5C9 IgG on pTSH stimulated cyclic AMP production in CHO cells expressing wild type TSHR and TSHR with Tyr185 mutated to Alanine.

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 139 ± 40 | 163 ± 72 | 117 |
| TSH only | 12649 ± 1577 | 8305 ± 870 | 66 |
| 5B3[a] 10 µg/mL + TSH | 16974 ± 205 | 10088 ± 1856 | 59 |
| 5B3[a] 100 µg/mL + TSH | 17089 ± 2282 | 10920 ± 2111 | 64 |
| 5C9 0.01 µg/mL + TSH | 17264 ± 4257 | 9368 ± 2069 | 54 |
| 5C9 0.1 µg/mL + TSH | 6217 ± 2064 | 4536 ± 724 | 73 |
| 5C9 1.0 µg/mL + TSH | 1664 ± 636 | 1199 ± 1042 | 72 |
| 5C9 10 µg/mL + TSH | 481 ± 380 | 301 ± 199 | 63 |
| 5C9 100 µg/mL + TSH | 275 ± 206 | UD | |
| 5C9 100 µg/mL only | 123 ± 38 | 163 ± 60 | 133 |

UD = below assay detection limit.
See Table 20a for other explanatory footnotes.

TABLE 20h

Effect of 5C9 IgG on pTSH stimulated cyclic AMP production in CHO cells expressing wild type TSHR and TSHR with Asp203 mutated to Alanine.

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 298 ± 164 | 742 ± 122 | 249 |
| TSH only | 11770 ± 398 | 12594 ± 400 | 107 |
| 5B3[a] 10 µg/mL + TSH | 13266 ± 1105 | 12232 ± 1819 | 92 |
| 5B3[a] 100 µg/mL + TSH | 14125 ± 704 | 13006 ± 2452 | 92 |
| 5C9 0.01 µg/mL + TSH | 15454 ± 422 | 14651 ± 511 | 95 |
| 5C9 0.1 µg/mL + TSH | 4445 ± 405 | 13142 ± 1589 | 296 |
| 5C9 1.0 µg/mL + TSH | 1352 ± 249 | 14678 ± 6312 | 1086 |
| 5C9 10 µg/mL + TSH | 807 ± 479 | 12634 ± 1036 | 1566 |
| 5C9 100 µg/mL + TSH | 367 ± 67 | 12721 ± 3187 | 3446 |
| 5C9 100 µg/mL only | 330 ± 46 | 1368 ± 206 | 415 |

See Table 20a for explanatory footnotes.

TABLE 20i

Effect of 5C9 IgG on pTSH stimulated cyclic AMP production in CHO cells expressing wild type TSHR and TSHR with Tyr206 mutated to Alanine.

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 380 ± 166 | 402 ± 96 | 106 |
| TSH only | 15360 ± 670 | 18440 ± 1390 | 120 |
| 5B3[a] 10 µg/mL + TSH | 15880 ± 1150 | 21000 ± 2340 | 132 |
| 5B3[a] 100 µg/mL + TSH | 19100 ± 3090 | 19680 ± 3200 | 103 |
| 5C9 0.01 µg/mL + TSH | 16100 ± 2360 | 18420 ± 670 | 114 |
| 5C9 0.1 µg/mL + TSH | 6220 ± 1500 | 10820 ± 1750 | 174 |
| 5C9 1.0 µg/mL + TSH | 1306 ± 123 | 3460 ± 360 | 265 |
| 5C9 10 µg/mL + TSH | 396 ± 158 | 1564 ± 176 | 395 |
| 5C9 100 µg/mL + TSH | 292 ± 130 | 506 ± 120 | 173 |
| 5C9 100 µg/mL only | 444 ± 98 | 482 ± 286 | 109 |

See Table 20a for explanatory footnotes.

TABLE 20j

Effect of 5C9 IgG on pTSH stimulated cyclic AMP production in CHO cells expressing wild type TSHR and TSHR with Lys209 mutated to Alanine.

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 316 ± 38 | 288 ± 80 | 91 |
| TSH only | 14200 ± 1420 | 9500 ± 1620 | 67 |
| 5B3[a] 10 µg/mL + TSH | 12280 ± 610 | 11200 ± 3000 | 91 |
| 5B3[a] 100 µg/mL + TSH | 16000 ± 1470 | 13240 ± 1530 | 83 |
| 5C9 0.01 µg/mL + TSH | 15440 ± 2180 | 5960 ± 950 | 39 |
| 5C9 0.1 µg/mL + TSH | 4700 ± 339 | 278 ± 40 | 6 |
| 5C9 1.0 µg/mL + TSH | 1184 ± 59 | 360 ± 146 | 30 |
| 5C9 10 µg/mL + TSH | 984 ± 117 | 482 ± 100 | 49 |
| 5C9 100 µg/mL + TSH | 602 ± 240 | 354 ± 184 | 59 |
| 5C9 100 µg/mL only | 272 ± 49 | 280 ± 104 | 103 |

See Table 20a for explanatory footnotes.

TABLE 20k

Effect of 5C9 IgG on TSH stimulated cyclic AMP production in CHO cells expressing wild type TSHR and TSHR with Asp232 mutated to Alanine.

| Test sample | Cyclic AMP produced (fmol/cell well; mean ± SD, n = 3) Wild type TSHR | Mutated TSHR | Mutated/wild type (%) |
|---|---|---|---|
| Cyclic AMP assay buffer only | 650 ± 87 | 652 ± 300 | 100 |
| TSH only | 15681 ± 866 | 14884 ± 1587 | 95 |
| 5B3[a] 10 µg/mL + TSH | 15210 ± 1697 | 17800 ± 3219 | 117 |
| 5B3[a] 100 µg/mL + TSH | 19704 ± 1173 | 17478 ± 3150 | 89 |
| 5C9 0.01 µg/mL + TSH | 17600 ± 1347 | 15330 ± 1593 | 87 |
| 5C9 0.1 µg/mL + TSH | 7329 ± 860 | 6556 ± 1668 | 89 |
| 5C9 1.0 µg/mL + TSH | 1072 ± 705 | 1882 ± 653 | 176 |
| 5C9 10 µg/mL + TSH | 794 ± 406 | 710 ± 596 | 89 |
| 5C9 100 µg/mL + TSH | 166 ± 95 | 55 ± 51 | 33 |
| 5C9 100 µg/mL only | 522 ± 84 | 99[1] | 19 |

See Table 20a for explanatory footnotes.

TABLE 20l

Effect of 5C9 IgG on pTSH stimulated cyclic AMP production in CHO cells expressing wild type TSHR and TSHR with Lys250 mutated to Alanine.

| | Cyclic AMP produced (fmol/cell well; mean ± SD, n = 3) | | Mutated/ wild type |
|---|---|---|---|
| Test sample | Wild type TSHR | Mutated TSHR | (%) |
| Cyclic AMP assay buffer only | 590 ± 86 | 1020 ± 104 | 173 |
| TSH only | 13332 ± 1177 | 10933 ± 1510 | 82 |
| 5B3[a] 10 μg/mL + TSH | 11292 ± 1784 | 13410 ± 2930 | 119 |
| 5B3[a] 100 μg/mL + TSH | 14236 ± 3521 | 14049 ± 3372 | 99 |
| 5C9 0.01 μg/mL + TSH | 15191 ± 4117 | 14460 ± 2690 | 95 |
| 5C9 0.1 μg/mL + TSH | 6295 ± 1897 | 8486 ± 2961 | 135 |
| 5C9 1.0 μg/mL + TSH | 643 ± 207 | 2567 ± 841 | 399 |
| 5C9 10 μg/mL + TSH | 286 ± 116 | 862 ± 398 | 301 |
| 5C9 100 μg/mL + TSH | 158 ± 244 | 96 ± 57 | 61 |
| 5C9 100 μg/mL only | 458 ± 94 | 448 ± 280 | 98 |

See Table 20a for explanatory footnotes.

TABLE 20m

Effect of 5C9 IgG on pTSH stimulated cyclic AMP production in CHO cells expressing wild type TSHR and TSHR with Glu251 mutated to Alanine.

| | Cyclic AMP produced (fmol/cell well; mean ± SD, n = 3) | | Mutated/ wild type |
|---|---|---|---|
| Test sample | Wild type TSHR | Mutated TSHR | (%) |
| Cyclic AMP assay buffer only | 380 ± 84 | 960 ± 372 | 253 |
| TSH only | 18379 ± 987 | 17492 ± 1332 | 95 |
| 5B3[a] 10 μg/mL + TSH | 15152 ± 4365 | 19951 ± 2362 | 132 |
| 5B3[a] 100 μg/mL + TSH | 18169 ± 3454 | 20461 ± 1345 | 113 |
| 5C9 0.01 μg/mL + TSH | 21197 ± 1280 | 21950 ± 936 | 104 |
| 5C9 0.1 μg/mL + TSH | 8640 ± 2123 | 15532 ± 2571 | 180 |
| 5C9 1.0 μg/mL + TSH | 915 ± 139 | 5240 ± 332 | 573 |
| 5C9 10 μg/mL + TSH | 752 ± 127 | 1881 ± 212 | 250 |
| 5C9 100 μg/mL + TSH | 496 ± 166 | 1170 ± 123 | 236 |
| 5C9 100 μg/mL only | 460 ± 102 | 406 ± 212 | 88 |

See Table 20a for explanatory footnotes.

TABLE 20n

Effect of 5C9 IgG on pTSH stimulated cyclic AMP production in CHO cells expressing wild type TSHR and TSHR with Thr257 mutated to Alanine.

| | Cyclic AMP produced (fmol/cell well; mean ± SD, n = 3) | | Mutated/ wild type |
|---|---|---|---|
| Test sample | Wild type TSHR | Mutated TSHR | (%) |
| Cyclic AMP assay buffer only | 626 ± 153 | 1140 ± 153 | 182 |
| TSH only | 16928 ± 2079 | 18563 ± 1573 | 110 |
| 5B3[a] 10 μg/mL + TSH | 17542 ± 1874 | 23341 ± 4203 | 133 |
| 5B3[a] 100 μg/mL + TSH | 18948 ± 1444 | 20101 ± 2902 | 106 |
| 5C9 0.01 μg/mL + TSH | 18722 ± 3876 | 21088 ± 1810 | 113 |
| 5C9 0.1 μg/mL + TSH | 6143 ± 1233 | 7944 ± 1138 | 129 |
| 5C9 1.0 μg/mL + TSH | 1396 ± 172 | 1594 ± 156 | 114 |
| 5C9 10 μg/mL + TSH | 638 ± 58 | 972 ± 12 | 152 |
| 5C9 100 μg/mL + TSH | 591 ± 99 | 611 ± 52 | 103 |
| 5C9 100 μg/mL only | 566 ± 143 | 637 ± 300 | 111 |

See Table 20a for explanatory footnotes.

TABLE 20o

Effect of 5C9 IgG on pTSH stimulated cyclic AMP production in CHO cells expressing wild type TSHR and TSHR with Arg274 mutated to Alanine.

| | Cyclic AMP produced (fmol/cell well; mean ± SD, n = 3) | | Mutated/ wild type |
|---|---|---|---|
| Test sample | Wild type TSHR | Mutated TSHR | (%) |
| Cyclic AMP assay buffer only | 124 ± 103 | 86 ± 38 | 69 |
| TSH only | 21347 ± 1112 | 11432 ± 2511 | 54 |
| 5B3[a] 10 μg/mL + TSH | 18654 ± 3700 | 12961 ± 2609 | 69 |
| 5B3[a] 100 μg/mL + TSH | 26203 ± 4753 | 13138 ± 2248 | 50 |
| 5C9 0.01 μg/mL + TSH | 16345 ± 3974 | 9557 ± 2479 | 58 |
| 5C9 0.1 μg/mL + TSH | 4997 ± 1392 | 1320 ± 158 | 26 |
| 5C9 1.0 μg/mL + TSH | 808 ± 510 | 177 ± 120 | 22 |
| 5C9 10 μg/mL + TSH | 684 ± 182 | 108[1] | 16 |
| 5C9 100 μg/mL + TSH | 246 ± 165 | 17[2] | 7 |
| 5C9 100 μg/mL only | 111 ± 26 | 34 ± 43 | 31 |

See Table 20a for explanatory footnotes.

TABLE 20p

Effect of 5C9 IgG on pTSH stimulated cyclic AMP production in CHO cells expressing wild type TSHR and TSHR with Asp276 mutated to Alanine.

| | Cyclic AMP produced (fmol/cell well; mean ± SD, n = 3) | | Mutated/ wild type |
|---|---|---|---|
| Test sample | Wild type TSHR | Mutated TSHR | (%) |
| Experiment 1 | | | |
| Cyclic AMP assay buffer only | 365 ± 166 | 1454 ± 258 | 398 |
| TSH only | 17500 ± 727 | 22416 ± 2570 | 128 |
| 5B3[a] 10 μg/mL + TSH | 19354 ± 1794 | 25180 ± 5609 | 130 |
| 5B3[a] 100 μg/mL + TSH | 21671 ± 2064 | 25707 ± 4101 | 119 |
| 5C9 0.01 μg/mL + TSH | 17236 ± 2705 | 26212 ± 2597 | 152 |
| 5C9 0.1 μg/mL + TSH | 5594 ± 723 | 16856 ± 2110 | 301 |
| 5C9 1.0 μg/mL + TSH | 759[1] | 4788 ± 553 | 631 |
| 5C9 10 μg/mL + TSH | 366 ± 145 | 1384 ± 602 | 378 |
| 5C9 100 μg/mL + TSH | 344 ± 566 | 565 ± 176 | 164 |
| 5C9 100 μg/mL only | 300 ± 242 | 602 ± 274 | 201 |
| Experiment 2 | | | |
| Cyclic AMP assay buffer only | 156 ± 30 | 601 ± 190 | 385 |
| TSH only | 13852 ± 756 | 14616 ± 453 | 106 |
| 5B3[a] 10 μg/mL + TSH | 13025 ± 3292 | 17706[1] | 136 |
| 5B3[a] 100 μg/mL + TSH | 14245 ± 1024 | 18041 ± 4561 | 127 |
| 5C9 0.01 μg/mL + TSH | 14066 ± 2291 | 21213 ± 3443 | 151 |
| 5C9 0.1 μg/mL + TSH | 4462 ± 363 | 7320 ± 1614 | 164 |
| 5C9 1.0 μg/mL + TSH | 657 ± 257 | 1513 ± 835 | 230 |
| 5C9 10 μg/mL + TSH | 541 ± 224 | 1301 ± 911 | 240 |
| 5C9 100 μg/mL + TSH | 286 ± 184 | 288 ± 87 | 101 |
| 5C9 100 μg/mL only | 208 ± 15 | 314 ± 69 | 151 |

See Table 20a for explanatory footnotes.

TABLE 21

Summary of effects of TSHR mutations (relative to wild type) on the ability of 5C9 IgG and 9D33 IgG to block TSH stimulation of cyclic AMP production in TSHR transfected CHO cells

| TSHR Mutation | Stimulation (relative to wild type) of cyclic AMP production by pTSH | Blocking (relative to wild type) of TSH stimulation of cyclic AMP production by 5C9 IgG | Blocking (relative to wild type) of TSH stimulation of cyclic AMP production by 9D33 IgG |
|---|---|---|---|
| Wild type | +++++ | +++++ | +++++ |
| Asp 43 Ala | +++ | +++++ | +++++ |
| Lys 58 Ala | +++++ | +++++ | 0 |

TABLE 21-continued

Summary of effects of TSHR mutations (relative to wild type) on the ability of 5C9 IgG and 9D33 IgG to block TSH stimulation of cyclic AMP production in TSHR transfected CHO cells

| TSHR Mutation | Stimulation (relative to wild type) of cyclic AMP production by pTSH | Blocking (relative to wild type) of TSH stimulation of cyclic AMP production by 5C9 IgG | Blocking (relative to wild type) of TSH stimulation of cyclic AMP production by 9D33 IgG |
|---|---|---|---|
| Ile 60 Ala | +++++ | +++++ | +++++ |
| Glu 61 Ala | ++++ | +++++ | +++++ |
| Arg 80 Ala | +++++ | +++++ | 0 |
| Tyr 82 Ala | +++++ | +++++ | 0 |
| Thr 104 Ala | +++++ | +++++ | NT |
| His 105 Ala | +++++ | +++++ | NT |
| Glu 107 Ala | +++ | +++++ | +++++ |
| Arg 109 Ala | +++++ | +++++ | 0 |
| Lys 129 Ala | +++++ | 0 | 0 |
| Phe 130 Ala | +++++ | +++ | +++++ |
| Phe 134 Ala | +++++ | +++++ | ++ |
| Asp 151 Ala | +++++ | ++++ | NT |
| Glu 178 Ala | ++++ | +++ | ++++ |
| Lys 183 Ala | +++++ | + | +++++ |
| Tyr 185 Ala | ++++ | +++++ | +++++ |
| Asp 203 Ala | ++++ | 0 | +++++ |
| Tyr 206 Ala | ++++ | +++ | +++++ |
| Lys 209 Ala | ++++ | +++++++ | +++++ |
| Asp 232 Ala | +++ | +++++ | +++++ |
| Gln 235 Ala | +++++ | +++++ | +++++ |
| Lys 250 Ala | +++++ | ++++ | ++++ |
| Glu 251 Ala | +++++ | +++ | +++++ |
| Arg 255 Ala | +++++ | +++++ | +++++ |
| Thr 257 Ala | +++++ | +++++ | +++++ |
| Trp 258 Ala | +++++ | +++++ | +++++ |
| Arg 274 Ala | +++++ | +++++++ | +++++++ |
| Asp 276 Ala | +++++ | ++++ | +++++ |
| Ser 281 Ala | ++++ | +++++ | ++++ |
| Arg 80 Asp | ++++ | +++++ | 0 |
| Asp 151 Arg | +++++ | +++++ | NT |
| Lys 183 Asp | +++ | + | +++++ |
| Arg 255 Asp | +++++ | +++++ | +++++++ |
| Asp 160 Lys | 0 | +++++[a] | NT | pTSH concentration used = 3 ng/mL.
Relative effects of TSHR mutations were expressed as a percentage of activity observed with wild type as follows:- +++++ = 100% wild type activity; ++++ = <100-80% of wild type activity; +++ = <80-60% of wild type activity; ++ = <60-40% of wild type activity; + = <40-20% of wild type activity; 0 = <20% of wild type activity, and increased activity relative to wild type: >100% = +++++++. NT = not tested.
[a]Stimulation of cyclic AMP for this experiment was tested using M22 due to lack of response to TSH (see text for details)

TABLE 22

Effect of TSHR Asp203Ala mutation on the ability of patient sera TSHR autoantibodies with antagonist activity (B2-B5) to block TSH stimulation of cyclic AMP production

| Test Sample and serum dilution[a] | Wild type TSHR cyclic AMP concentration fmol/cell well. Mean ± SD; n = 3 | Wild type TSHR % inhibition of TSH stimulated cyclic AMP level[b] | TSHR Asp203Ala cyclic AMP concentration fmol/cell well. Mean ± SD; n = 3 | TSHR Asp203Ala % inhibition of TSH stimulated cyclic AMP level[b] |
|---|---|---|---|---|
| Cyclic AMP assay buffer | 242 ± 130 | | 292 ± 89 | |
| TSH[c] | 9357 ± 1155 | | 7591 ± 832 | |
| TSH[c] + 1 µg/mL 5C9 | 1110 ± 811 | 92 | 9400[1] | 4 |
| HBD pool/10 | 183 ± 67 | | 496 ± 76 | |
| TSH[c] + HBD pool/10 | 13303 ± 1819 | 0 | 9756[1] | 0 |
| B2/10 | 110 ± 36 | | 270 ± 72 | |
| TSH[c] + B2/10 | 454 ± 381 | 97 | 1963 ± 357 | 80 |
| B3/10 | 329[1] | | 582 ± 74 | |
| TSH[c] + B3/10 | 3407 ± 1341 | 74 | 4027 ± 278 | 59 |
| B4/10 | 59 ± 22 | | 161 ± 36 | |
| TSH[c] + B4/10 | 278 ± 73 | 98 | 150 ± 41 | 98 |
| B5/10 | 647 ± 170 | | 1064 ± 228 | |
| TSH[c] + B5/10 | 4173 ± 515 | 69 | 6871 ± 618 | 30 |

[a]Dilution in cyclic AMP assay buffer.
[b]% Inhibition of TSH induced cyclic AMP stimulation $$100 \times \left(1 - \frac{\text{cyclic AMP produced in the presence of test sample/10 and TSH (3 ng/mL)}}{\text{cyclic AMP produced in the presence of /10 HBD pool and TSH (3 ng/mL)}}\right)$$

[1]mean of duplicate samples
[c]pTSH used at a final concentration of 3 ng/mL
HBD pool = pool of healthy blood donor sera.

The invention claimed is:

1. An isolated human monoclonal or recombinant antibody for the Thyroid Stimulating Hormone Receptor (TSHR), wherein said antibody is an antagonist of Thyroid Stimulating Hormone (TSH), and has a binding affinity for full length human TSHR of about $10^9$ L/mol, and
wherein said antibody comprises a $V_H$ region comprises the following Complement Determining Regions (CDRs):

a) SNYMS (CDR1)
(SEQ ID NO: 1);

b) VTYSGGSTSYADSVKG (CDR2)
(SEQ ID NO: 2); and c) GGRYCSSISCYARSGCDY (CDR3)
(SEQ ID NO: 3);

and said antibody comprises a $V_L$ region comprises the following CDRs:

a) RASQSISNYLN (CDR1) (SEQ ID NO: 4);

b) AASSLQS (CDR2) (SEQ ID NO: 5); and c) QQSYSSPSTT (CDR3) (SEQ ID NO: 6).

2. The antibody according to claim 1, wherein said antibody is an antagonist of thyroid stimulating antibodies.

3. The antibody according to claim 1, wherein said antibody has TSH antagonist characteristics of patient serum TSHR autoantibodies which are TSH antagonists.

4. The antibody according to claim 1, wherein said antibody has the antagonistic characteristics of patient serum TSHR autoantibodies which are antagonists of thyroid stimulating antibodies.

5. The antibody according to claim 1, wherein said antibody is an inhibitor of binding to TSHR or a portion thereof by TSH, by M22, by antibodies with stimulating activity or antibodies with blocking activity to the TSHR.

6. The antibody according to claim 5, wherein the TSHR portion includes the Leucine Rich Domain (LRD) of TSHR or a substantial portion thereof.

7. The antibody according to claim 1, wherein said antibody comprises or consists of an antigen-binding fragment thereof.

8. The antibody according to claim 1, wherein said antibody has a binding affinity for human full length TSHR of about $10^{10}$ L/mol.

9. A composition comprising the antibody according to claim 1.

10. A pharmaceutical composition comprising the antibody according to claim 1 and a pharmaceutically acceptable carrier.

11. The pharmaceutical composition according to claim 10, wherein the composition comprises thyroid stimulating hormone receptor antagonist 9D33.

12. The antibody according to claim 1, wherein said antibody inhibits TSHR constitutive activity.

13. An isolated humanised monoclonal or recombinant antibody for the TSHR, wherein said antibody is an antagonist of TSH and has a binding affinity for full length human TSHR of about $10^9$ L/mol, and wherein said antibody comprises a $V_H$ region comprises of the following Complement Determining Regions (CDRs):

a) SNYMS (CDR1) (SEQ ID NO: 1);

b) VTYSGGSTSYADSVKG (CDR2) (SEQ ID NO: 2); and c) GGRYCSSISCYARSGCDY (CDR3) (SEQ ID NO: 3);

and said antibody comprises a $V_L$ region comprises of the following CDRs:

a) RASQSISNYLN (CDR1) (SEQ ID NO: 4);

b) AASSLQS (CDR2) (SEQ ID NO: 5); and c) QQSYSSPSTT (CDR3) (SEQ ID NO: 6).

* * * * *

SEQUENCE LISTING

<160> NUMBER OF SEQ IDS NOS: 11

<210> SEQ ID NO 1
<211> LENGTH: 5
<212> TYPE: PRT
<213> ORGANISM: Homo sapiens

<400> SEQUENCE: 1

Ser Asn Tyr Met Ser
1               5

<210> SEQ ID NO 2
<211> LENGTH: 16
<212> TYPE: PRT
<213> ORGANISM: Homo sapiens

<400> SEQUENCE: 2

Val Thr Tyr Ser Gly Gly Ser Thr Ser Tyr Ala Asp Ser Val Lys Gly
1               5                   10                  15

<210> SEQ ID NO 3
<211> LENGTH: 18
<212> TYPE: PRT
<213> ORGANISM: Homo sapiens

<400> SEQUENCE: 3

Gly Gly Arg Tyr Cys Ser Ser Ile Ser Cys Tyr Ala Arg Ser Gly Cys
1               5                   10                  15

Asp Tyr

<210> SEQ ID NO 4
<211> LENGTH: 11
<212> TYPE: PRT
<213> ORGANISM: Homo sapiens

<400> SEQUENCE: 4

Arg Ala Ser Gln Ser Ile Ser Asn Tyr Leu Asn
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
1               5

<210> SEQ ID NO 6
<211> LENGTH: 10
<212> TYPE: PRT
<213> ORGANISM: Homo sapiens

<400> SEQUENCE: 6

Gln Gln Ser Tyr Ser Ser Pro Ser Thr Thr
1               5                   10

<210> SEQ ID NO 7
<211> LENGTH: 699
<212> TYPE: DNA
<213> ORGANISM: Homo sapiens

<400> SEQUENCE: 7
gaagtgcagc tggtggagtc tggaggaggc ctgatccagc ctgggggtc cctgagactc      60

-continued

```
tcctgtgcag cctctgggtt caccgtcagt agcaactaca tgagctgggt ccgccaggct    120
ccagggaagg ggctggagtg ggtctcagtt acttatagcg gtggtagcac atcctacgca    180
gactccgtga agggccgatt caccatctcc agagacaatt ccaagaacac gctgtatctt    240
caaatgaaca gcctgagagc cgaggacacg gccgtgtatt actgtgcgag gggggggcga    300
tattgtagta gtataagctg ctacgcgagg agcgggtgtg actactgggg ccagggaacc    360
ctggtcaccg tctcctcagc ctccaccaag ggcccatcgg tcttcccect ggcaccctec    420 tccaagagca cctctggggg cacagcggcc ctgggctgcc tggtcaagga ctacttcccc    480
gaaccggtga cggtgtcgtg gaactcaggc gccctgacca gcggcgtgca ccttcccg     540 gctgtcctac agtcctcagg actctactcc ctcagcagcg tggtgaccgt gcctccagc    600 agcttgggca cccagaccta catctgcaac gtgaatcaca agcccagcaa caccaaggtg    660
gacaagagag ttgagcccaa atcttgtgac aaaactagt                          699

<210> SEQ ID NO 8
<211> LENGTH: 617
<212> TYPE: DNA
<213> ORGANISM: Homo sapiens

<400> SEQUENCE: 8
gccatccaga tgacccagtc tccttcctcc ctgtctgcat ctgtaggaga cagagtcacc     60
atcacttgcc gggcaagtca gagcattagc aactatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagtt ccccctccac cacttttggc    300
caggggacca agctggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgt                                                  617

<210> SEQ ID NO 9
<211> LENGTH: 233
<212> TYPE: PRT
<213> ORGANISM: Homo sapiens

<400> SEQUENCE: 9

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Thr Tyr Ser Gly Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Gly Gly Arg Tyr Cys Ser Ser Ile Ser Cys Tyr Ala Arg Ser Gly
                100                 105                 110

Cys Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr Ser
225                 230
```

<210> SEQ ID NO 10
<211> LENGTH: 205
<212> TYPE: PRT
<213> ORGANISM: Homo sapiens

<400> SEQUENCE: 10

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Ser
                85                  90                  95

Thr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro
        195                 200                 205
```

<210> SEQ ID NO 11
<211> LENGTH: 764
<212> TYPE: PRT
<213> ORGANISM: Homo sapiens

<400> SEQUENCE: 11

```
Met Arg Pro Ala Asp Leu Leu Gln Leu Val Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
```

-continued

```
            405                 410                 415
Leu Arg Ile Val Val Trp Phe Val Ser Leu Leu Ala Leu Leu Gly Asn
            420                 425                 430
Val Phe Val Leu Leu Ile Leu Leu Thr Ser His Tyr Lys Leu Asn Val
            435                 440                 445
Pro Arg Phe Leu Met Cys Asn Leu Ala Phe Ala Asp Phe Cys Met Gly
            450                 455                 460
Met Tyr Leu Leu Leu Ile Ala Ser Val Asp Leu Tyr Thr His Ser Glu
465                 470                 475                 480
Tyr Tyr Asn His Ala Ile Asp Trp Gln Thr Gly Pro Gly Cys Asn Thr
            485                 490                 495
Ala Gly Phe Phe Thr Val Phe Ala Ser Glu Leu Ser Val Tyr Thr Leu
            500                 505                 510
Thr Val Ile Thr Leu Glu Arg Trp Tyr Ala Ile Thr Phe Ala Met Arg
            515                 520                 525
Leu Asp Arg Lys Ile Arg Leu Arg His Ala Cys Ala Ile Met Val Gly
            530                 535                 540
Gly Trp Val Cys Cys Phe Leu Leu Ala Leu Leu Pro Leu Val Gly Ile
545                 550                 555                 560
Ser Ser Tyr Ala Lys Val Ser Ile Cys Leu Pro Met Asp Thr Glu Thr
            565                 570                 575
Pro Leu Ala Leu Ala Tyr Ile Val Phe Val Leu Thr Leu Asn Ile Val
            580                 585                 590
Ala Phe Val Ile Val Cys Cys Cys Tyr Val Lys Ile Tyr Ile Thr Val
            595                 600                 605
Arg Asn Pro Gln Tyr Asn Pro Gly Asp Lys Asp Thr Lys Ile Ala Lys
            610                 615                 620
Arg Met Ala Val Leu Ile Phe Thr Asp Phe Ile Cys Met Ala Pro Ile
625                 630                 635                 640
Ser Phe Tyr Ala Leu Ser Ala Ile Leu Asn Lys Pro Leu Ile Thr Val
            645                 650                 655
Ser Asn Ser Lys Ile Leu Leu Val Leu Phe Tyr Pro Leu Asn Ser Cys
            660                 665                 670
Ala Asn Pro Phe Leu Tyr Ala Ile Phe Thr Lys Ala Phe Gln Arg Asp
            675                 680                 685
Val Phe Ile Leu Leu Ser Lys Phe Gly Ile Cys Lys Arg Gln Ala Gln
            690                 695                 700
Ala Tyr Arg Gly Gln Arg Val Pro Pro Lys Asn Ser Thr Asp Ile Gln
705                 710                 715                 720
Val Gln Lys Val Thr His Asp Met Arg Gln Gly Leu His Asn Met Glu
            725                 730                 735
Asp Val Tyr Glu Leu Ile Glu Asn Ser His Leu Thr Pro Lys Lys Gln
            740                 745                 750
Gly Gln Ile Ser Glu Glu Tyr Met Gln Thr Val Leu
            755                 760
```